US009710909B2

(12) United States Patent
Akai et al.

(10) Patent No.: US 9,710,909 B2
(45) Date of Patent: Jul. 18, 2017

(54) METHOD FOR PRODUCING EMBRYOS BY IN VITRO CULTURE, AND METHOD, APPARATUS, AND SYSTEM FOR SELECTING EMBRYOS

(71) Applicant: Dai Nippon Printing Co., Ltd., Tokyo (JP)

(72) Inventors: Tomonori Akai, Tokyo (JP); Kei Imai, Fukushima (JP); Yoshio Aikawa, Fukushima (JP); Masaki Ohtake, Fukushima (JP); Satoshi Sugimura, Fukushima (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 14/849,751

(22) Filed: Sep. 10, 2015

(65) Prior Publication Data

US 2016/0247280 A1    Aug. 25, 2016

Related U.S. Application Data

(62) Division of application No. 13/807,346, filed as application No. PCT/JP2011/065070 on Jun. 30, 2011, now Pat. No. 9,163,274.

(30) Foreign Application Priority Data

Jun. 30, 2010  (JP) ................................ 2010-149500
Jun. 29, 2011  (JP) ................................ 2011-144932

(51) Int. Cl.
*G06T 7/00*      (2017.01)
*G01N 33/483*    (2006.01)
(Continued)

(52) U.S. Cl.
CPC .......... *G06T 7/0016* (2013.01); *A01K 67/027* (2013.01); *A61B 17/435* (2013.01);
(Continued)

(58) Field of Classification Search
CPC ............ A01K 67/027; A01K 2227/101; C12N 5/0604; C12M 41/48; C12M 21/06; C12M 41/46; C12Q 1/04; A61B 17/435
See application file for complete search history.

(56) References Cited

U.S. PATENT DOCUMENTS

2006/0099570 A1* 5/2006 Damgaard ......... G01N 33/5038
                                                    435/4
2008/0247628 A1  10/2008 Ramsing et al.
2010/0041090 A1*  2/2010 Ramsing .............. C12N 5/0604
                                                    435/29

FOREIGN PATENT DOCUMENTS

JP    2002-122568    4/2002
JP    2009-539387   11/2009
JP    2010-004789    1/2010

OTHER PUBLICATIONS

Aoyagi, Shigeo, et al., "Quality Evaluation of in Vitro-Produced Bovine Embryos by Respiration Measurement and Development of Semi-Automatic Instrument", Journal of Japan Society for Analytical Chemistry, 2006, vol. 55, No. 11, pp. 847-854.

(Continued)

*Primary Examiner* — Christine H Matthews
*Assistant Examiner* — Joshua D Lannu
(74) *Attorney, Agent, or Firm* — McCarter & English, LLP

(57) ABSTRACT

An object of the present invention is to provide a method for efficiently obtaining mammalian embryos having high conception rates. A first aspect of the present invention is a method for selecting a mammalian embryo prepared by in vitro culture from a fertilized egg, comprising a step of (Continued)

selecting an embryo using two or more of the following indicators: the time from fertilization to the completion of first cleavage; the morphology at a stage after first cleavage and before second cleavage; the morphology at a stage after third cleavage and before fourth cleavage; and the amount of oxygen consumed at the early blastocyst stage, the blastocyst stage, or the expanded blastocyst stage.

5 Claims, 34 Drawing Sheets

(51) Int. Cl.

| | |
|---|---|
| *A01K 67/027* | (2006.01) |
| *C12N 5/073* | (2010.01) |
| *A61B 17/435* | (2006.01) |
| *C12Q 1/04* | (2006.01) |
| *C12M 3/00* | (2006.01) |
| *C12M 1/34* | (2006.01) |
| *C12M 1/36* | (2006.01) |

(52) U.S. Cl.
CPC ............ *C12M 21/06* (2013.01); *C12M 41/46* (2013.01); *C12M 41/48* (2013.01); *C12N 5/0604* (2013.01); *C12Q 1/04* (2013.01); *G01N 33/4833* (2013.01); *A01K 2227/101* (2013.01); *G06T 2207/10016* (2013.01); *G06T 2207/30044* (2013.01)

(56) References Cited

OTHER PUBLICATIONS

Dang-Nguyen, Thanh Quang, et al., "Evaluation of Development Competence of In Vitro-Produced Porcine Embryos Based on the Timing, Pattern and Evenness of the First Cleavage and Onset of the Second Cleavage", Journal of Reproduction and Development, 2010, vol. 56, No. 6, pp. 593-600.

International Search Report based on International Application No. PCT/JP2011/065070, dated Aug. 30, 2011.

* cited by examiner

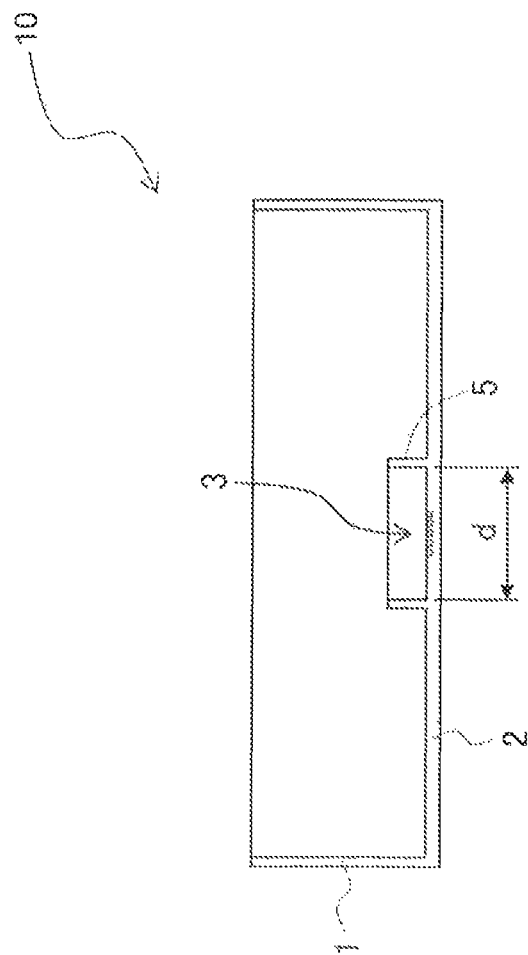

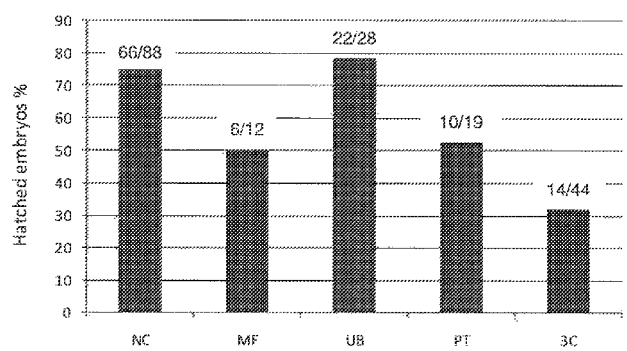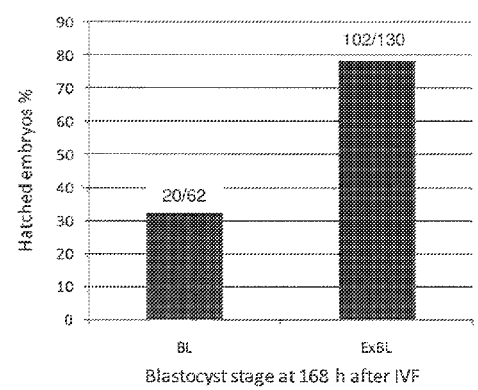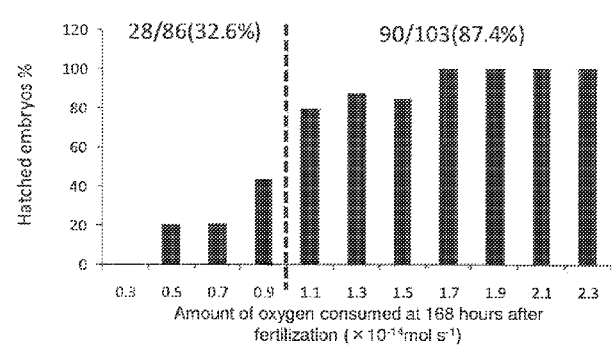

Fig. 23a

| Address | | | 2nd indicator determination | | 3rd indicator determination | | | 4th indicator determination | | Analysis step |
|---|---|---|---|---|---|---|---|---|---|---|
| Line | Column | ID | Number of cells | Presence or absence of fragmentation (Y/N) | 2nd indicator condition satisfied ? | Number of cells | Presence or absence of fragmentation (Y/N) | 3rd indicator condition satisfied ? | Amount of oxygen consumed ($\times 10^{-14}$) | 4th indicator condition satisfied ? | O.K./NG |
| 1 | 1 | 1 | | | | | | | | | |
| | | 2 | | | | | | | | | |
| 1 | 2 | 1 | | | | | | | | | |
| 1 | 3 | 1 | | | | | | | | | |
| | | 2 | | | | | | | | | |
| 1 | 4 | 1 | | | | | | | | | |
| 1 | 5 | 1 | | | | | | | | | |
| 2 | 1 | 1 | | | | | | | | | |

Fig. 23b

| Address | | | | 2nd indicator determination | | 3rd indicator determination | | | 4th indicator determination | | Analysis step |
|---|---|---|---|---|---|---|---|---|---|---|---|
| Line | Column | ID | Number of cells | Presence or absence of fragmentation (Y/N) | 2nd indicator condition satisfied? | Number of cells | Presence or absence of fragmentation (Y/N) | 3rd indicator condition satisfied? | Amount of oxygen consumed ($\times 10^{-14}$) | 4th indicator condition satisfied? | OK/NG |
| 1 | 1 | 1 | 2 | N | OK | | | | | | |
| 1 | 1 | 2 | 2 | N | OK | | | | | | |
| 1 | 2 | 1 | 1 | Y | NG | | | | | | |
| 1 | 3 | 1 | 2 | Y | NG | | | | | | |
| 1 | 3 | 2 | 2 | N | OK | | | | | | |
| 1 | 4 | 1 | 1 | Y | NG | | | | | | |
| 1 | 5 | 1 | 2 | Y | NG | | | | | | |
| 2 | 1 | 1 | 2 | N | OK | | | | | | |

Fig. 23c

| Address | | | 2nd indicator determination | | | 3rd indicator determination | | | 4th indicator determination | | Analysis step |
|---|---|---|---|---|---|---|---|---|---|---|---|
| Line | Column | ID | Number of cells | Presence or absence of fragmentation (Y/N) | 2nd indicator condition satisfied? | Number of cells | Presence or absence of fragmentation (Y/N) | 3rd indicator condition satisfied? | Amount of oxygen consumed ($\times 10^{-14}$) | 4th indicator condition satisfied? | O.K./NG |
| 1 | 1 | 1 | 2 | N | O.K. | 6 | N | OK | | | OK |
| 1 | 1 | 2 | 2 | N | O.K. | 7 | N | OK | | | OK |
| 1 | 2 | 1 | 1 | Y | NG | 8 | Y | NG | | | NG |
| 1 | 3 | 1 | 2 | Y | NG | 5 | N | O.K. | | | |
| 1 | 3 | 2 | 2 | N | O.K. | 8 | Y | NG | | | |
| 1 | 4 | 1 | 1 | Y | NG | 4 | Y | NG | | | NG |
| 1 | 5 | 1 | 2 | Y | NG | 4 | N | NG | | | NG |
| 2 | 1 | 1 | 2 | N | O.K. | 4 | N | NG | | | NG |

Fig. 23d

| Address | | | 2nd indicator determination | | | 3rd indicator determination | | | 4th indicator determination | | Analysis step |
|---|---|---|---|---|---|---|---|---|---|---|---|
| Line | Column | ID | Number of cells | Presence or absence of fragmentation (Y/N) | 2nd indicator condition satisfied? | Number of cells | Presence or absence of fragmentation (Y/N) | 3rd indicator condition satisfied? | Amount of oxygen consumed (×10⁻¹⁴) | 4th indicator condition satisfied? | OK/NG |
| 1 | 1 | 1 | 2 | N | O.K. | 6 | N | O.K. | - | - | O.K. |
| 1 | 1 | 2 | 2 | N | O.K. | 7 | N | O.K. | - | - | O.K. |
| 1 | 2 | 1 | 1 | Y | NG | 8 | Y | NG | - | - | NG |
| 1 | 3 | 1 | 2 | Y | NG | 5 | N | O.K. | 1.1 | O.K. | O.K. |
| 1 | 3 | 2 | 2 | N | O.K. | 8 | Y | NG | 1.02 | O.K. | O.K. |
| 1 | 4 | 1 | 1 | Y | NG | 4 | Y | NG | - | - | NG |
| 1 | 5 | 1 | 2 | Y | NG | 4 | N | NG | - | - | NG |
| 2 | 1 | 1 | 2 | N | O.K. | 4 | N | NG | 0.6 | NG | NG |

METHOD FOR PRODUCING EMBRYOS BY IN VITRO CULTURE, AND METHOD, APPARATUS, AND SYSTEM FOR SELECTING EMBRYOS

RELATED APPLICATIONS

This application is a divisional of U.S. application Ser. No. 13/807,346, filed Dec. 28, 2012, which is a national stage application filed under 35 USC §371 of PCT/JP2011/065070, filed Jun. 30, 2011, which claims the benefit of Japanese Patent Application Nos. 2010-149500, filed Jun. 30, 2010, and 2011-144932, filed Jun. 29, 2011. The entire contents of each of the above-mentioned priority applications are incorporated herein by reference in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119244_00087_Sequence_Listing. The size of the text file is 17 KB, and the text file was created on Sep. 2, 2015.

TECHNICAL FIELD

The present invention relates to a method for selecting embryos having high conception rates from among mammalian embryos obtained by in vitro culture, a method for producing embryos having high conception rates from mammalian fertilized eggs (synonymous with the term "zygote(s)") by in vitro culture, and a method for producing mammals using embryos obtained by these methods.

BACKGROUND ART

Technology has been established for many mammals such as cattle, whereby fertilized eggs are obtained by in vitro fertilization, embryos are developed from fertilized eggs by in vitro culture, the thus obtained embryos are implanted into the uteri of recipient females for conception, and thus progeny are obtained.

However, embryos obtained by in vitro culture are problematic due to low conception rates. For example, the conception rates of cattle range from 40% to 50%. Human pregnancy success rates range from about 25% to 35%. Possible reasons therefor are poor development and the like, since in vitro culture environments differ from in vivo environments.

Development of techniques for selecting embryos having high conception rates based on morphology or biochemical indicators have been attempted.

Non-patent document 1 discloses that in human fertilized eggs, conception rates differ depending on the number of cells and fragmentation at the time of third cleavage.

Non-patent document 2 discloses that in human fertilized eggs, the conception rates are improved when there are few instances of fragmentation.

Non-patent documents 3 and 4 describe that in bovine fertilized eggs, when the number of cells at the time of third cleavage is not 5 to 8 cells, chromosome aberration takes place particularly easily.

Non-patent document 5 describes that in bovine fertilized eggs, conception rates fluctuate depending on respiratory volume (the amount of oxygen consumed), and a respiratory volume of 0.78-1.10 nl/h leads to the highest conception rate.

Non-patent document 6 describes the examination of the relationship between combinations of a plurality of indicators (e.g., the number of cells at the time of initial cleavage, the time required for initial cleavage to take place, the uniformity of 2-cell embryos at the time of initial cleavage, the number of cells at the time of second cleavage, amino acid level, and the like in porcine fertilized eggs) and blastocyst (%).

Patent document 1 discloses an invention relating to a method for evaluating embryo quality. The document describes that unsynchronized cell division at the time of cleavage and fragmentation phenomenon can be used as indicators for quality evaluation. The document further describes that these indicators may be combined with other indicators such as respiration rate.

Patent document 2 discloses an apparatus and a method for measuring the amount of oxygen consumed per single embryo in order to evaluate embryo quality.

The relationship between each individual indicator and embryo quality has been examined as described above. However, no prior art exists in which the relationship between a combination of a plurality of indicators and conception rate is specifically examined.

Furthermore, in the case of cattle, even the relationship between an individual indicator and conception rate has almost never been examined under current circumstances.

Meanwhile, fertilized eggs of a non-human mammal are generally cultured by a method that involves placing droplets of a culture solution in wells on a culture vessel, coating the surfaces of the microdroplets with mineral oil, and then placing a plurality of fertilized eggs within one droplet (droplet method). This method is problematic in terms of differential management of individual embryos. Hence, embryo quality is determined using as an indicator only the morphological observation for embryos at the completion of culture (the early blastocyst stage, the blastocyst stage, or the expanded blastocyst stage). Conventional methods for culturing embryos are problematic in terms of obtaining indicators for selecting embryos having high conception rates by following embryonic growth process over time from the initial cleavage to the completion of culture so as to obtain data, and then combining data at different time points. Such a method of obtaining indicators has never been examined conventionally.

CITATION LIST

Patent Documents

Patent Document 1: JP Patent Publication (Kohyo) No. 2009-539387 A
Patent document 2: JP Patent No. 3693907

Non-Patent Documents

Non-patent document 1: Human Reproduction Vol. 16, No. 9, pp. 1970-1975, 2001
Non-patent document 2: Human Reproduction Vol. 17, No. 9, pp. 2402-2409, 2002
Non-patent document 3: BIOLOGY OF REPRODUCTION 63, 1143-1148 (2000)
Non-patent document 4: Journal of Reproduction and Development, Vol. 54, No. 6, 465-472 (2008)

Non-patent document 5: Human Reproduction Vol. 22, No. 2, pp. 558-566, 2007

Non-patent document 6: BIOLOGY OF REPRODUCTION 77, 765.779 (2007)

SUMMARY OF INVENTION

Technical Problem

An object of the present invention is to provide a means for efficiently obtaining mammalian embryos having high conception rates.

Solution to Problem

The present inventors have obtained data by following the embryonic growth process over time from the initial cleavage to the completion of culture (the early blastocyst stage, the blastocyst stage, or the expanded blastocyst stage) using culture vessels filed under JP patent application No. 2010-022463 (shown in FIG. 1a to FIG. 1f of the present application), with which cells can be individually managed. The relationship between data obtained at different time points for one embryo and conception rate has been examined. As a result, the present inventors have surprisingly found that embryos satisfying 2, 3, or 4 conditions from among predetermined conditions at four different embryonic developmental stages exhibit high conception rates, and thus have completed the present invention.

The present invention encompasses the following (1) to (13).

(1) A method for selecting a mammalian embryo prepared by in vitro culture from a fertilized egg, comprising a step of selecting an embryo using two or more of the following indicators:

the time from fertilization to the completion of first cleavage;

the morphology at a stage after first cleavage and before second cleavage;

the morphology at a stage after third cleavage and before fourth cleavage; and the amount of oxygen consumed at the early blastocyst stage, the blastocyst stage, or the expanded blastocyst stage.

(2) The method of (1), wherein the embryo selected in the step satisfies two or more of the following conditions:

at least one condition selected from the following condition "d1" to "d3" is satisfied (condition "d"): the time from fertilization to the completion of first cleavage of an embryo is confirmed to result in a probability of 40% or more that the chromosome number of the embryo at the blastocyst stage will be normal, based on the correlation between the time from fertilization to the completion of first cleavage of the embryo and the probability (condition "d1"), the time from fertilization to the completion of first cleavage of an embryo is confirmed to result in an expression level of 0.45 or more of an IGF2R gene in the embryo at the blastocyst stage relative to the expression level of an H2AFZ gene designated as 1, based on the correlation between the time from fertilization to the completion of first cleavage of the embryo and the relative expression level (condition "d2"), and, the time from fertilization to the completion of first cleavage of an embryo is confirmed to result in an expression level of 0.2 or more of an IFN-tau gene in the embryo at the blastocyst stage relative to the expression level of an H2AFZ gene designated as 1, based on the correlation between the time from fertilization to the completion of first cleavage of the embryo and the relative expression level (condition "d3");

the embryo is a 2-cell embryo at a stage after first cleavage and before second cleavage, and undergoes no fragmentation (condition "a");

the embryo is a 5-cell, 6-cell, 7-cell, or 8-cell embryo at a stage after third cleavage and before fourth cleavage and undergoes no fragmentation (condition "b"); and the amount of oxygen consumed at the early blastocyst stage, the blastocyst stage, or the expanded blastocyst stage is confirmed to result in a probability of 50% or more that the embryo will reach the hatched blastocyst stage, based on the correlation between the amount of oxygen consumed by the embryo at the early blastocyst stage, the blastocyst stage, or the expanded blastocyst stage and the probability (condition "c").

(3) The method of (2), wherein the mammal is cattle, the time in condition "d" from fertilization to the completion of first cleavage is 27 hours or less, and the amount of oxygen consumed in condition "c" is $0.91 \times 10^{-14}$ mol s$^{-1}$ or more per single embryo.

(4) A method for producing an embryo by in vitro culture from a mammalian fertilized egg, comprising a selection step of selecting an embryo using two or more indicators of:

the time from fertilization to the completion of first cleavage;

the morphology at a stage after first cleavage and before second cleavage;

the morphology at a stage after third cleavage and before fourth cleavage; and the amount of oxygen consumed at the early blastocyst stage, the blastocyst stage, or the expanded blastocyst stage.

(5) The method of (4), wherein the embryo selected in the selection step satisfies two or more of the following conditions:

at least one condition selected from the following condition "d1" to "d3" is satisfied (condition "d"): the time from fertilization to the completion of first cleavage of an embryo is confirmed to result in a probability of 40% or more that the chromosome number of the embryo at the blastocyst stage will be normal, based on the correlation between the time from fertilization to the completion of first cleavage and the probability (condition "d1"), the time from fertilization to the completion of first cleavage of an embryo is confirmed to result in the expression level of 0.45 or more of an IGF2R gene of the embryo at the blastocyst stage relative to the expression level of an H2AFZ gene designated as 1, based on the correlation between the time from fertilization to the completion of first cleavage and the relative expression level (condition "d2"), and the time from fertilization to the completion of first cleavage of an embryo is confirmed to result in the expression level of 0.2 or more of an IFN-tau gene in the embryo at the blastocyst stage relative to the expression level of an H2AFZ gene designated as 1, based on the correlation between the time from fertilization to the completion of first cleavage and the relative expression level (condition "d3");

the embryo is a 2-cell embryo at a stage after first cleavage and before second cleavage and undergoes no fragmentation (condition "a");

the embryo is a 5-cell, 6-cell, 7-cell, or 8-cell embryo at a stage after third cleavage and before fourth cleavage, and undergoes no fragmentation (condition "b"); and the amount of oxygen consumed at the early blastocyst stage, the blastocyst stage, or the expanded blastocyst stage is confirmed to result in a probability of 50% or more that an embryo will reach the hatched blastocyst stage, based on the correlation between the amount of oxygen consumed by the embryo at the early blastocyst stage, the blastocyst stage, or the expanded blastocyst stage, and the probability (condition "c").

(6) The method of (5), wherein the mammal is cattle, the time in condition "d" from fertilization to the completion of first cleavage is 27 hours or less, and the amount of oxygen consumed in condition "c" is $0.91 \times 10^{-14}$ mol s$^{-1}$ or more per single embryo.

(7) A method for producing a mammalian individual, comprising a step of implanting an embryo selected by the method of any one of (1) to (3), or an embryo produced by the method of any one of (4) to (6) into a female individual for conception.

(8) An embryo selection apparatus for selecting a mammalian candidate embryo prepared by in vitro culture from a fertilized egg, comprising a determination unit and an analysis unit, wherein:

the determination unit comprises M (where M is the number 2, 3, or 4) sections of, a $1_{st}$ indicator determination section for determining whether or not $1_{st}$ indicator information concerning the time from fertilization to the completion of first cleavage of a candidate embryo satisfies a $1_{st}$ indicator selection criterion concerning the time from fertilization to the completion of first cleavage, a $2^{nd}$ indicator determination section for determining whether or not $2^{nd}$ indicator information concerning the morphology of a candidate embryo at a stage after first cleavage and before second cleavage satisfies a $2^{nd}$ indicator selection criterion concerning the morphology at a stage after first cleavage and before second cleavage, a $3^{rd}$ indicator determination section for determining whether or not $3^{rd}$ indicator information concerning the morphology of a candidate embryo at a stage after third cleavage and before fourth cleavage satisfies a $3^{rd}$ indicator selection criterion concerning the morphology at a stage after third cleavage and before fourth cleavage, and a $4^{th}$ indicator determination section for determining whether or not $4^{th}$ indicator information concerning the amount of oxygen consumed by a candidate embryo at the early blastocyst stage, the blastocyst stage, or the expanded blastocyst stage satisfies a $4^{th}$ indicator selection criterion concerning the amount of oxygen consumed at the early blastocyst stage, the blastocyst stage, or the expanded blastocyst stage; and the analysis unit analyzes that a candidate embryo satisfying N (where N is the number 2 or more and M or less) or more conditions from among conditions determined in the determination unit is an embryo to be selected.

(9) The embryo selection apparatus of (8) further comprising an image extraction unit, wherein:

when the determination unit comprises the $1^{st}$ indicator determination section, the image extraction unit comprises a $1^{st}$ image extraction section for extracting an image at the threshold time point of the time from fertilization to the completion of first cleavage specified by the $1^{st}$ indicator selection criterion, or, an image with which the time point of the completion of first cleavage can be confirmed, from the images of candidate embryos, and the $1^{st}$ indicator determination section determines information generated based on the image extracted by the $1^{st}$ image extraction section as the $1^{st}$ indicator information;

when the determination unit comprises the $2^{nd}$ indicator determination section, the image extraction unit comprises a $2^{nd}$ image extraction section for extracting an image at a stage after first cleavage and before second cleavage from the images of candidate embryos, and the $2^{nd}$ indicator determination section determines information generated based on the image extracted by the $2^{nd}$ image extraction section as the $2^{nd}$ indicator information;

when the determination unit comprises the $3^{rd}$ indicator determination section, the image extraction unit comprises a $3^{rd}$ image extraction section for extracting an image at a stage after third cleavage and before fourth cleavage from the images of candidate embryos, and the $3^{rd}$ indicator determination section determines information generated based on the image extracted by the $3^{rd}$ image extraction section as the $3^{rd}$ indicator information.

(10) An embryo selection system for selecting a mammalian candidate embryo prepared by in vitro culture from a fertilized egg, comprising: the embryo selection apparatus of (9); and an image pickup apparatus for imaging candidate embryos, and then outputting the thus taken images to the image extraction unit, and further comprising, when the determination unit comprises the $4^{th}$ indicator determination section:

an apparatus for measuring the amount of oxygen consumed by candidate embryos at the early blastocyst stage, the blastocyst stage, or the expanded blastocyst stage are measured, and outputting the measured amounts of oxygen consumed to the $4^{th}$ indicator determination section.

(11) A program for a computer to execute an embryo selection method for selecting a mammalian candidate embryo prepared by in vitro culture from a fertilized egg.

wherein the method comprises determination step and an analysis step;

wherein the determination step comprise M (where M is the number 2, 3, or 4) steps of:

a $1^{st}$ indicator determination step for determining whether or not $1_{st}$ indicator information concerning the time from fertilization to the completion of first cleavage of a candidate embryo satisfies a $1^{st}$ indicator selection criterion concerning the time from fertilization to the completion of first cleavage.

a $2^{nd}$ indicator determination step for determining whether or not $2^{nd}$ indicator information concerning the morphology of a candidate embryo at a stage after first cleavage and before second cleavage satisfies a $2^{nd}$ indicator selection criterion concerning the morphology at a stage after first cleavage and before second cleavage;

a $3^{rd}$ indicator determination step for determining whether or not $3^{rd}$ indicator information concerning the morphology of a candidate embryo at a stage after third cleavage and before fourth cleavage satisfies a $3^{rd}$ indicator selection criterion concerning the morphology at a stage after third cleavage and before fourth cleavage, and a $4^{th}$ indicator determination step for determining whether or not $4^{th}$ indicator information concerning the amount of oxygen consumed by a candidate embryo at the early blastocyst stage, the blastocyst stage, or the expanded blastocyst stage satisfies a $4^{th}$ indicator selection criterion concerning the amount of oxygen consumed at the early blastocyst stage, the blastocyst stage, or the expanded blastocyst stage; and wherein the analysis step comprises analyzing a candidate embryo that satisfies N (where N is the number 2 or more and M or less) or more conditions determined by the determination step as an embryo to be selected.

The present invention further encompasses the following embodiments.

(12) A method for predicting the conception rate of an embryo in a method for developing an embryo from a human fertilized egg by in vitro culture, using two or more indicators of:

the time from fertilization to the completion of first cleavage;

the morphology at a stage after first cleavage and before second cleavage;

the morphology at a stage after third cleavage and before fourth cleavage; and the amount of oxygen consumed at the early blastocyst stage, the blastocyst stage, or the expanded blastocyst stage.

(13) The method of (12) for predicting an embryo that satisfies two or more of the following conditions as having a high conception rate:

at least one condition selected from the following condition "d1" to "d3" is satisfied (condition "d"): the time from fertilization to the completion of first cleavage of an embryo is confirmed to result in a probability of 40% or more that the chromosome number of the embryo at the blastocyst stage will be normal, based on the correlation between the time from fertilization to the completion of first cleavage and the probability (condition "d1"), the time from fertilization to the completion of first cleavage of an embryo is confirmed to result in the expression level of 0.45 or more of an IGF2R gene in the embryo at the blastocyst stage relative to the expression level of an H2AFZ gene designated as 1, based on the correlation between the time from fertilization to the completion of first cleavage and the relative expression level (condition "d2"), and, the time from fertilization to the completion of first cleavage of an embryo is confirmed to result in the expression level of 0.2 or more of an IFN-tau gene of the embryo at the blastocyst stage relative to the expression level of an H2AFZ gene designated as 1, based on the correlation between the time from fertilization to the completion of first cleavage and the relative expression level (condition "d3");

the embryo is a 2-cell embryo at a stage after first cleavage and before second cleavage and undergoes no fragmentation (condition "a");

the embryo is a 5-cell, 6-cell, 7-cell, or 8-cell embryo at a stage after third cleavage and before fourth cleavage, and undergoes no fragmentation (condition "b"); and the amount of oxygen consumed at the early blastocyst stage, the blastocyst stage, or the expanded blastocyst stage is confirmed to result in a probability of 50% or more that an embryo will reach the hatched blastocyst stage based on a correlation between the amount of oxygen consumed by the embryo at the early blastocyst stage, the blastocyst stage, or the expanded blastocyst stage and the probability (condition "c").

This description includes part or all of the contents as disclosed in the descriptions and/or drawings of JP Application No. 2010-149500 and JP Application No. 2011-144932 which are priority documents of the present application.

Advantageous Effects of Invention

According to the present invention, mammalian embryos having high conception rates can be efficiently obtained.

BRIEF DESCRIPTION OF DRAWINGS

FIG. 1b is an 1a-1a sectional view of FIG. 1a.
FIG. 1c shows a partial enlarged view of a cell holding section in FIG. 1a.
FIG. 4 shows the relationship between the first cleavage pattern at 31 hours after fertilization and hatching from the zona pellucida (FIG. 4(a)), the relationship between the blastocyst stage at 168 hours after fertilization and hatching from the zona pellucida (FIG. 4(b)), and the relationship between oxygen consumed at 168 hours after fertilization and hatching from the zona pellucida (FIG. 4(c)) in a preliminary examination.

FIG. 23a shows information for specifying individual candidate embryos, which is stored in advance in the method for selecting embryos using the embryo selection apparatus of the present invention.

FIG. 23b shows the results generated by the $2^{nd}$ indicator determination step of the method for selecting embryos using the embryo selection apparatus of the present invention.

FIG. 23c shows the results generated by the $3^{rd}$ indicator determination step of the method for selecting embryos using the embryo selection apparatus of the present invention.

FIG. 23d shows the results generated by the $4^{th}$ indicator determination step of the method for selecting embryos using the embryo selection apparatus of the present invention.

DESCRIPTION OF EMBODIMENTS

Figure 1A:
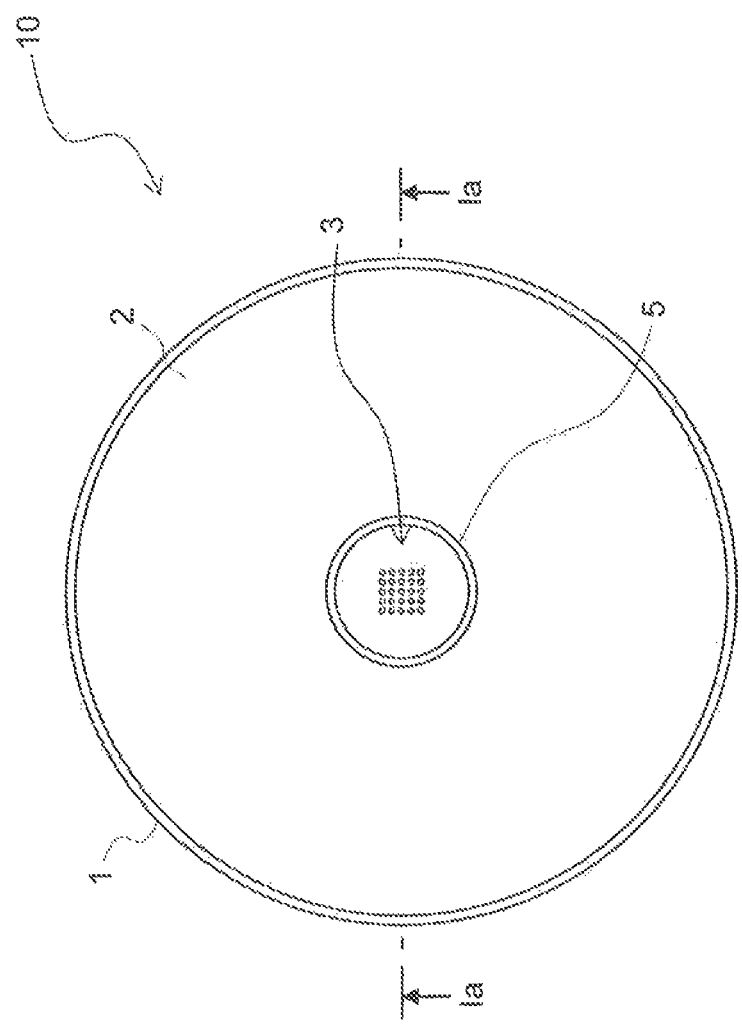
FIG. 1a is a plan view showing a culture vessel C that can be used for performing the method of the present invention.
Figure 1C:
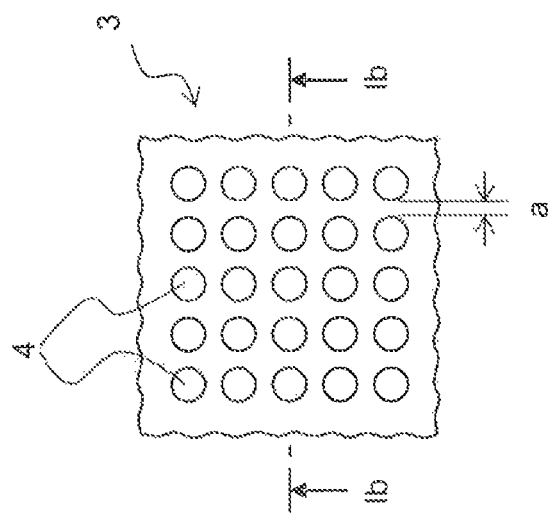
Figure 1D:
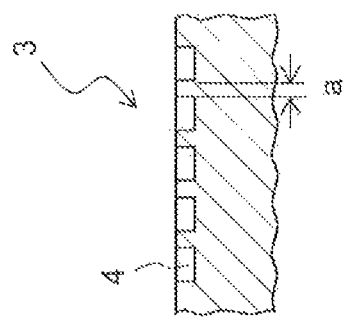
FIG. 1d is an 1b-1b sectional view of FIG. 1c.
Figure 1E:
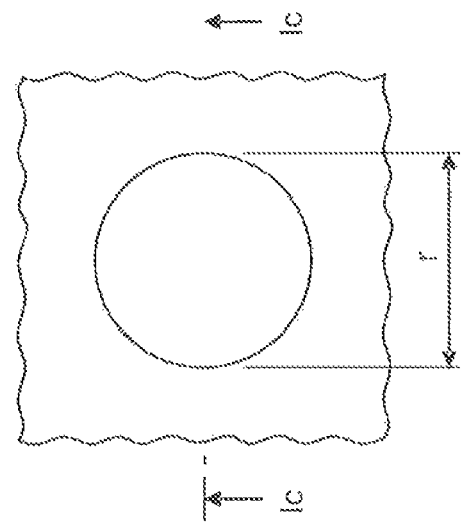
FIG. 1e shows a partial enlarged view of microwells in FIG. 1c.
Figure 1F:
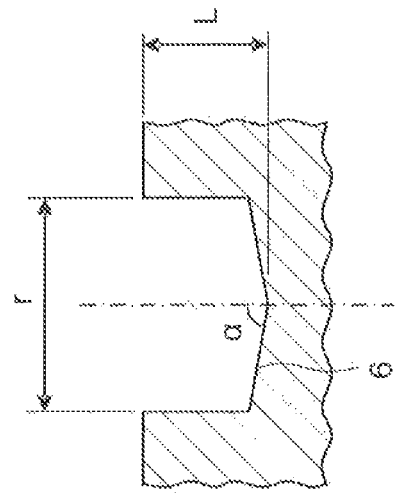
FIG. 1f is an 1c-1c sectional view of FIG. 1e.

In the present invention, the term "mammal(s)" refers to warm blooded vertebrates. Examples thereof include primates such as humans and monkeys, rodents such as mice, rats, and rabbits, pet animals such as dogs and cats, and domestic animals such as cattle, horses, pigs, and sheep. The method of the present invention is typically used for non-human mammals (mammals other than humans). In the present invention, the term "human" refers to *Homo sapiens*. The term "monkey" refers to non-human animals that are classified as members of the Order Primates. The term "mouse" refers to *Mus musculus*. The term "rat" refers to *Rattus norvegicus*. The term "rabbit" refers to animals classified as members of the family Leporidae. The term "dog" refers to animals classified as *Canis lupus*, and typically refers to *Canis lupus familiaris*. The term "cat" refers to animals classified as *Felis silvestris*, and typically refers to *Felis silvestris catus*. The term "cattle" refers to animals classified as members of the genus *Bos*, and typically refers to *Bos Taurus* and *Bos indicus*. The term "horse" refers to *Equus caballus*. The term "pig (or swine)" refers to animals classified as *Sus scrofa*, and typically refers to *Sus scrofa domesticus*. The term "sheep" refers to *Ovis aries*.

A mammalian fertilized egg divides into a 2-cell stage, a 4-cell stage, and then an 8-cell stage via cleavage after fertilization so that the number of cells increases, and then it develops into a morula and then into a blastocyst (early blastocyst to hatched blastocyst). Embryos to be subjected to selection or production in the present invention are embryos that have developed to an 8-cell stage (that is, after the completion of third cleavage) and the following cell stages. Examples of such an embryo include a morula, an early blastocyst, a blastocyst, an expanded blastocyst, and a hatched blastocyst. Typical examples thereof include an early blastocyst, a blastocyst, an expanded blastocyst, and a hatched blastocyst. An early blastocyst, a blastocyst, an expanded blastocyst, and a hatched blastocyst are provided with inner cell masses that are potentially capable of forming embryos with external cells that are potentially capable of forming placenta.

The present inventors have surprisingly found that an embryo having a high conception rate can be predicted using 2 or more, and preferably 3 of the following indicators:

the morphology at a stage after first cleavage and before second cleavage:

the morphology after third cleavage and before fourth cleavage; and the amount of oxygen consumed at the early blastocyst stage, the blastocyst stage, or the expanded blastocyst stage. When only one of the three indicators is used as an indicator for prediction or when a combination of one of the three indicators and another known indicator (e.g., morphological quality determined to be Code 1 or an embryo that has reached the expanded blastocyst stage) is used for prediction, an embryo having a high conception rate cannot be selected.

More specifically, the present inventors have found that an embryo satisfying two or more of the following conditions has a high conception rate:

the embryo is a 2-cell embryo at a stage after first cleavage and before second cleavage, and undergoes no fragmentation (condition "a");

the embryo is a 5-cell, 6-cell, 7-cell, or 8-cell embryo at a stage after third cleavage and before fourth cleavage, and undergoes no fragmentation (condition "b"); and the amount of oxygen consumed by an embryo at the early blastocyst stage, the blastocyst stage, or the expanded blastocyst stage is confirmed to result in a probability of 50% or more that the embryo will reach the hatched blastocyst stage, based on the correlation between the amount of oxygen consumed by the embryo at the early blastocyst stage, the blastocyst stage, or the expanded blastocyst stage and the probability (condition "c").

Condition "b" in the present invention may be a condition that "the embryo is a 6-cell, 7-cell, or 8-cell embryo at a stage after third cleavage and before fourth cleavage, and undergoes no fragmentation.

The present inventors have further found that an embryo having a high conception rate can be predicted using 2 or more, preferably 3 or more, and more preferably 4 indicators from among the 4 indicators (including an indicator of the time from fertilization to the completion of first cleavage and the above three indicators).

Specifically, the present inventors have found that an embryo satisfying 2 or more, preferably 3 or more, and more preferably 4 conditions below has a high conception rate: at least one condition selected from the following condition "d1" to "d3" is satisfied (condition "d"); the time from fertilization to the completion of first cleavage of an embryo is confirmed to result in a probability of 40% or more that the chromosome number of the embryo at the blastocyst stage will be normal, based on a correlation between the time from fertilization to the completion of first cleavage and the probability (condition "d1"), the time from fertilization to the completion of first cleavage of an embryo is confirmed to result in the expression level of 0.45 or more of an IGF2R gene in the embryo at the blastocyst stage relative to the expression level of an H2AFZ gene designated as 1, based on the correlation between the time from fertilization to the completion of first cleavage and the relative expression level (condition "d2"), and, the time from fertilization to the completion of first cleavage of an embryo is confirmed to result in the expression level of 0.2 or more of an IFN-tau gene in the embryo at the blastocyst stage relative to the expression level of an H2AFZ gene designated as 1, based on the correlation between the time from fertilization to the completion of first cleavage and the relative expression level (condition "d3");

the above condition "a";
the above condition "b"; and
the above condition "c."

Incubators to be used in the present invention are not limited to the incubators shown in FIG. 1 used in Experiment 1, and any incubator can be used herein. In the present invention, in vitro culture for developing embryos from fertilized eggs is preferably performed using incubators that can be individually managed.

As for various conditions such as medium, temperature, and the composition of atmospheric gas to be used for culturing embryos, conditions that are generally used can be employed depending on the mammalian species.

As typical culture conditions for cattle embryos, preferably, temperatures ranging from 38.0° C. to 39.5° C. and more preferably ranging from 38.5° C. to 39° C., medium such as SOF (synthetic oviduct fluid), modified SOF, IVD-101, TCM199, or CR1aa, and gas such as gas with saturated humidity containing 4.5% to 5.5% $CO_2$ and the remainder air (e.g., saturated humidity and 5% $CO_2$/95% air), or gas with saturated humidity containing 4.5% to 5.5% $CO_2$, 4.5% to 5.5% $O_2$, and the remainder $N_2$ (e.g., saturated humidity·5% $CO_2$/5% $O_2$/90% $N_2$) can be employed, for example.

As a typical culture condition for swine embryos, medium such as NCSU23, TCM199, or PZM5 can be employed.

A method for obtaining a fertilized egg (zygote) is not particularly limited. A fertilized egg can be prepared by in vitro fertilization of an egg cell with sperm.

Morphological observation can be performed by a non-invasive means such as microscopy. In general, morphology is observed with 40 times to 200 times magnification.

The term "fragmentation" in the present invention refers to a phenomenon where fragmented cells (cytoplasmic globules) are observed in addition to original cells after cleavage. The term "embryo(s) not undergoing fragmentation" refers to embryos for which no fragmentation is observed. The term "fragmentation" as used herein refers to such a phenomenon of fragmentation regardless of the presence or the absence of nuclei contained in fragmented cells (cytoplasmic globules).

The number of cells contained in embryos is determined visually from microscopically observed images. In the case of cattle, the number of cells in an embryo at up to about 8-cell stage can be visually counted.

Condition "d1," "the time from fertilization to the completion of first cleavage of an embryo is confirmed to result in a probability of 40% or more that the chromosome number of the embryo at the blastocyst stage will be normal, based on the correlation between the time from fertilization to the completion of first cleavage of the embryo and the probability" is described as follows. The present inventors have found in a preliminary examination: that the time from fertilization to the completion of first cleavage of a cattle embryo (hereinafter, may also be referred to as "the first cleavage time") correlates with the probability that the chromosome number of the embryo at the blastocyst stage will be normal; and that when the first cleavage time is equal to or less than a threshold, the probability that the chromosome number of the embryo at the blastocyst stage will be normal tends to drastically increase. Under in vitro culture conditions substantially the same as those employed for the method of the present invention, the correlation between the time from fertilization to the completion of first cleavage of an embryo and the probability that the chromosome number of the embryo at the blastocyst stage will be normal can be confirmed in advance also for mammals other than cattle. To select embryos having high conception rates, selection of embryos exhibiting a time of first cleavage confirmed to result in such a probability of 40% or more is effective. To narrow down the number of selected embryos, embryos exhibiting a time of first cleavage confirmed to result in a probability of 50% or more can be selected. To further narrow down the number of selected embryos, embryos exhibiting a time of first cleavage confirmed to result in a probability of 60% or more can be selected.

The blastocyst stage is defined as follows. Embryos having normal chromosome numbers are those wherein the nuclear phase of all cells analyzed has the normal number of autosomes and the normal number of sex chromosomes according to animal species. For example, in the case of cattle, embryos in which the nuclear phase of all cells analyzed contains 58 autosomes and 2 sex chromosomes (2n=60) are considered to be embryos having normal chromosome numbers. Embryos other than such embryos are considered to be embryos having abnormal chromosome numbers. The nuclear phase (chromosome number) of cells at the mitotic phase can be analyzed by Giemsa staining. Embryos with 2 or more cells at the mitotic phase are determined to be embryos that can be analyzed.

Condition "d2," "the time . . . confirmed to result in the expression level of 0.45 or more of an IGF2R gene relative to the expression level of an H2AFZ gene designated as 1, based on the correlation between the time from fertilization to the completion of first cleavage and the relative expression level" is as described below. The present inventors have found in a preliminary examination: that the first cleavage time of a cattle embryo correlates with the expression level of the IGF2R gene in the embryo at the blastocyst stage; and that when the first cleavage time is equal to or less than a threshold, the expression level of IGF2R in the embryo at the blastocyst stage tends to increase. Under in vitro culture conditions substantially the same as those employed for the method of the present invention, the correlation between the time from fertilization to the completion of first cleavage of an embryo and the expression level of IGF2R in the embryo at the blastocyst stage relative to the expression level of an H2AFZ gene designated as 1 can be confirmed in advance also for mammals other than cattle. To select embryos having high conception rates, selection of embryos exhibiting a time of first cleavage confirmed to result in the relative expression level of 0.45 or more of IGF2R is effective. To narrow down the number of selected embryos, selection of embryos exhibiting a time of first cleavage confirmed to result in the relative expression level of 0.50 or more is effective. To further narrow down the number of selected embryos, embryos exhibiting a time of first cleavage confirmed to result in the relative expression level of 0.60 or more can be selected.

Condition "d3," "the time . . . confirmed to result in the expression level of 0.2 or more of the IFN-tau gene in the embryo at the blastocyst stage relative to the expression level of the H2AFZ gene designated as 1, based on the correlation between the time from fertilization to the completion of first cleavage of the embryo and the relative expression level" is as described below. The present inventors have found in a preliminary examination: that the first cleavage time of a cattle embryo correlates with the expression level of an IFN-tau gene in the embryo at the blastocyst stage; and that when the first cleavage time is equal to or less than the threshold, the expression level of IFN-tau in the embryo at the blastocyst stage tends to increase. Under in vitro culture conditions substantially the same as those employed in the method of the present invention, the correlation between the time from fertilization to the completion of first cleavage of an embryo and the expression level of IFN-tau in the embryo at the blastocyst stage relative to the expression level of an H2AFZ gene designated as 1 can be confirmed in advance also for mammals other than cattle. To select embryos having high conception rates, selection of embryos exhibiting a time of first cleavage confirmed to result in the relative expression level of 0.20 or more of IFN-tau is effective. To narrow down the number of selected embryos, embryos exhibiting a time of first cleavage confirmed to result in the relative expression level of 0.25 or more can be selected. To further narrow down the number of selected embryos, embryos exhibiting a time of first cleavage confirmed to result in the relative expression level of 0.30 or more can be selected.

The expression levels of IGF2R. IFN-tau, and H2AFZ genes can be separately evaluated based on the mRNA levels (eDNA levels).

Cattle IGF2R gene (SEQ ID NO: 13), IFN-tau gene (SEQ ID NO: 14), and H2AFZ gene (SEQ ID NO: 15) are registered with GeneBank under accession numbers NM_174352.2, X65539, and NM_174809, respectively. IGF2R is a kind of imprinted gene. IFN-tau is a kind of implantation-related gene. H2AFZ is a kind of housekeeping gene to be used as an internal standard in the present invention. Homologous genes having functions substantially the same as those of the cattle IGF2R gene, IFN-tau gene, and H2AFZ gene, in an animal species other than cattle, can be specified as an IGF2R gene, an IFN-tau gene, and an H2AFZ gene, respectively, in the relevant animal species. For example, the sheep IGF2R gene, IFN-tau gene, and H2AFZ gene are genes registered with the GeneBank under accession numbers AF353513.1, NP_001095205.1, and NP_001009270.1, respectively.

Condition "d" is a condition where at least 1, preferably at least 2, and more preferably 3 conditions (d1, d2, and d3) relating to the first cleavage time is satisfied. Particularly preferably condition "d" is a condition where "d1" is satisfied, both conditions "d2" and "d3" are satisfied, or all conditions "d1," "d2," and "d3" are satisfied.

In the case of cattle embryos, to select embryos that satisfy condition "d" and thus have high conception rates, selection of embryos exhibiting a time of first cleavage of 27 hours or less is effective. To narrow down the number of selected embryos, embryos exhibiting a time of first cleavage of 26 hours or less can be selected. When the threshold of the first cleavage time is too high, the total number of selected embryos increases, low-quality embryos are included, and thus conception rates decrease. When the threshold of the first cleavage time is too low, all embryos have sufficient quality and do not differ from each other in terms of quality. However, there is a demerit that the total number of selected embryos decreases, and thus the number of embryos that can be used for implantation decreases.

The completion of first cleavage can be confirmed by observation using a microscope, for example. Embryos are observed at the threshold time point of the first cleavage time (e.g., at 27 or 26 hours after fertilization). When the completion of first cleavage is confirmed at the time point, the first cleavage time is determined to be the threshold or before. When the incompletion of first cleavage can be confirmed at the time point, the first cleavage time can be determined to be after the threshold. Embryos are observed over time, the first cleavage time is confirmed, and then the first cleavage time can be compared with the threshold.

The term "embryos at a stage after first cleavage and before second cleavage" refers to, in the case of cattle embryos, under general in vitro culture conditions, embryos at a stage 20 to 40 hours and typically 28 to 33 hours after fertilization. In the case of culture of other mammalian embryos, embryos at such a stage can be easily specified by observation. When embryogenesis is performed in advance under the same in vitro culture conditions, and the time zone (determined based on the time of fertilization) from the completion of first cleavage (by most normal embryos; preferably 70% or more, and more preferably 80% or more) to the start of second cleavage is known, embryos in the time zone can be regarded as embryos at "a stage after first cleavage and before second cleavage."

The timing of cleavage differs depending on animal species. A rough time zone is known for the animal species as stated above. However, there are individual differences and variability to some extent among animals of even the same animal species, as stated above. In the case of cattle, at a time earlier than a time point at 20 hours after fertilization, most embryos have not completed first cleavage, but at a time later than a time point at 40 hours after fertilization, most embryos have completed second cleavage (or cleavage following the second cleavage). Persons skilled in the art can appropriately select a time zone in which most embryos (preferably 70% or more and more preferably 80% or more) have completed first cleavage, and are at a stage before second cleavage. Morphological observation can be performed during such time zone so that predetermined indicators can be obtained. In the case of other mammals, a time zone in which most embryos (preferably 70% or more and more preferably 80% or more) are at "a stage after first cleavage and before second cleavage" despite variations in the timing of cleavage of individual embryos as stated above can be appropriately selected, and thus predetermined indicators in the time zone can be obtained.

The term "embryo(s) at a stage after third cleavage and before fourth cleavage" refers to, in the case of cattle embryos, embryos at a stage at 36 to 108 hours and typically at 40 to 96 hours after fertilization under general in vitro culture conditions. When other mammalian embryos are cultured, embryos at such a stage can be easily specified by observation. When embryogenesis has been performed in advance under the same in vitro culture conditions and the time zone (determined based on the time of fertilization) from the completion of third cleavage (by most normal embryos, preferably 70% or more and more preferably 80% or more) to the start of fourth cleavage is understood, embryos in the time zone can be regarded as embryos at "a stage after third cleavage and before fourth cleavage." Although the timing of cleavage is varied among individual embryos of every mammalian species, a time zone in which most embryos (preferably 70% or more and more preferably 80% or more) are at "a stage after third cleavage and before fourth cleavage" can be appropriately selected and predetermined indicators in the time zone can be obtained.

The term "embryo(s) at the early blastocyst stage, the blastocyst stage, or the expanded blastocyst stage" refers to embryos at any one of developmental stages including the early blastocyst stage, the blastocyst stage, and then the expanded blastocyst stage. In the case of cattle embryos, under general in vitro culture conditions, the term refers to embryos at a stage at 120 to 216 hours, and typically 144 to 192 hours after fertilization. When other mammalian embryos are cultured, embryos at such a stage can be easily specified by observation. When embryogenesis has been performed in advance under the same in vitro culture conditions, and the time zone (determined based on the time of fertilization) wherein most normal embryos (preferably 70% or more and more preferably 80% or more) are at any one of developmental stages from the early blastocyst stage to the expanded blastocyst stage is understood, embryos in the time zone can be regarded as embryos at "the early blastocyst stage, the blastocyst stage, or the expanded blastocyst stage." Although the growth degree is varied among individual embryos of every mammalian species, a time zone in which most embryos (preferably 70% or more and more preferably 80% or more) are at "the early blastocyst stage, the blastocyst stage, or the expanded blastocyst stage" can be appropriately selected, and thus predetermined indicators in the time zone can be obtained.

The terms "early blastocyst," "blastocyst." and "expanded blastocyst" are as defined in Robertson I, Nelson RE (1998) Certification and identification of the embryo. In: D. A. Stringfellow and S. M. Seidel, Editors, Manual of the international embryo transfer society, IETS, Savoy, Ill. 103-116 and thus can be clearly understood by persons skilled in the art. The terms are as specifically explained below for reference.

The term "early blastocyst" refers to an embryo at a stage when a blastocoele is observed under a microscope. An early blastocyst exhibits a ring-like form.

When an early blastocyst grows, the separation of cytotrophoblasts proceeds, and darkening of inner cell masses to the extent that clearer differentiation between the two becomes possible, a "blastocyst" results in. A blastocoele broadly expands within the perivitelline space and then almost fills the perivitelline space.

The term "expanded blastocyst" refers to an embryo after a blastocyst grows, a blastocoele expands significantly, and then the whole size increases (about 1.2 to 1.5 times the size of an embryo at a stage up to the blastocyst stage) as well as the thickness of the zona pellucida thins to about ⅓ the original thickness.

"the amount of oxygen consumed at the early blastocyst stage, the blastocyst stage, or the expanded blastocyst stage is confirmed to result in a probability of 50% or more that the embryo will reach the hatched blastocyst stage, based on the correlation between the amount of oxygen consumed by the embryo at the early blastocyst stage, the blastocyst stage, or the expanded blastocyst stage and the probability" is as explained below. The present inventors have found in a preliminary examination (Experiment 2): that the amount of oxygen consumed by a cattle embryo at the early blastocyst stage, the blastocyst stage, or the expanded blastocyst stage correlates with a probability that the embryo will reach the hatched blastocyst stage; and that when the amount of oxygen consumed is equal to or higher than a threshold, a probability that the embryo will reach the hatched blastocyst stage tends to drastically increase. Under in vitro culture conditions substantially the same as those used for the method of the present invention, the correlation between the amount of oxygen consumed by an embryo at the early blastocyst stage, the blastocyst stage, or the expanded blastocyst stage and a probability that the embryo will reach the hatched blastocyst stage can be confirmed in advance also for mammals other than cattle. To select embryos having high conception rates, selection of embryos having the amount (of oxygen consumed) confirmed to result in a probability of 50% or more is effective. To further narrow down the number of selected embryos, embryos having the amount (of oxygen consumed) confirmed to result in a probability of 85% or more can be selected. In the case of cattle embryos, to select embryos having high conception rates, the selection of embryos exhibiting the amount of oxygen consumed of $0.91 \times 10^{-14}$ mol $s^{-1}$ or more per single embryo at the early blastocyst stage, the blastocyst stage, or the expanded blastocyst stage is effective. To further narrow down the number of selected embryos, embryos exhibiting the amount of oxygen consumed of $1.11 \times 10^{-14}$ mol $s^{-1}$ or more per single embryo can be selected. When the value of the indicator (the amount of oxygen consumed) for selection is too low, the total number of selected embryos increases, low-quality embryos are unexpectedly included, and thus the conception rates decrease. When the value of the indicator (the amount of oxygen consumed) for selection is too high, all embryos have sufficient quality and do not differ from each other in terms of quality. However, there is a demerit that the total number of selected embryos decreases and thus the number of embryos that can be used for implantation decreases.

The amount of oxygen consumed per single embryo can be measured noninvasively using a commercially available apparatus such as an SECM system (HV-405; HOKUTO DENKO Corporation). The amount of oxygen consumed is preferably measured in a medium for respiration assay (e.g., ERAM-2 (embryo respiration assay medium-2, Research Institute for the Functional Peptides)) under temperature conditions substantially the same as those of in vitro culture conditions.

A first aspect of the present invention is a method for selecting a mammalian embryo prepared by in vitro culture from a fertilized egg, comprising a step of selecting an embryo by obtaining at least 2 and preferably at least 3 of the 4 above indicators, and more preferably all 4 indicators, for evaluation and then selecting an embryo based on the evaluation results, in the selection step, embryos satisfying at least 2, preferably at least 3, and more preferably all 4 conditions ("a" to "d") above are selected. Embryos to be selected herein are cultured in vitro preferably to the early blastocyst stage, the blastocyst stage, or the expanded blastocyst stage. When 2 or more indicators from among the time from fertilization to the completion of first cleavage, the morphology at a stage after first cleavage and before second cleavage, and the morphology at a stage after third cleavage and before fourth cleavage are used, any embryos cultured in vitro to the 2-cell stage (specifically, after the completion of first cleavage), 8-cell stage (specifically, after completion of third cleavage), or any developmental stage following the 2-cell or 8-cell stage may be used. The person who performs the selection method may be the same as or differ from the person who performs the method for producing embryos by in vitro culture.

A second aspect of the present invention is a method for producing an embryo from a mammalian fertilized egg by in vitro culture, comprising the above selection step. Embryos to be used herein are cultured in vitro to preferably the early blastocyst stage, the blastocyst stage, or the expanded blastocyst stage. When 2 or more indicators of the time from fertilization to the completion of first cleavage, the morphology at a stage after first cleavage and before second cleavage, and the morphology at a stage after third cleavage and before fourth cleavage are used, any embryos cultured in vitro to the 2-cell stage (specifically, after the completion of first cleavage), 8-cell stage (specifically, after the completion of third cleavage), or any developmental stage following the 2-cell or 8-cell stage may be used, and then can be subjected to applications thereafter.

A third aspect of the present invention is a method for producing an individual mammal, comprising a step of implanting an embryo selected by the above selection method or an embryo produced by the above production method into an individual female for conception. In general, an individual female (recipient) to be subjected to implantation is in a pseudo-pregnancy state, and an embryo is implanted into the uterine horn, oviduct, or the like of the individual female. After conception, a step of obtaining progeny and a step of obtaining individual animals by growing progeny can be performed by conventional methods.

<Embryo Selection Apparatus, Embryo Selection System, and Method for Selecting Embryos>

The present invention also relates to an embryo selection apparatus for selecting mammalian candidate embryos cultured in vitro from fertilized eggs, with which the method of the present invention can be realized.

The embryo selection apparatus of the present invention comprises a determination unit and an analysis unit, wherein: the determination unit determines whether or not M pieces of (where M is the number 2, 3, or 4) information from among the $1^{st}$ indicator information to the $4^{th}$ indicator information for an obtained candidate embryo satisfy selection criteria specified in advance; and the analysis unit concludes that the candidate embryo satisfying N (where N is the number 2 or more and M or less) or more conditions as determined in the above determination unit should be selected. Specific numbers for M and N can be appropriately determined in accordance with purpose. The larger the value of N, the higher the possibility of selecting embryos having high conception rates, but the smaller the number of embryos to be used for implantation.

Hereinafter, an embodiment of the embryo selection apparatus of the present invention in a case where M=4 and N=2 to 4 is explained with reference to FIGS. 6 to 8; an embodiment of the embryo selection apparatus of the present invention in a case where M=3 and N=2 to 3 is explained with reference to FIGS. 9, 11, and 12: and the embryo selection apparatus of the present invention in a case where M=2 and N=2 is explained with reference to FIG. 10: but the scope of the present invention is not limited to embodiments shown in these Figures.

Figure 6:
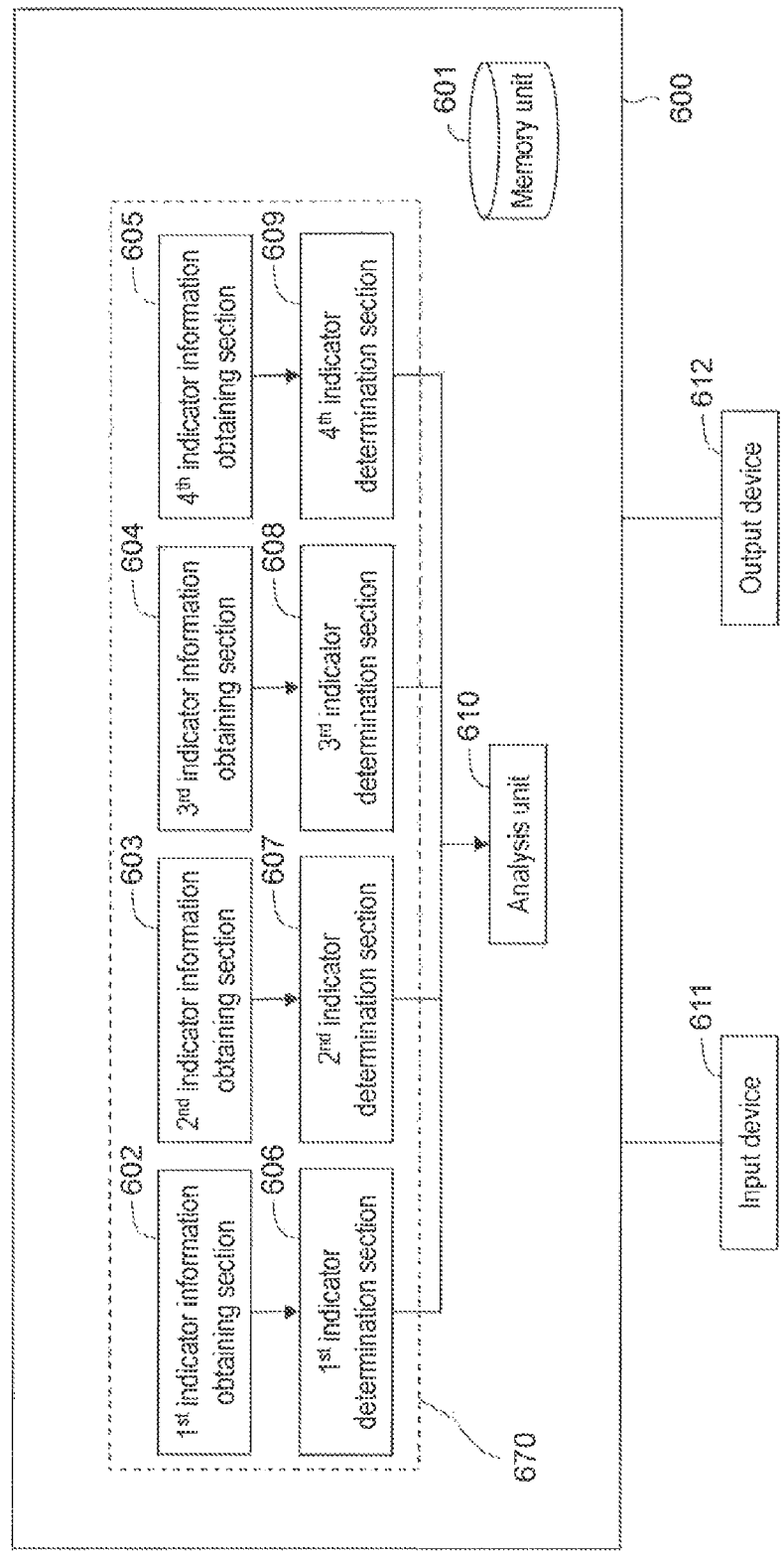
FIG. 6 is a schematic block diagram showing an embodiment of the embryo selection apparatus of the present invention in a case where M=4 and N=2 to 4.

FIG. 6 is a schematic block diagram showing the configuration of functions of an embryo selection apparatus (600) that is one embodiment of the embryo selection apparatus (M=4 and N=2 to 4) of the present invention. The embryo selection apparatus (600) comprises at least a determination unit (670) and an analysis unit (610), and further comprises a memory unit (601), as necessary. The memory unit (601) may be connected to other parts of the embryo selection apparatus (600) via a network so that data can be stored and read. The embryo selection apparatus (600) can be composed of information processing equipment such as a computer. An input device (611), an output device (612), and the like are connected to the embryo selection apparatus (600), as necessary.

The determination unit (670) comprises at least a $1^{st}$ indicator determination section (606), a $2^{nd}$ indicator determination section (607), a $3^{rd}$ indicator determination section (608), and a $4^{th}$ indicator determination section (609), and generally further comprises a $1^{st}$ indicator information obtaining section (602), a $2^{nd}$ indicator information obtaining section (603), a $3^{rd}$ indicator information obtaining section (604), and a $4^{th}$ indicator information obtaining section (605).

The memory unit (601) stores the $1^{st}$ indicator selection criterion concerning the time from fertilization to the completion of first cleavage, the $2^{nd}$ indicator selection criterion concerning the morphology at a stage after first cleavage and before second cleavage, the $3^{rd}$ indicator selection criterion concerning the morphology at a stage after third cleavage and before fourth cleavage, and the $4^{th}$ indicator selection criterion concerning the amount of oxygen consumed at the early blastocyst stage, the blastocyst stage, or the expanded blastocyst stage, as well as, among these conditions, information concerning the number (N) of conditions that should be satisfied by embryos to be selected. These pieces of information are stored in advance in the memory unit (601).

A specific example of the "$1^{st}$ indicator selection criterion concerning the time from fertilization to the completion of first cleavage" is condition "d" above. When the embryo selection apparatus (600) is used for selecting cattle embryos, condition "d" is preferably a condition such that "the time from fertilization to the completion of first cleavage is 27 hours or less," or a condition such that "the time from fertilization to the completion of first cleavage is 26 hours or less."

A specific example of the "$2^{nd}$ indicator selection criterion concerning the morphology at a stage after first cleavage and before second cleavage" is condition "a" above, A specific example of the "$3^{rd}$ indicator selection criterion concerning the morphology at a stage after third cleavage and before fourth cleavage" is condition "b" above.

A specific example of the "$4^{th}$ indicator selection criterion concerning the amount of oxygen consumed at the early blastocyst stage, the blastocyst stage, or the expanded blastocyst stage" is condition "c" above. When the embryo selection apparatus (600) is used for selecting cattle embryos, condition "c" is preferably a condition such that "the amount of oxygen consumed at the early blastocyst stage, the blastocyst stage, or the expanded blastocyst stage is $0.91 \times 10^{-14}$ mol s$^{-1}$ or more per single embryo," or a condition such that "the amount of oxygen consumed at the early blastocyst stage, the blastocyst stage, or the expanded blastocyst stage is $1.11 \times 10^{-14}$ mol s$^{-1}$ or more per single embryo."

The $1^{st}$ indicator information obtaining section (602) obtains the $1^{st}$ indicator information concerning the time from fertilization to the completion of first cleavage of a candidate embryo, and then inputs the information into the $1^{st}$ indicator determination section (606). The $1^{st}$ indicator information may be specifically data indicating the time from fertilization to the completion of first cleavage of the candidate embryo (the first cleavage time), or data indicating the presence or the absence of the completion of first cleavage at the threshold time point of the first cleavage time specified in the above $1^{st}$ indicator selection criterion. The $1^{st}$ indicator information may be input by a user to the $1^{st}$ indicator information obtaining section (602) via the input device (611), or input from a 1$^{st}$ image analysis section as described later.

The 1$^{st}$ indicator determination section (606) determines whether or not the 1$^{st}$ indicator information of a candidate embryo satisfies the 1$^{st}$ indicator selection criterion stored in a memory device (601). Specifically, when the first cleavage time of the candidate embryo is equal to or less than the threshold of the first cleavage time specified in the 1$^{st}$ indicator selection criterion (or, when the completion of first cleavage of the candidate embryo is confirmed at the threshold time point of the first cleavage time), it is determined that the 1$^{st}$ indicator selection criterion is satisfied. When the first cleavage time of the candidate embryo is larger than the threshold of the first cleavage time specified in the 1$^{st}$ indicator selection criterion (or, when the completion of first cleavage of the candidate embryo is not confirmed at the threshold time point of the first cleavage time), it is determined that the 1$^{st}$ indicator selection criterion is not satisfied.

The 2$^{nd}$ indicator information obtaining section (603) obtains the 2$^{nd}$ indicator information concerning the morphology of a candidate embryo at a stage after first cleavage and before second cleavage, and then inputs the information into the 2$^{nd}$ indicator determination section (607). The 2$^{nd}$ indicator information specifically contains data indicating the number of blastomeres of the candidate embryo at a stage after first cleavage and before second cleavage, and data indicating the presence or the absence of fragmentation. The 2$^{nd}$ indicator information may be input by a user to the 2$^{nd}$ indicator information obtaining section (603) via the input device (611), or input from a 2$^{nd}$ image analysis section as described later.

The 2$^{nd}$ indicator determination section (607) determines whether or not the 2$^{nd}$ indicator information of a candidate embryo satisfies the 2$^{nd}$ indicator selection criterion stored in the memory device (601). Specifically, when the number of blastomeres of the candidate embryo at a stage after first cleavage and before second cleavage is within the range of the number of blastomeres specified in the 2$^{nd}$ indicator selection criterion and no fragmentation is observed at the same stage, it is determined that the 2$^{nd}$ indicator selection criterion is satisfied. In other cases, it is determined that the 2$^{nd}$ indicator selection criterion is not satisfied.

The 3$^{rd}$ indicator information obtaining section (604) obtains the 3$^{rd}$ indicator information concerning the morphology of a candidate embryo at a stage after third cleavage and before fourth cleavage, and then inputs the information into the 3$^{rd}$ indicator determination section (608). The 3$^{rd}$ indicator information specifically contains data indicating the number of blastomeres of the candidate embryo at a stage after third cleavage and before fourth cleavage and data indicating the presence or the absence of fragmentation. The 3$^{rd}$ indicator information may be input by a user to the 3$^{rd}$ indicator information obtaining section (604) via the input device (611) or input from a 3$^{rd}$ image analysis section as described below.

The 3$^{rd}$ indicator determination section (608) determines whether or not the 3$^{rd}$ indicator information of a candidate embryo satisfies the 3$^{rd}$ indicator selection criterion stored in the memory device (601). Specifically, when the number of blastomeres of the candidate embryo at a stage after third cleavage and before fourth cleavage is within the range of the number of blastomeres specified in the 3$^{rd}$ indicator selection criterion, and no fragmentation is observed at the same stage, it is determined that the 3$^{rd}$ indicator selection criterion is satisfied. In other cases, it is determined that the 3$^{rd}$ indicator selection criterion is not satisfied.

The 4$^{th}$ indicator information obtaining section (605) obtains the 4$^{th}$ indicator information concerning the amount of oxygen consumed by a candidate embryo at the early blastocyst stage, the blastocyst stage, or the expanded blastocyst stage and then inputs the information into the 4$^{th}$ indicator determination section (609). The 4$^{th}$ indicator information specifically contains data indicating the amount of oxygen consumed by the candidate embryo at the early blastocyst stage, the blastocyst stage, or the expanded blastocyst stage. The 4$^{th}$ indicator information may be input by a user to the 4$^{th}$ indicator information obtaining section (605) via the input device (611), or input from a device for measuring the amount of oxygen consumed as described below.

The 4$^{th}$ indicator determination section (609) determines whether or not the 4$^{th}$ indicator information of a candidate embryo satisfies the 4$^{th}$ indicator selection criterion stored in the memory device (601). Specifically, when the amount of oxygen consumed by the candidate embryo at the early blastocyst stage, the blastocyst stage, or the expanded blastocyst stage is equal to or higher than the threshold of the amount of oxygen consumed specified in the 4$^{th}$ indicator selection criterion, it is determined that the 4$^{th}$ indicator selection criterion is satisfied. When the amount of oxygen consumed by the candidate embryo is lower than the threshold, it is determined that the 4$^{th}$ indicator selection criterion is not satisfied.

The analysis unit (610) determines, based on the results of the 1$^{st}$ indicator determination section (606), the 2$^{nd}$ indicator determination section (607), the 3$^{rd}$ indicator determination section (608), and the 4$^{th}$ indicator determination section (609), whether or not the number of conditions (from among the 1$^{st}$ indicator selection criterion, the 2$^{nd}$ indicator selection criterion, the 3$^{rd}$ indicator selection criterion, and the 4$^{th}$ indicator selection criterion) that are satisfied by a candidate embryo is equal to or higher than the number (N) stored. When the number is equal to or higher than N, the analysis unit (610) concludes that the candidate embryo should be selected ("OK (good)"). When the number is less than N, the analysis unit (610) concludes that the candidate embryo should not be selected ("NG (bad)").

The analysis unit (610) generates analysis results. The generated analysis results can be output via the output device (612). The output device (612) may be of any form, such as a display or a printer. Analysis results may be stored in the memory unit (601). Analysis results to be output or stored can contain the following items, for example:

Information for specifying candidate embryos (information indicating the positions with coordinates or the like)
OK/NG (analysis results)
1$^{st}$ indicator information
2$^{nd}$ indicator information
3$^{rd}$ indicator information
4$^{th}$ indicator information
Determination results based on the 1$^{st}$ indicator information
Determination results based on the 2$^{nd}$ indicator information
Determination results based on the 3$^{rd}$ indicator information
Determination results based on the 4$^{th}$ indicator information The 1$^{st}$ indicator information, the 2$^{nd}$ indicator information, and the 3$^{rd}$ indicator information to be input to the embryo selection apparatus of the present invention can be generated as a result of judgment made by a user or image processing technology based on the images of candidate embryos taken at predetermined stages.

The embryo selection apparatus of the present invention can further comprise a configuration for extracting images to be referred to for generation of the $1^{st}$ indicator information, the $2^{nd}$ indicator information, and/or the $3^{rd}$ indicator information. Examples of an embodiment of the embryo selection apparatus comprising the configuration are shown in FIG. 7 and FIG. 8. Explanation for the configurations shown with symbols 701 to 712, 770, 801 to 812, and 870 in FIG. 7 and FIG. 8 is omitted since they have features similar to those of the configuration shown with symbols 601 to 612 and 670 in FIG. 6.

Figure 7:
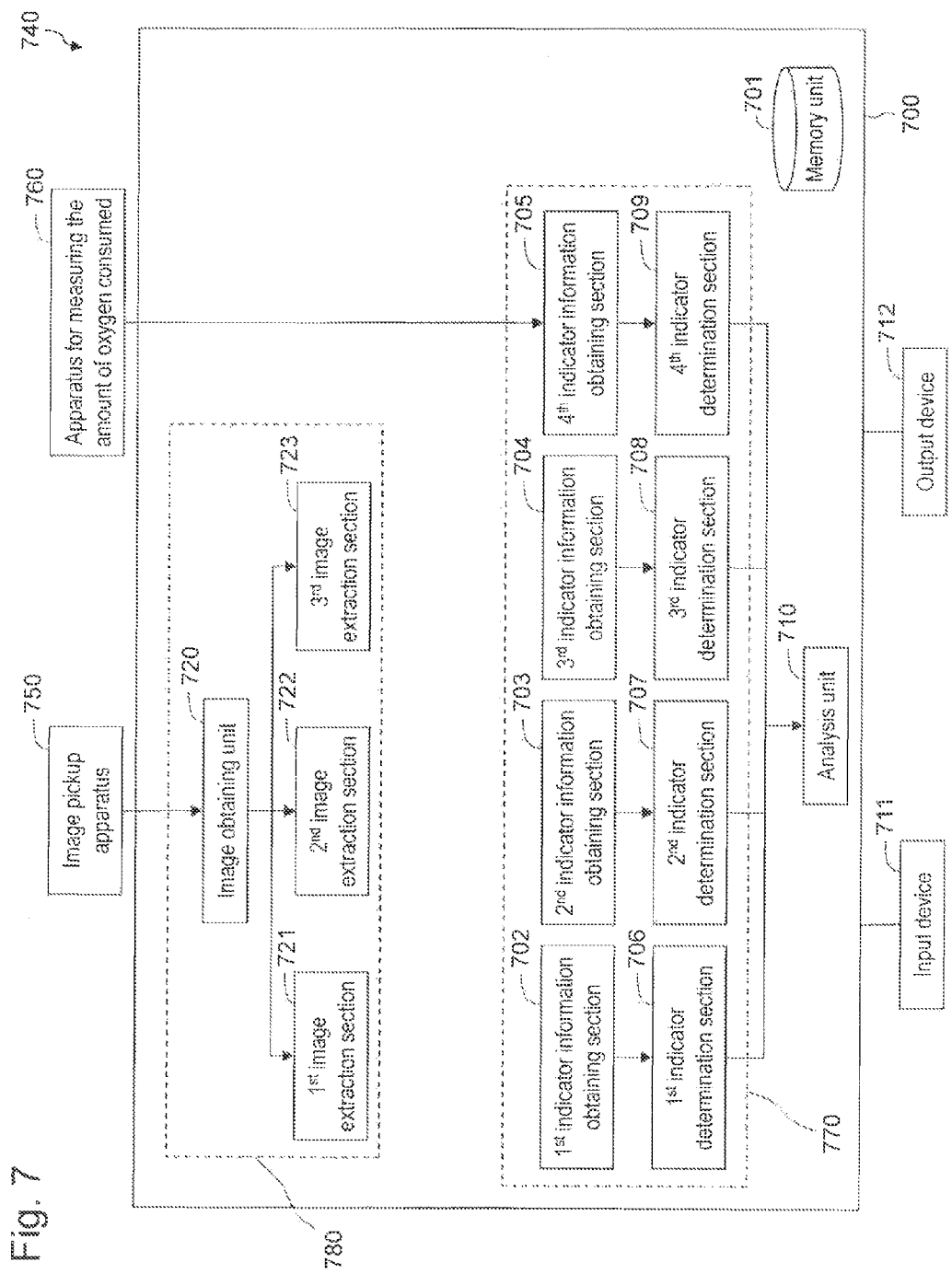
FIG. 7 is a schematic block diagram showing an embodiment of the embryo selection apparatus and the embryo selection system of the present invention in a case where M=4 and N=2 to 4.

An embryo selection apparatus (700) shown in FIG. 7 comprises an image extraction unit (780) for extracting images to be referred to for generation of the $1^{st}$ indicator information, the $2^{nd}$ indicator information, and the $3^{rd}$ indicator information. The image extraction unit (780) comprises at least a $1^{st}$ image extraction section (721), a $2^{nd}$ image extraction section (722), and a $3^{rd}$ image extraction section (723), and generally further comprises an image obtaining unit (720).

The image obtaining unit (720) obtains the image data of candidate embryos taken by an image pickup apparatus such as a video camera, and then it inputs the information into the $1^{st}$ image extraction section (721), the $2^{nd}$ image extraction section (722), and the $3^{rd}$ image extraction section (723). Images may be dynamic images or static images.

The $1^{st}$ image extraction section (721) extracts: the images of candidate embryos at the threshold time point of the time from fertilization to the completion of first cleavage specified in the $1^{st}$ indicator selection criterion; or images with which the time point of the completion of first cleavage can be confirmed, from the obtained images of the candidate embryos. The $1^{st}$ image extraction section (721) can refer the information of thresholds stored in the memory unit (701), as necessary. The thus extracted images can be output by the output device (712) as images that can be visually evaluated by a user. A user can generate the $1^{st}$ indicator information based on the images extracted by the $1^{st}$ image extraction section (721) through visual evaluation, and then input the information into a $1^{st}$ indicator information obtaining section (702) via an input device (711).

The $2^{nd}$ image extraction section (722) extracts an image at a stage after first cleavage and before second cleavage from the thus obtained images of candidate embryos. The information of candidate embryos concerning the time corresponding to "stage after first cleavage and before second cleavage" can be stored in the memory unit (701). The $2^{nd}$ image extraction section (722) can refer the information concerning the time, as necessary. The extracted image can be output by the output device (712) as an image that can be visually evaluated by a user. The user generates the $2^{nd}$ indicator information based on the image extracted from the $2^{nd}$ image extraction section (722) through visual evaluation, and then can input the information into a $2^{nd}$ indicator information obtaining section (703) via the input device (711).

The $3^{rd}$ image extraction section (723) extracts an image at a stage after third cleavage and before fourth cleavage from the obtained images of candidate embryos. The information of the candidate embryos concerning the time corresponding to "stage after third cleavage and before fourth cleavage" can be stored in the memory unit (701). The $3^{rd}$ image extraction section (723) can refer to the information concerning the time, as necessary. The thus extracted image can be output by the output device (712) as an image that can be visually evaluated by a user. A user can generate the $3^{rd}$ indicator information based on the image extracted by the $3^{rd}$ image extraction section (723) through visual evaluation, and then can input the information into a $3^{rd}$ indicator information obtaining section (704) via the input device (711).

Generation of the $1^{st}$ indicator information, the $2^{nd}$ indicator information, and the $3^{rd}$ indicator information based on images can also be automatically executed using image analytical processing software or the like. An example of the embodiment is shown in FIG. 8. In FIG. 8, a configuration shown with symbols 820 to 823 and 880 has features similar to that shown with symbols 720 to 723 and 780 in FIG. 7. An embryo determination device (800) further comprises an image analysis unit (890). The image analysis unit (890) performs image analytical processing based on an image extracted at the image extraction unit (880), so as to generate the $1^{st}$ indicator information, the $2^{nd}$ indicator information, and/or the $3^{st}$ indicator information, and then inputs the information into the determination unit (870).

The image analysis unit (890) comprises a $1^{st}$ image analysis section (831), a $2^{nd}$ image analysis section (832), and a $3^{rd}$ image analysis section (833). Images extracted from a $1^{st}$ image extraction section (821), a $2^{nd}$ image extraction section (822), and a $3^{rd}$ image extraction section (823) are separately input into the $1^{st}$ image analysis section (831), the $2^{nd}$ image analysis section (832), and the $3^{rd}$ image analysis section (833). The $1^{st}$ image analysis section (831), the $2^{nd}$ image analysis section (832), and the $3^{rd}$ image analysis section (833) separately generate the $1^{st}$ indicator information, the $2^{nd}$ indicator information, and the $3^{rd}$ indicator information by image analytical processing, and then input the information into a $1^{st}$ indicator information obtaining section (802), a $2^{nd}$ indicator information obtaining section (803), and a $3^{rd}$ indicator information obtaining section (804). Before inputting of the $1^{st}$ indicator information, the $2^{nd}$ indicator information, and the $3^{rd}$ indicator information generated by image analytical processing into the $1^{st}$ indicator information obtaining section (802), the $2^{nd}$ indicator information obtaining section (803), and the $3^{rd}$ indicator information obtaining section (804), each piece of indicator information is output to the output device (812). A user verifies the validity of the each piece of indicator information through comparison with extracted images output to the output device (812) from the $1^{st}$ image extraction section (821), the $2^{nd}$ image extraction section (822), and the $3^{rd}$ image extraction section (823). When determined to be valid, the each piece of indicator information is input to the $1^{st}$ indicator information obtaining section (802), the $2^{nd}$ indicator information obtaining section (803), and the $3^{rd}$ indicator information obtaining section (804). When determined to be invalid, as explained for the embryo selection apparatus (700), it may also be configured so that corrected indicator information generated by a user is input to the $1^{st}$ indicator information obtaining section (802), the $2^{nd}$ indicator information obtaining section (803), and the $3^{rd}$ indicator information obtaining section (804) via the input device (811).

The embryo selection apparatus of the present invention is combined with an image pickup apparatus and an apparatus for measuring the amount of oxygen consumed, so that an embryo selection system for selecting mammalian candidate embryos prepared by in vitro culture from fertilized eggs can be configured. The embryo selection systems (740, 840) shown in FIG. 7 and FIG. 8 are examples of the embodiment.

The embryo selection system (740, 840) comprises at least an embryo selection apparatus (700, 800), an image pickup apparatus (750, 850), and the apparatus for measuring the amount of oxygen consumed (760, 860).

The image pickup apparatus (750, 850) takes images of candidate embryos and then outputs the thus taken images to the image obtaining units (720, 820). The image pickup apparatus (750, 850) is not particularly limited, as long as it is combined with a microscopic objective lens as necessary and can take dynamic images or static images of candidate embryos during an vitro culture. A specific example thereof is a digital video camera.

The apparatus for measuring the amount of oxygen consumed (760, 860) measures the amount of oxygen consumed by mammalian candidate embryos (prepared by in vitro culture from fertilized eggs) at the early blastocyst stage, the blastocyst stage, or the expanded blastocyst stage, and then outputs the measured amount of oxygen consumed to a $4^{th}$ indicator information obtaining section (705, 805). The apparatus for measuring the amount of oxygen consumed (760, 860) is not particularly limited. Specifically, an apparatus described above capable of measuring the amount of oxygen consumed per single embryo can be used.

Figure 9:
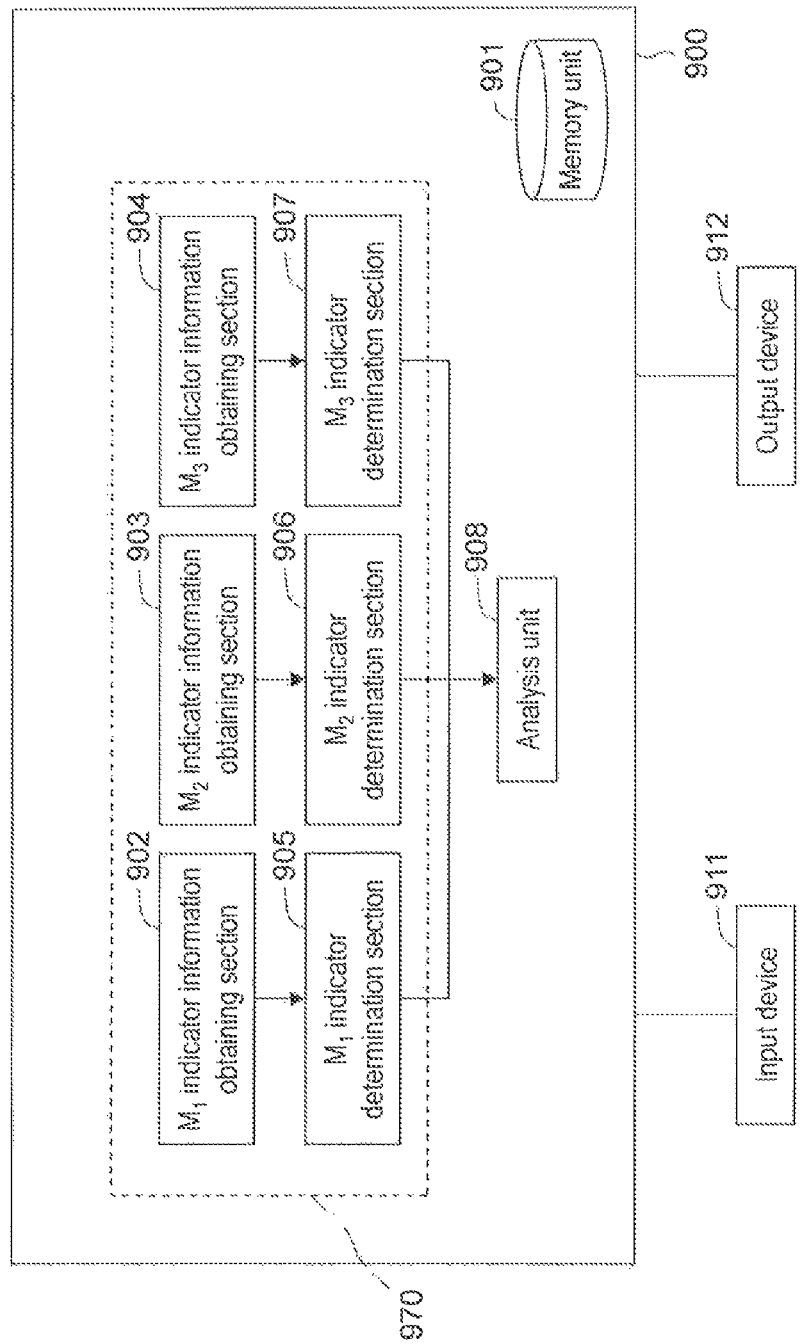
FIG. 9 is a schematic block diagram showing an embodiment of the embryo selection apparatus of the present invention in a case where M=3 and N=2 to 3.

FIG. 9 is a schematic block diagram showing the functional configuration of an embryo selection apparatus (900) when M is 3. A determination unit (970) comprises three sections: an $M_1$ indicator determination section (905), an $M_2$ indicator determination section (906); and an $M_3$ indicator determination section (907), arbitrarily selected from the $1^{st}$ indicator determination section (606), the $2^{nd}$ indicator determination section (607), the $3^{rd}$ indicator determination section (608), and the $4^{th}$ indicator determination section (609) explained with reference to FIG. 6. Here, $M_1$, $M_2$, and $M_3$ are integers selected mutually exclusively from 1, 2, 3, and 4. In a preferred embodiment of the embryo selection apparatus (900). $M_1$. $M_2$, and $M_3$ are 2, 3, and 4, respectively.

Figure 10:
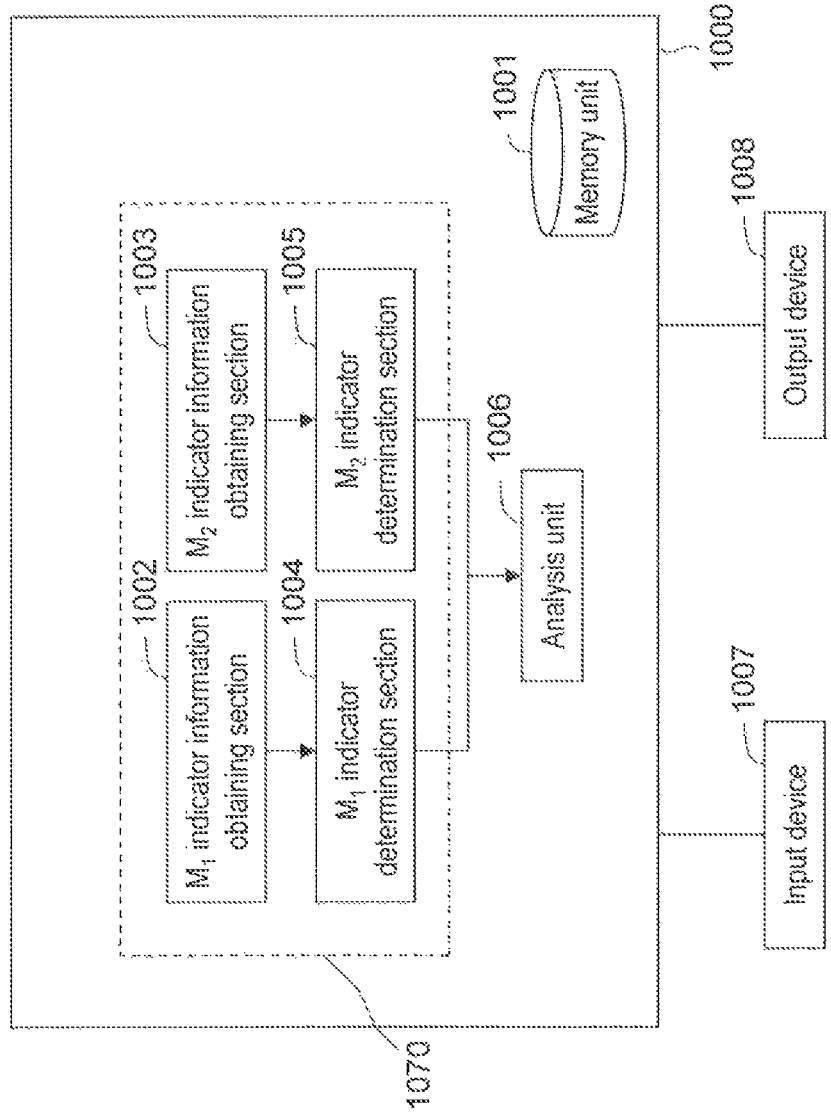
FIG. 10 is a schematic block diagram showing an embodiment of the embryo selection apparatus of the present invention in a case where M=2 and N=2.

FIG. 10 is a schematic block diagram showing the functional configuration of an embryo selection apparatus (1000) when M is 2. A determination unit (1070) comprises two sections: a $M_1$ indicator determination section (1004); and a $M_2$ indicator determination section (1005), arbitrarily selected from the $1^{st}$ indicator determination section (606), the $2^{nd}$ indicator determination section (607), the $3^{rd}$ indicator determination section (608), and the $4^{th}$ indicator determination section (609) explained with reference to FIG. 6. Here, $M_1$ and $M_2$ are integers selected mutually exclusively from 1, 2, 3, and 4 and are preferably integers selected from 2, 3, and 4.

Figure 11:
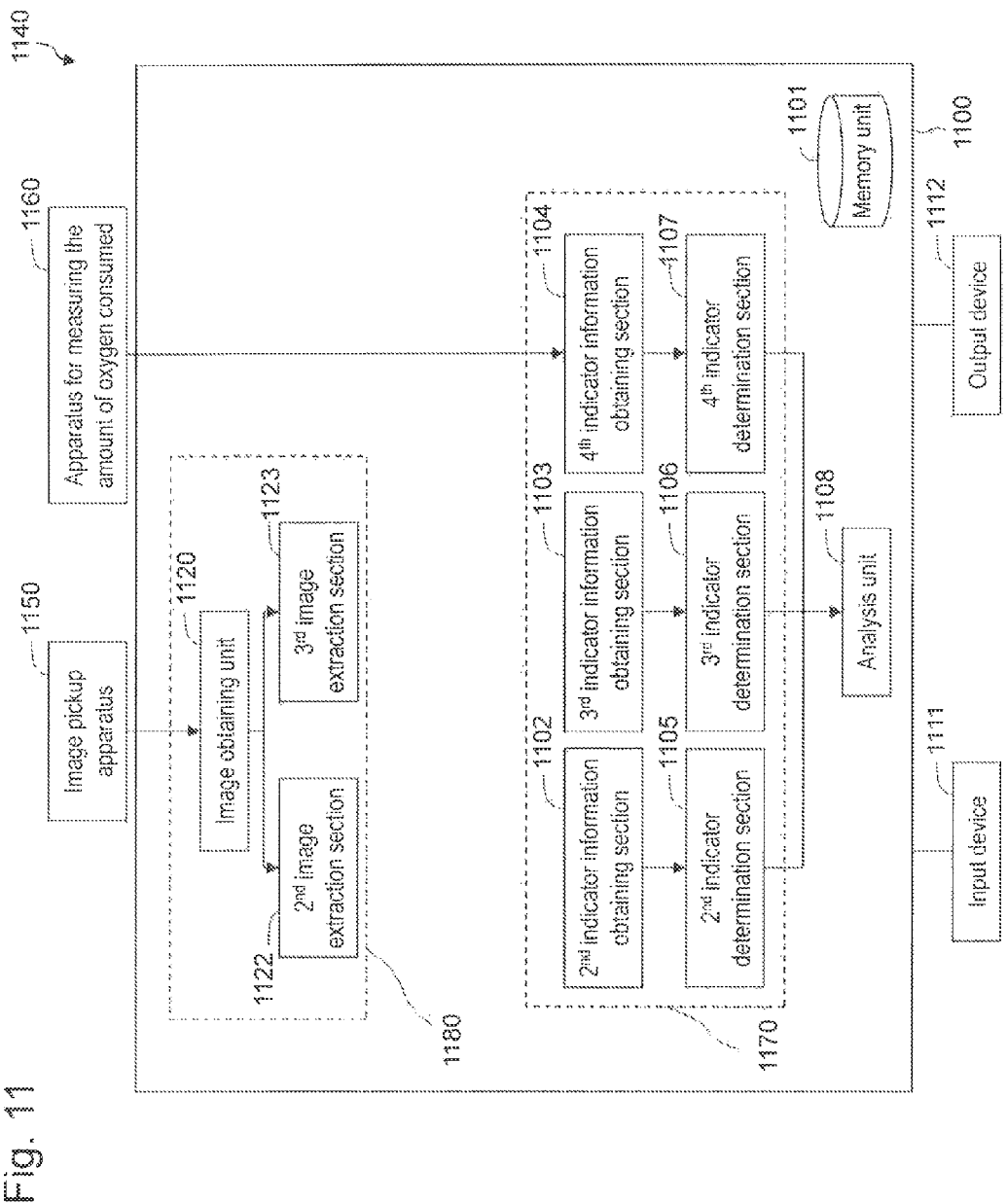
FIG. 11 is a schematic block diagram showing an embodiment of the embryo selection apparatus and the embryo selection system of the present invention in a case where M=3 and N=2 to 3.

FIG. 11 shows an embryo selection apparatus (1100) and an embryo selection system (1140) that are embodiments of the embryo selection apparatus (700) and the embryo selection system (740) shown in FIG. 7 in a case where M=3.

Figure 8:
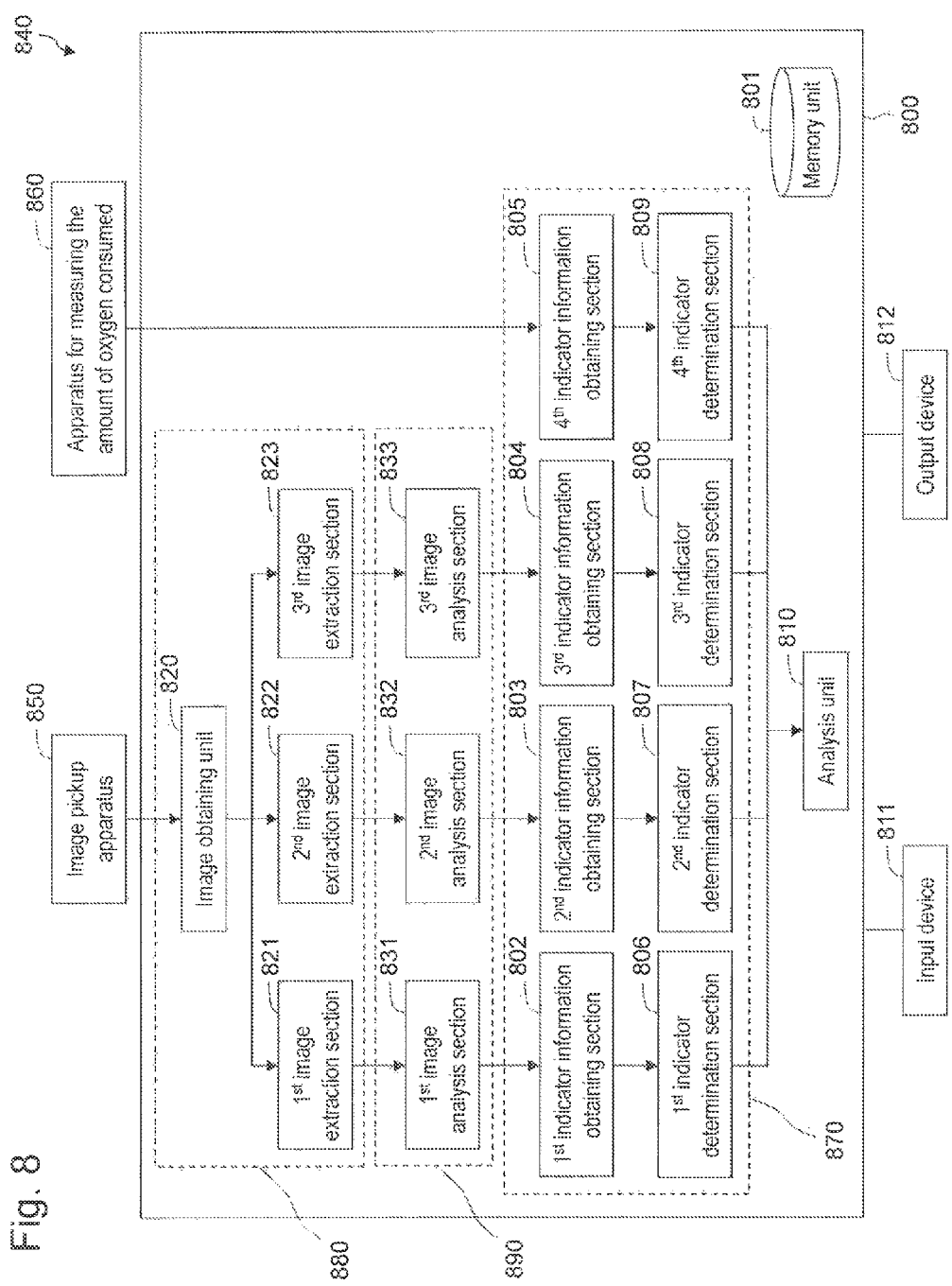
FIG. 8 is a schematic block diagram showing an embodiment of the embryo selection apparatus and the embryo selection system of the present invention in a case where M=4 and N=2 to 4.
Figure 12:
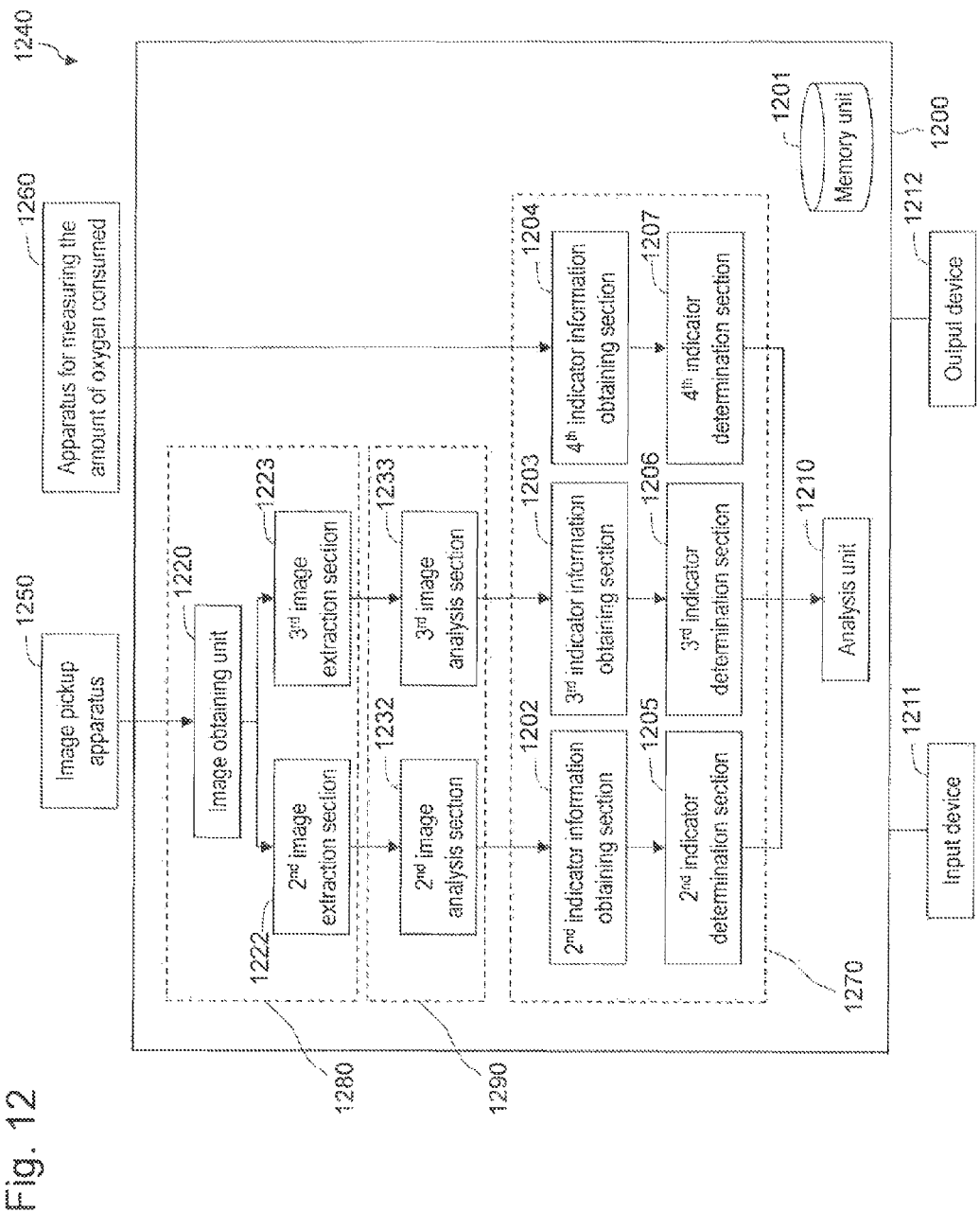
FIG. 12 is a schematic block diagram showing an embodiment of the embryo selection apparatus and the embryo selection system of the present invention in a case where M=3 and N=2 to 3.

FIG. 12 shows an embryo selection apparatus (1200) and an embryo selection system (1240) that are embodiments of the embryo selection apparatus (800) and the embryo selection system (840) shown in FIG. 8 in a case where M=3.

The embryo selection apparatus (1100, 1200) is an example of the embryo selection apparatus (900) in a case where $M_1$=2, $M_2$=3, and $M_3$=4, but the example thereof is not limited thereto.

A method for selecting embryos using the embryo selection apparatus of the present invention is explained with reference to flow charts shown in FIG. 13 to FIG. 22. For convenience, the following explanation is given separately referring the embryo determination apparatuses (600, 900, 1000) as typical examples of embryo determination apparatuses in a case where M=4, M=3, and M=2.

In addition, in the following explanations, the term "$M_1 \ldots M_M$" refers to integers selected mutually exclusively from the group consisting of integers of 1 . . . M (M is an integer of 2, 3, or 4).

Figure 20:
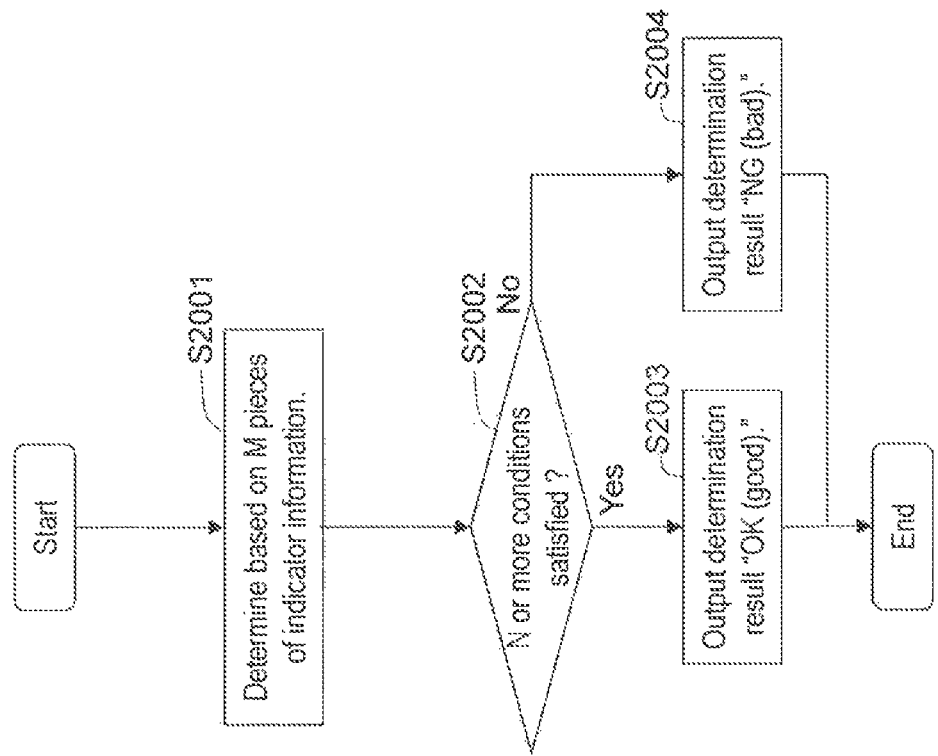
FIG. 20 is a flow chart showing the outline of the method for selecting embryos using the embryo selection apparatus of the present invention.

FIG. 20 shows the outline of the method for selecting embryos using the embryo determination apparatus (600, 900, 1000). The determination unit (670, 970, 1070) determines (S2001) whether or not the thus obtained $M_1$ indicator information to the $M_M$ indicator information concerning candidate embryos satisfy the corresponding indicator selection criteria. Next, the analysis unit (610, 908, 1006) analyzes (S2002) whether or not the number of criteria determined to be satisfied in S2001 is N or more. When N or more criteria are satisfied, the analysis unit outputs (S2003) the determination result "OK (good)," indicating that the embryo should be selected. When the number of criteria determined to be satisfied is less than N, the analysis unit outputs (S2004) the determination result "NG (bad)," indicating that the embryo should not be selected and thus completes the analysis.

Figure 21:
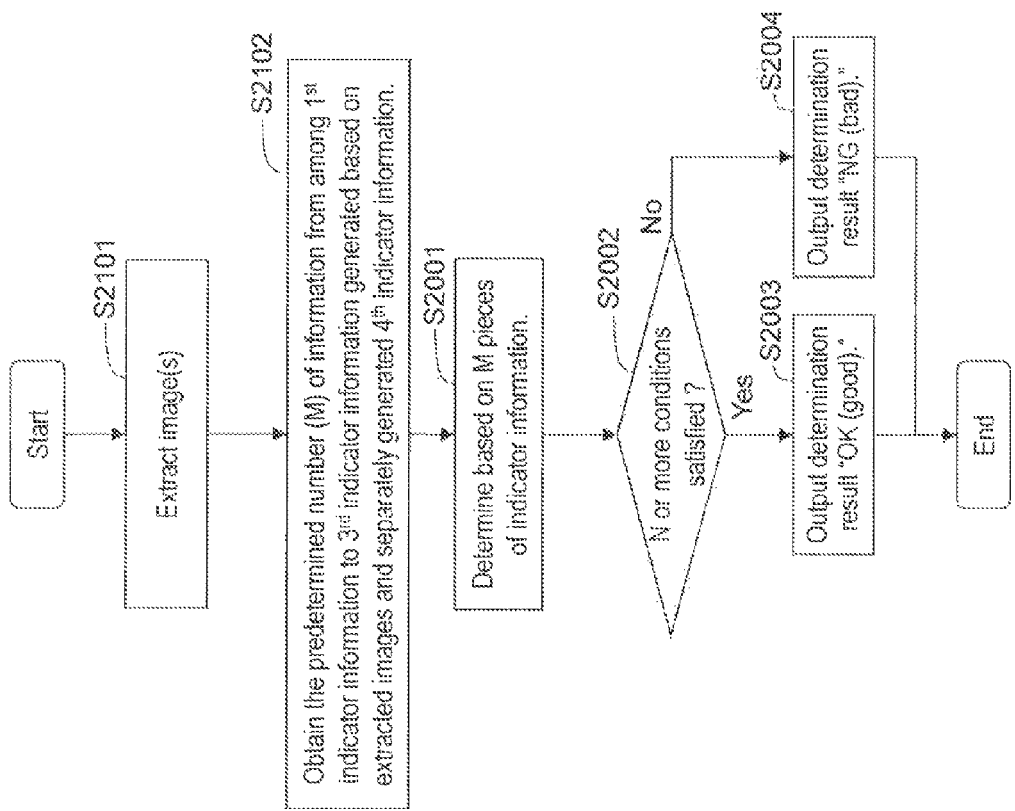
FIG. 21 is a flow chart showing the outline of the method for selecting embryos using an embodiment of the embryo selection apparatus of the present invention.

FIG. 21 shows the outline of the method for selecting embryos using the embryo selection apparatus (700, 1100) comprising the image extraction unit (780, 1180) shown in FIG. 7 or FIG. 11. According to this method, predetermined images required for generation of necessary information among $1^{st}$ to $3^{rd}$ indicator information are extracted (S2101) by the image extraction unit (780, 1180) from the obtained images of candidate embryos. Subsequently, among the $1^{st}$ to $3^{rd}$ indicator information generated based on the predetermined extracted images and/or separately generated $4^{th}$ indicator information, predetermined information is obtained (S2102) by a determination unit (770, 1170). Subsequently, the above S2001 to S2004 are performed.

Figure 22:
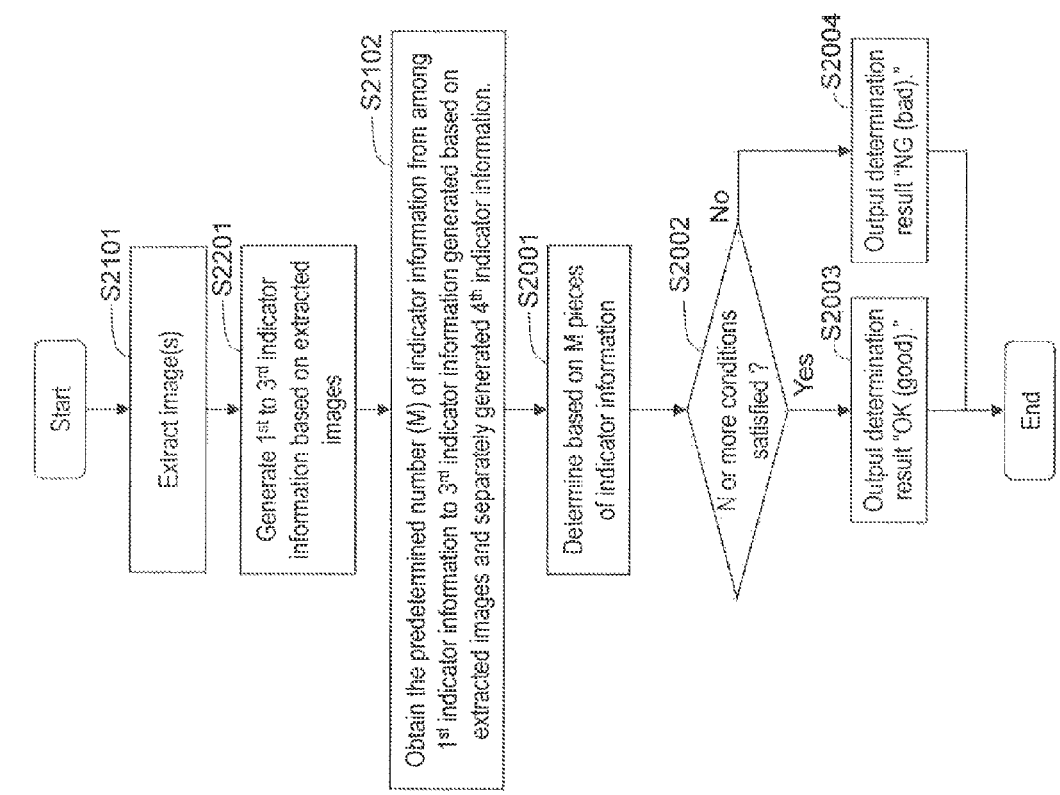
FIG. 22 is a flow chart showing the outline of the method for selecting embryos using an embodiment of the embryo selection apparatus of the present invention.

FIG. 22 shows the outline of the method for selecting embryos using the embryo selection apparatus (800, 1200) further comprising the image analysis unit (890, 1290) shown in FIG. 8 or FIG. 12. According to this method, based on predetermined images extracted through the above S2101, predetermined information is generated from among the $1^{st}$ to the $3^{rd}$ indicator information by the image analysis unit (890, 1290), and then the information is input to the determination unit (870, 1270). Subsequently, the above S2101 and S2001 to S2004 are performed.

Figure 13:
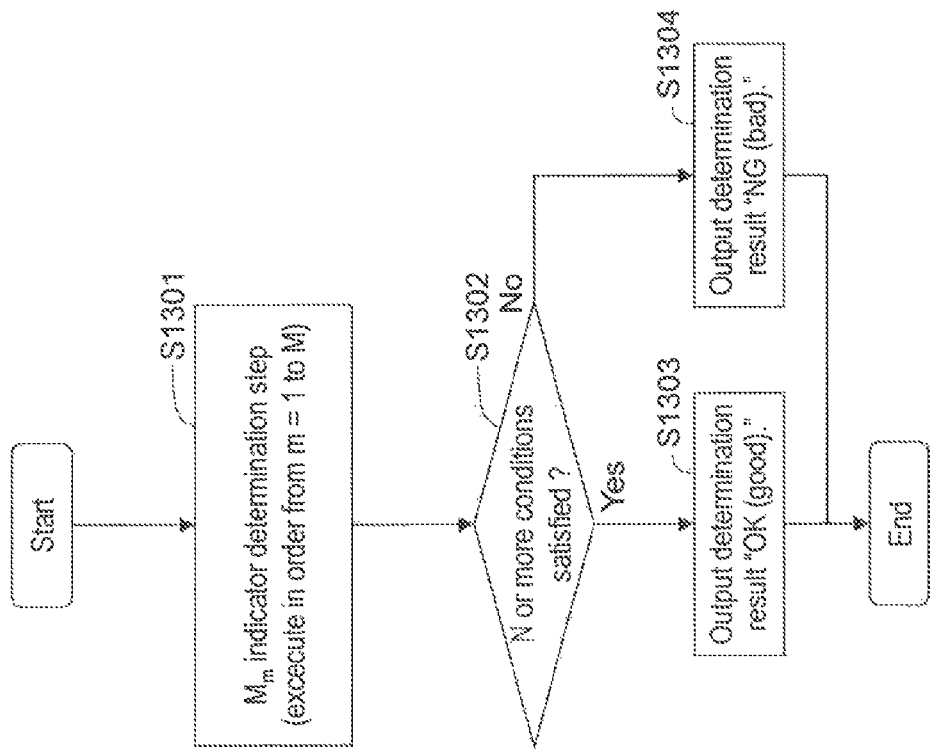
FIG. 13 is a flow chart showing an embodiment of the method for selecting embryos using the embryo selection apparatus of the present invention.

The determination analysis processes of S2001 to S2004 shown in FIG. 20 can be broadly divided into two formats. In one format, as shown in FIG. 13, the $M_m$ indicator determination step (where "m" is an integer selected from 1 to M) is executed from a case in which m=1 to a case in which m=M. After completion (S1301) of the determination concerning the satisfaction of M conditions, an analysis step (S1302) is executed. This method is appropriate for a case in which determination steps and an analysis step are performed after completely obtaining the required indicator information concerning candidate embryos. In the other format, as shown in FIG. 14 to FIG. 19, the determination result "OK (good)" is output at the time point when the N conditions are satisfied, without waiting for the completion of the determination of the satisfaction of all the conditions (M conditions). At the time point when N conditions are determined to be unsatisfied, the result "NG (bad)" is output and the processing is completed. The latter format is appropriate for a case in which the determination steps and the analysis step are performed while obtaining over time the indicator information required for candidate embryos.

A method for selecting embryos shown by a flow chart in FIG. 13 is explained below. The $M_m$ indicator determination sections within the determination unit (670, 970, 1070) executes (S1301) in order the $M_m$ indicator determination steps (from the $M_1$ indicator determination step to the $M_m$ indicator determination step) for determining whether or not the obtained $M_m$ indicator information of candidate embryos satisfies the corresponding $M_m$ indicator selection criteria. Here, "S1301" means to execute M (number of) steps from among the $1^{st}$ indicator determination step, the $2^{nd}$ indicator determination step, the $3^{rd}$ indicator determination step, and the $4^{th}$ indicator determination step, in an arbitrary order. Next, the analysis unit (610, 908, 1006) analyzes (S1302) whether or not the number of conditions determined in S1301 (the $M_1$ indicator determination step to the $M_M$ indicator determination step) to be satisfied is N or more. The analysis unit outputs (S1303) the determination result "OK (good)," indicating that the embryo should be selected, when the number is N or more, and it outputs (S1304) the determination result "NG (bad)," indicating that the embryo should not be selected, when the number is less than N, and then it completes the processing.

Next, methods for selecting embryos as shown in flow charts in FIG. 14 to FIG. 19 are as described below. According to these methods, the $M_m$ indicator determination steps (where "m" is an integer selected from 1 to M) are executed in order from m=1. When the number (x) of conditions determined to be satisfied from among m conditions determined from the $M_1$ indicator determination step to the $M_m$ indicator determination step is N (in a case where x=N), the determination result "OK (good)" is output without proceeding to the $M_{m+1}$ indicator determination step and the following steps, and then the processing is completed. When the number (x) of conditions determined to be satisfied is less than N, and, specifically, N conditions in total are confirmed to be unsatisfied (in a case where x<N and x+(M−m)<N) even if conditions are determined to be satisfied in all the steps from the $M_{m+1}$ indicator determination step to the $M_M$ indicator determination step, for example, the result "NG (bad)" is output and the processing is completed. When the result does not correspond to any of these cases (x<N and N≤x+(M−m)), the processing proceeds to the $M_{m+1}$ indicator determination step.

Figure 14:
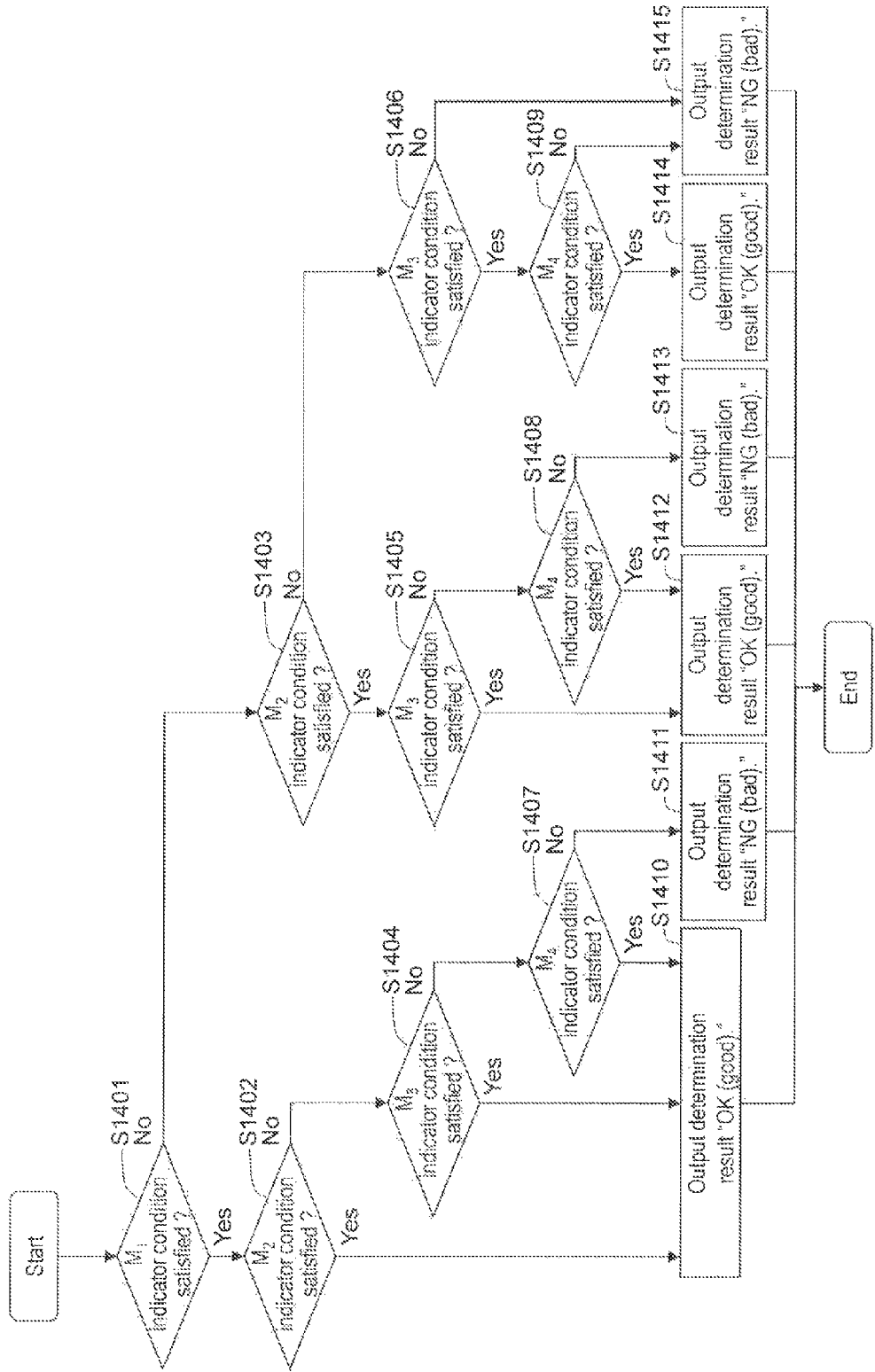
FIG. 14 is a flow chart showing an embodiment of the method for selecting embryos (M=4 and N=2) using the embryo selection apparatus of the present invention.

FIG. 14 shows an example when the threshold in the analysis step of the embryo selection apparatus (600) (M=4) is N=2. S1401 indicates the $M_1$ indicator determination step to be performed by the $M_1$ indicator determination section, S1402 and S1403 indicate the $M_2$ indicator determination step to be performed by the $M_2$ indicator determination section. S1404, S1405, and S1406 indicate the $M_3$ indicator determination step to be performed by the $M_3$ indicator determination section, and S1407, S1408, and S1409 indicate the $M_4$ indicator determination step to be performed by the $M_4$ indicator determination section. The $M_1$ indicator determination section, the $M_2$ indicator determination section, the $M_3$ indicator determination section, and the $M_4$ indicator determination section are selected mutually exclusively from the $1^{st}$ indicator determination section (606), the $2^{nd}$ indicator determination section (607), the $3^{rd}$ indicator determination section (608), and the $4^{th}$ indicator determination section (609) contained in the determination unit (670). S1410, S1412, and S1414 indicate steps whereby the analysis unit 610 outputs the determination result "OK (good)." S1411, S1413, and S1415 indicate steps whereby the analysis unit (610) outputs the determination result "NG (bad)." When the $M_1$ indicator selection criterion is satisfied at S1401 (x, m=1, 1; x<N; and N≤x+(M−m)), the processing proceeds to S1402, but when the same is not satisfied (x,m=0, 1; x<N; and N≤x+(M−m)) at S1401, the processing proceeds to S1403. When the $M_2$ indicator selection criterion is satisfied at S1402 (x,m=2, 2; and x=N), the processing proceeds to S1410, but when the same is not satisfied (x, m=1, 2; x<N; and N≤x+(M−m)), the processing proceeds to S1404. When the $M_3$ indicator selection criterion is satisfied at S1404 (x, m=2, 3; and x=N), the processing proceeds to S1410, but when the same is not satisfied (x, m=1, 3; x<N; and N≤x+(M−m)), the processing proceeds to S1407. When the $M_4$ indicator selection criterion is satisfied at S1407 (x, m=2, 4; and x=N), the processing proceeds to S1410, but when the same is not satisfied (x, m=1, 4; x<N, and x+(M−m)<N), the processing proceeds to S1411. When the $M_2$ indicator selection criterion is satisfied at S1403 (x, m=1, 2; x<N; and N≤x+(M−m)), the processing proceeds to S1405, but when the same is not satisfied (x, m=0, 2; x<N; and N≤x+(M−m)), the processing proceeds to S1406. When the $M_3$ indicator selection criterion is satisfied at S1405 (x, m=2, 3; x=N), the processing proceeds to S1412, but when the same is not satisfied (x, m=1, 3; x<N; and N≤x+(M−m)), the processing proceeds to S1408. When the $M_4$ indicator selection criterion is satisfied at S1408 (x, m=2, 4; x=N), the processing proceeds to S1412, but when the same is not satisfied (x, m=1, 4; x<N; and x+(M−m)<N), the processing proceeds to S1413. When the $M_3$ indicator selection criterion is satisfied at S1406 (x, m=1, 3; x=N), the processing proceeds to S1409, but when the same is not satisfied (x, m=0, 3; x<N; and x+(M−m)<N), the processing proceeds to S1415. When the $M_4$ indicator selection criterion is satisfied at S1409 (x, m=2, 4: x=N), the processing proceeds to S1414, but when the same is not satisfied (x, m=1, 4; x<N; and x+(M−m)<N), the processing proceeds to S1415.

Figure 15:
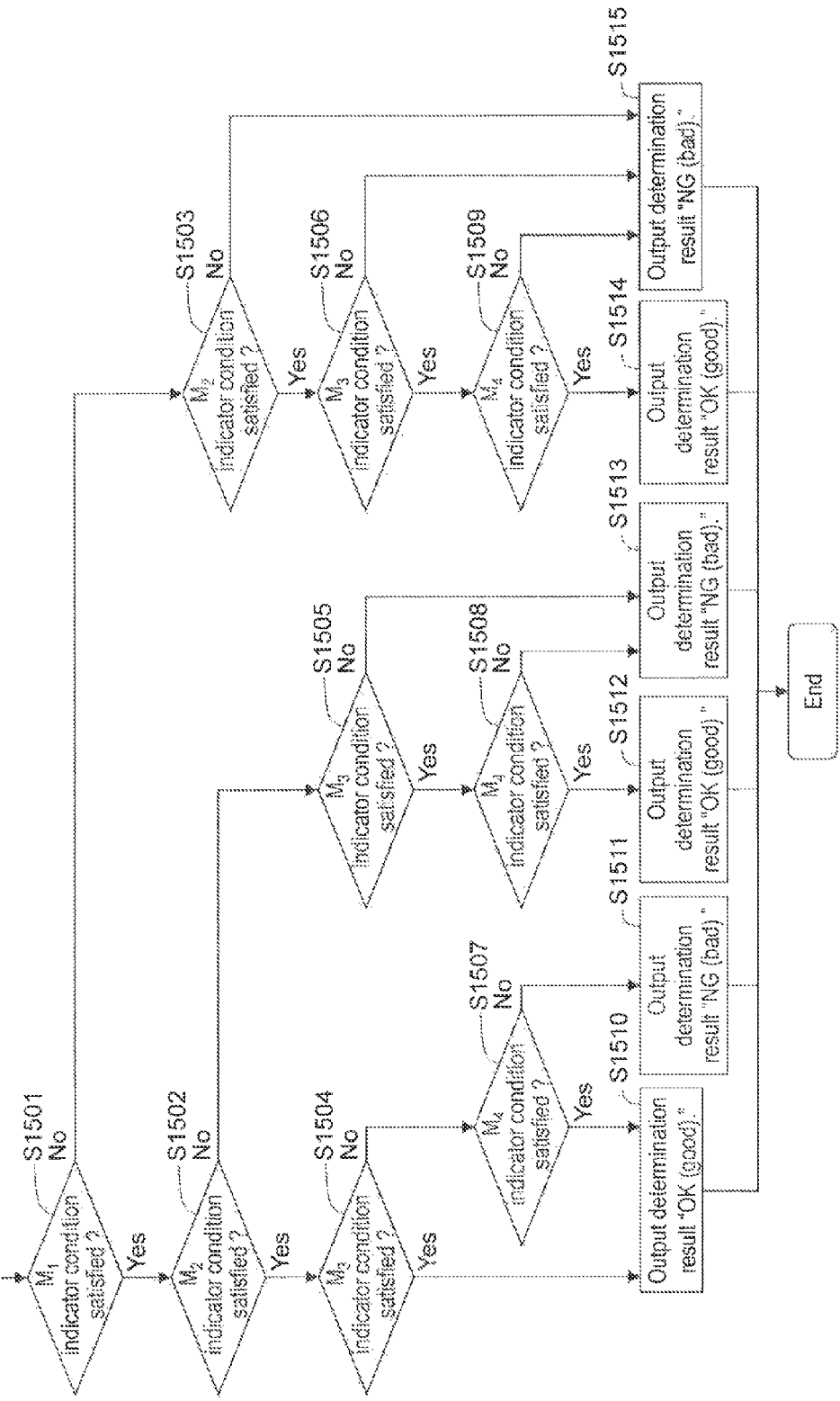
FIG. 15 is a flow chart showing an embodiment of the method for selecting embryos (M=4 and N=3) using the embryo selection apparatus of the present invention.
Figure 16:
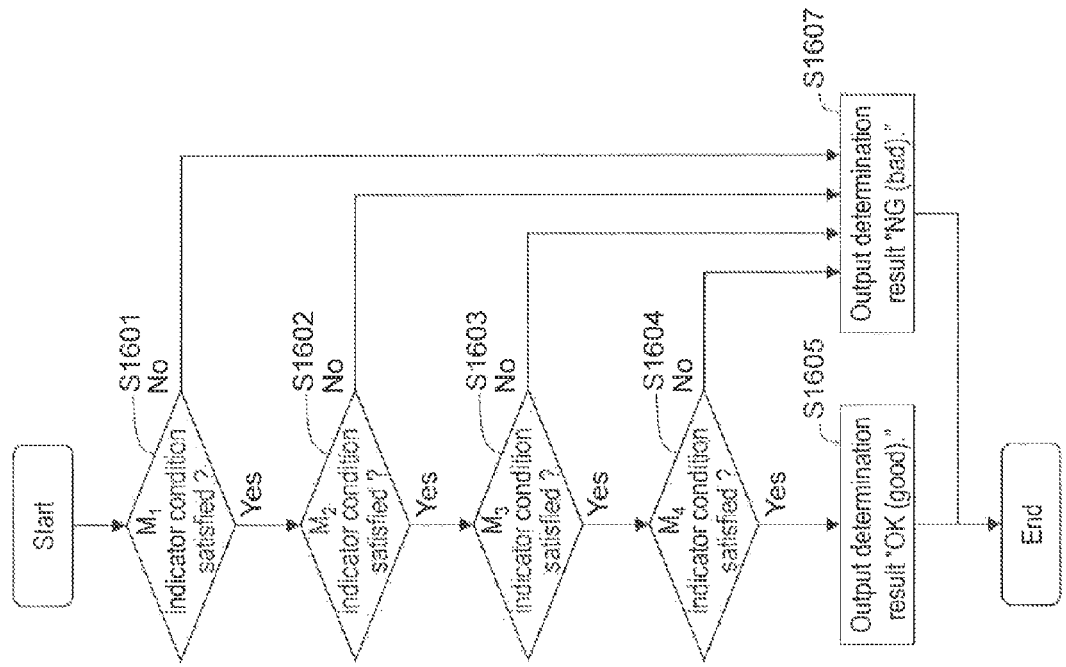
FIG. 16 is a flow chart showing an embodiment of the method for selecting embryos (M=4 and N=4) using the embryo selection apparatus of the present invention.

FIG. 15 shows an embodiment of the operation when the threshold in the analysis step in the embryo selection method using the embryo selection apparatus (600) (M=4) is N=3. FIG. 16 shows an embodiment of the operation when the threshold of the analysis step in the embryo selection method using the embryo selection apparatus (600) (M=4) is N=4. In FIG. 15 and FIG. 16, as in FIG. 14, S1501 and 1601 indicate the $M_1$ indicator determination step to be performed by the $M_1$ indicator determination section, S1502, S1503, and S1602 indicate the $M_2$ indicator determination step to be performed by the $M_2$ indicator determination section, S1504, S1505, S1506, and S1603 indicate the $M_3$ indicator determination step to be performed by the $M_3$ indicator determination section, and S1507, S1508, S1509, and S1604 indicate the $M_4$ indicator determination step to be performed by the MA indicator determination section. S510, S1512, S1514, and S1605 indicate steps whereby the analysis unit (610) outputs the determination result "OK (good)." S1511, S1513, S1515, and S1606 indicate steps whereby the analysis unit (610) outputs the determination result "NG (bad)."

Figure 17:
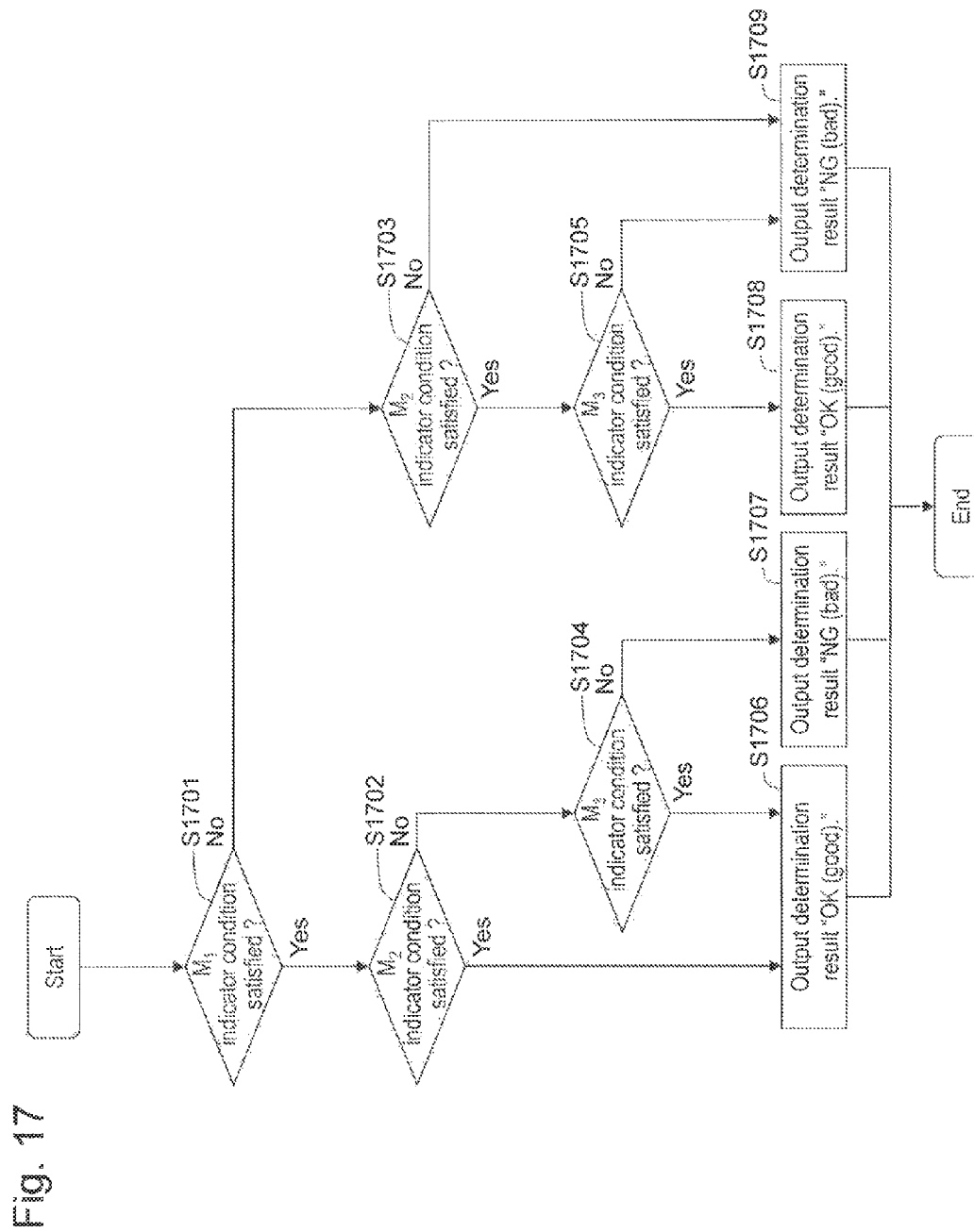
FIG. 17 is a flow chart showing an embodiment of the method for selecting embryos (M=3 and N=2) using the embryo selection apparatus of the present invention.
Figure 18:
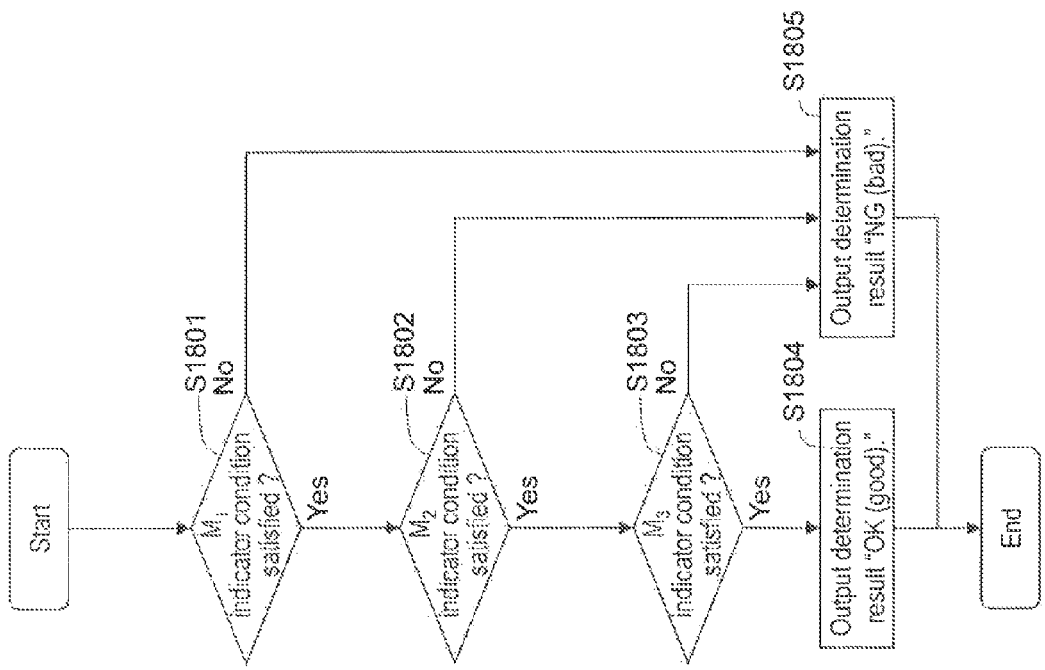
FIG. 18 is a flow chart showing an embodiment of the method for selecting embryos (M=3 and N=3) using the embryo selection apparatus of the present invention.

FIG. 17 shows an embodiment of the operation when the threshold in the analysis step in the embryo selection method using the embryo selection apparatus (900) (M=3) is N=2. FIG. 18 shows an embodiment of the operation when the threshold of the analysis step in the embryo selection method using the embryo selection apparatus (900) (M=3) is N=3. In FIG. 17 and FIG. 18, S1701 and S1801 indicate the $M_1$ indicator determination step to be performed by the $M_1$ indicator determination section (905), S1702, S1703, and S1802 indicate the $M_2$ indicator determination step to be performed by the $M_2$ indicator determination section (906), and S1704, S11705, and S1803 indicate the $M_3$ indicator determination step to be performed by the $M_3$ indicator determination section (907). S1706, S1708, and S1804 indicate steps whereby the analysis unit (908) outputs the determination result "OK (good)." S1707, S1709, and S1805 indicate steps whereby the analysis unit (908) outputs the determination result "NG (bad)."

Figure 19:
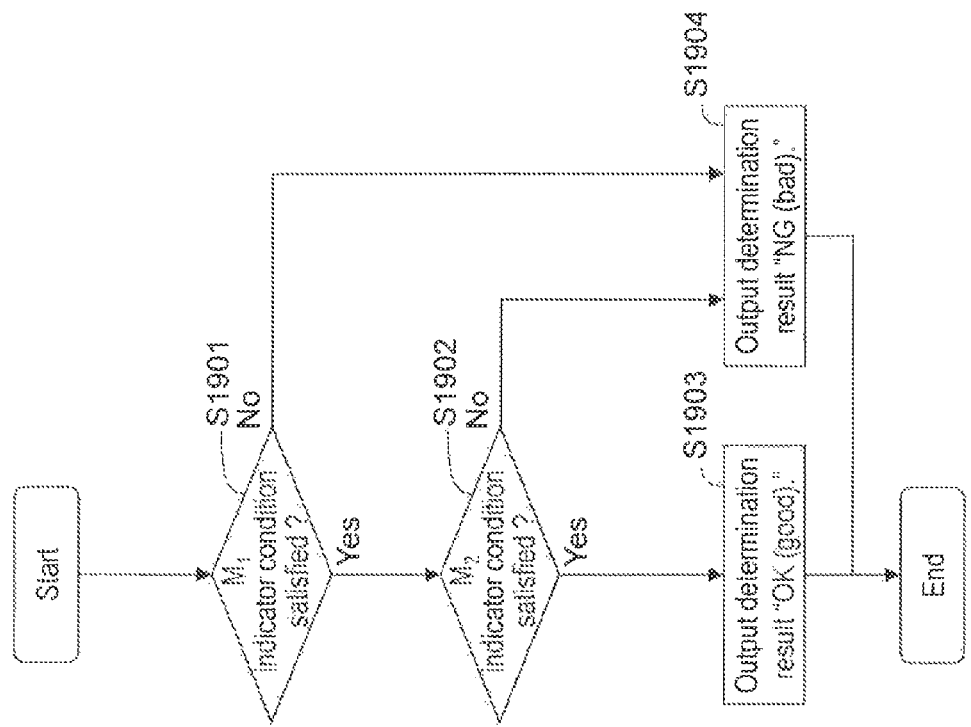
FIG. 19 is a flow chart showing an embodiment of the method for selecting embryos (M=2 and N=2) using the embryo selection apparatus of the present invention.

FIG. 19 shows an embodiment of the operation when the threshold in the analysis step in the embryo selection method using the embryo selection apparatus (1000) (M=2) is N=2. In FIG. 19, S1901 indicates the $M_1$ indicator determination step to be performed by the $M_1$ indicator determination section (1004), and S1902 indicates the $M_2$ indicator determination step to be performed by the $M_2$ indicator determination section (1005). S1903 indicates the step whereby the analysis unit (1006) outputs the determination result "OK (good)." S1904 indicates the step whereby the analysis unit (1006) outputs the determination result "NG (bad)."

FIG. 23a to FIG. 23d specifically show the method for selecting cattle embryos according to the flow chart (M=3; N=2) shown in FIG. 17 using the embryo selection apparatus (900) ($M_1$=2; $M_2$=3; and $M_3$=4) as an example.

When a plurality of candidate embryos are processed simultaneously, an address that specifies each candidate embryo can be assigned. For example, when a candidate embryo is contained within each well of a multi-well plate comprising a plurality of wells (concave parts) aligned in the form of matrix, each candidate embryo can be specified based on coordinates indicating the well (line and column). When one candidate embryo is contained in one well, embryos can be easily managed individually. One well may contain a plurality of candidate embryos. In the latter case, an ID number is further assigned to each embryo within one well, so that embryos can be differentiated from one another.

Each selection criterion and each piece of indicator information of the examples of FIG. 23a to FIG. 23d are as described below.

The $2^{nd}$ indicator determination criterion: At 31 hours after fertilization (upon completion of initial cleavage), the embryo is a 2-cell embryo and no fragmentation is observed.

The $3^{rd}$ indicator selection criterion: At 55 hours after fertilization (upon completion of third cleavage), the embryo is a 5-cell, 6-cell, 7-cell, or 8-cell embryo and no fragmentation is observed.

The $4^{th}$ indicator selection criterion: At 168 hours after fertilization (the early blastocyst stage, the blastocyst stage, or the expanded blastocyst stage), the amount of oxygen consumed per single embryo is $0.91 \times 10^{-14}$ mol $s^{-1}$ or more.

The $2^{nd}$ indicator information: At 31 hours after fertilization, the number of cells and the presence or the absence of fragmentation.

The $3^{rd}$ indicator information: At 55 hours after fertilization, the number of cells and the presence or the absence of fragmentation.

The $4^{th}$ indicator information: At 168 hours after fertilization, the amount of oxygen consumed per single embryo.

Information (lines, columns, and ID numbers) for specifying individual candidate embryos is stored in the memory unit (901) (FIG. 23a). Whether or not the $2^{nd}$ indicator information obtained by the $2^{nd}$ indicator obtaining section (902) satisfies the $2^{nd}$ indicator selection criterion is determined by the $2^{nd}$ indicator determination section (905), and then the $2^{nd}$ d indicator information and the determination results are stored (FIG. 23b). "O.K." indicates that the $2^{nd}$ indicator selection criterion is satisfied and "NG" indicates that the criterion is not satisfied. "O.K." and "NG" can be represented by being replaced with figures such as 1 and 0, respectively. Next, whether or not the $3^{rd}$ indicator information obtained by the $3^{rd}$ indicator obtaining section (903) satisfies the $3^{rd}$ indicator selection criterion is determined by the $3^{rd}$ indicator determination section (906), and then the $3^{rd}$ indicator information and the determination results are stored (FIG. 23c). It is concluded that a candidate embryo that satisfies two conditions at the time of completion of the $3^{rd}$ indicator determination step is a good product. (The flow chart in FIG. 17 is followed in order of S1701, S1702, and S1706.) The analysis result is stored in the memory unit (901). It is concluded that candidate embryos that do not satisfy the two conditions at the time of completion of the $3^{rd}$ indicator determination step are defective. (The flow chart in FIG. 17 is followed in order of S1701, S1703, and S1709.) Then, the analysis result is stored in the memory unit (901). Next, a candidate embryo that satisfies one condition at the time of completion of the $3^{rd}$ indicator determination step is further subjected to determination by the $4^{th}$ indicator determination section (907) for determining whether or not the $4^{th}$ indicator information obtained by the $4^{th}$ indicator obtaining section (904) satisfies the $4^{th}$ indicator selection criterion, and then the $4^{th}$ indicator information and the determination results are stored (FIG. 23d). It is concluded that a candidate embryo that satisfies two conditions is a good product and a candidate embryo that satisfies only one condition is defective, and the analysis results are stored in the memory unit (901).

Figure 24:
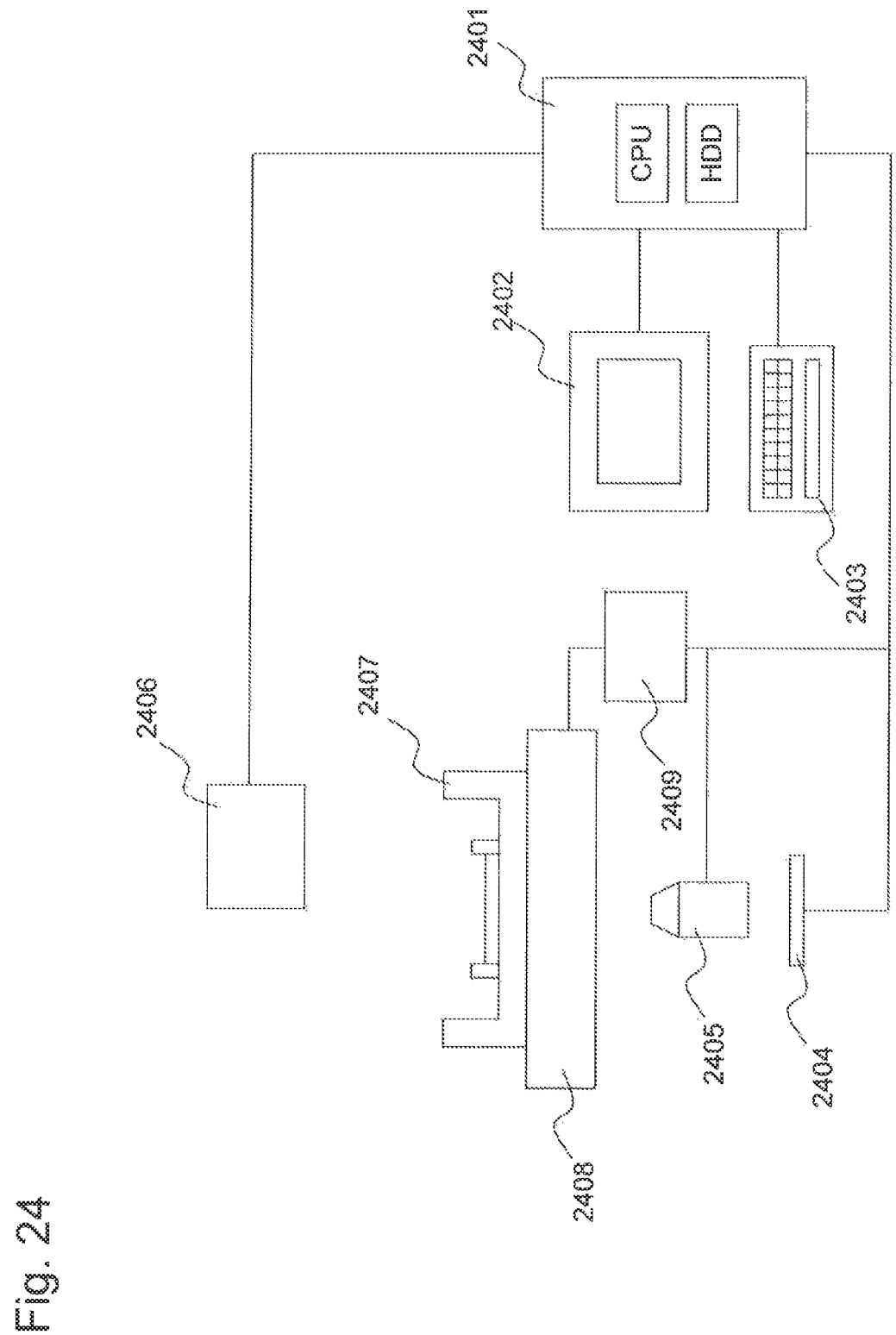
FIG. 24 shows a preferred embodiment of hardware construction of the embryo selection system of the present invention.

FIG. 24 schematically shows a preferred embodiment of the hardware configuration of the embryo selection system of the present invention. The embryo selection apparatus is composed of a computer (2401) comprising a central processing unit (CPU) and a hard disk drive (HDD). An image pickup apparatus comprises a charge-coupled device (CCD) (2404) and an objective lens (2405) with which embryos can be observed. A culture vessel (2407) for culturing embryos is installed on a stage (2408). A position control mechanism (2409) is further preferably provided for controlling the relative positions of an image pickup apparatus (2404, 2405) and a stage (2408), and thus determining the position within the culture vessel (2407) at which an image is to be taken by the image pickup apparatus. The position of the image pickup apparatus (2404, 2405) may be controlled so that a single candidate embryo is or a plurality of candidate embryos are contained within the visual field of an objective lens (2405) upon taking an image. The image pickup apparatus (2404, 2405), the apparatus for measuring the amount of oxygen consumed (2406), a display interface (2402), and an input interface (2403) are connected to the computer (2401).

Each function of the embryo selection apparatus of the present invention can also be realized using a software program code for realizing the function. In this case, a storage medium in which a program code is recorded is provided for the system or the apparatus of the present invention and a computer (or CPU or MPU) of the system or the apparatus reads the program code stored in the storage medium. In this case, the program code itself read from the storage medium realizes the above function, and the program code itself and the storage medium in which the program code is stored configure the present invention. As such a storage medium for supplying program codes, for example, a flexible disk, a CD-ROM, a DVD-ROM, a hard disk, an optical disk, a magneto-optical disk, a CD-R, a magnetic tape, an involatile memory card, a ROM, or the like is used.

Furthermore, as OS (operating system) or the like that runs on a computer executes part of or the entirety of the actual processing based on the instruction provided by the program code, and thus the above function can also be realized by the processing. Moreover, a program code read from the storage medium is written in the memory on a computer, and then, based on the instructions provided by the program code, the CPU or the like of the computer executes a part of or the entirety of the actual processing, and thus the above function can be realized by the processing.

Also, a software program code for realizing the above function is delivered via a network and then stored in a memory means such as a hard disk or the memory of a system or an apparatus, or in a storage medium such as a CD-RW or a CD-R. A computer (or CPU or MPU) of the system or the apparatus reads and executes the program code stored in the memory means or the storage medium, so that the function can also be realized.

The present invention is further specifically explained based on the following Examples. However, the embodiments of and materials and instruments to be used in the present invention are not limited to those in specific examples in the Examples.

EXAMPLES

Experiment 1

Relationship Between the Indicators of the Present Invention and Conception Rate <Materials and Methods>
<Culture Vessel>

In this experiment, a culture vessel (10) shown in FIG. 1a to FIG. 1f was used, in which a cell holding section (3) comprising 25 microwells (4) and a ring-shaped inner wall (5) surrounding the periphery of the cell holding section (3) are formed at the center of a 35-mm culture dish comprising a bottom wall (2) and a side wall (1) provided on the circumference thereof. The diameter "r" of each microwell (4) composing the cell holding section (3) is 270 μm, and the depth "L" thereof is 150 μm. The 25 microwells (4) were aligned to form 5 lines and 5 rows with an interval "a" of 150 μm between wells. A bottom surface (6) of each microwell is inclined downward from the peripheral part to the center, forming a circular conical surface, wherein the angle "α" formed by the center line and the generating line of the circular cone is 83°. The ring-shaped inner wall has a diameter of 7 mm and a height of 1.5 mm. The inner wall (5) with a diameter "d" of 7 mm and a height of 1.5 mm was used for forming droplets of culture solutions.

The culture vessels made of polystyrene and produced by a general injection molding method were used.
<Collection of Oocytes and In Vitro Maturation (IVM)>

Cattle cumulus-oocyte complex (COCs) collection and in vitro maturation were performed following the procedures described in the document of Imai et al. (Imai K, Tagawa M, Yoshioka H, Matoba S, Narita M, Inaba Y, Aikawa Y, Ohtake M, Kobayashi S (2006) The efficiency of embryo production by ovum pick-up and in vitro fertilization in cattle. J Reprod Dev 52 (suppl): 19-29). Ovaries collected from Japanese Black heifers or Holsteins were washed with physiological saline supplemented with 50 μg/ml gentamicin (Sigma Chemical, St Louis, Mo. U.S.A.), and then maintained in the physiological saline at 20° C. for about 20 hours. COCs were aspirated from ovarian follicles (diameter: 2-6 mm) using a 5-mL syringe with a 19 gauge needle, and then they were used for in vitro maturation. As medium for in vitro maturation, 25 mM Heptes buffer TCM199 (M199; Gibco BRL, Grand Island, N.Y., U.S.A.) supplemented with 5% calf serum (CS; Gibco BRL) was used. COCs were washed twice with in vitro maturation medium coated with paraffin oil in 35-mm Petri dishes (Nunclon Multidishes; Nalge Nunc International. Roskide, Denmark) under 5% $CO_2$/95% air with saturated humidity.
<In Vitro Fertilization (IVF)>

In vitro fertilization was performed according to the procedure described in the above document of Imai et al. Specifically, Japanese Black bull sperm samples frozen in 0.5-ml straws were thawed in a water bath at 37° C. for 30 seconds, and then centrifuged in 3 ml of 90% Percoll solution at 2100×g for 10 minutes. Pellets formed by centrifugation were suspended again in a Brackett and Oliphant solution (BO solution) (see document: Brackett B G. Oliphant G (1975) Capacitation of rabbit spermatozoa in vitro. Biol Reprod 12: 260-274)) supplemented with 6 ml of a sperm washing solution (10 mM hypotaurine (Sigma), 2 U/mL heparin (Novo-Heparin Injection 1000; Aventis Pharma Ltd., Tokyo, Japan), and 10 mg/ml bovine serum albumin (BSA, crystallized and lyophilized; Sigma)). Centrifugation was performed to a final concentration of $3 \times 10^6$ sperm cells/ml. Droplets (100 μL) of the suspension were formed on a 35-mm dish, the dish was coated with paraffin oil, and thus fertilization droplets were prepared. COCs were separated from the in vitro maturation medium, washed with a BO solution supplemented with 10 mg/ml BSA, and added to the fertilization droplets, so that each droplet contained 20 COCs. The resultants were cultured under 5% $CO_2$/95% air with saturated humidity at 38.5° C. for 6 hours.
<Pretreatment of Culture Vessel>

Two (2) ml of ethanol was added to a culture vessel (10) for sterilization. After 30 minutes, ethanol was removed from the culture vessel and then dried in air on a warming plate, followed by 10 minutes of ultraviolet sterilization. After sterilization, 125 μl of CR1aa medium supplemented with 5% CS was added to the region surrounded by the ring-shaped inner wall (5) and then coated with paraffin oil. Bubbles within microwells (4) were removed by tapping the vessel from outside. The culture vessels were pre-incubated for at least 3 hours before use.
<In Vitro Culture (IVC)>

In vitro culture was performed in 125 μl of CR1aa medium supplemented with 5% CS under 5% $CO_2$/5% $O_2$/90% $N_2$ with saturated humidity at 38.5° C. for 168 hours. In the test system, the confluency is 5 μl per embryo. The fact that this confluency is the most advantageous for development to the blastocyst stage has been reported in the document of Fujita et al., (Fujita T, Umeki H, Shimura H I, Kugumiya K, Shiga K (2006) Effect of group culture and embryo-culture conditioned medium on development of bovine embryos. J Reprod Dev 52: 137-142). After fertilization, gentle pipetting was performed with a fine glass pipette in a pre-incubated in vitro culture medium, so that cells thought to be zygotes were completely separated from cumulus cells and sperm. Twenty five (25) zygotes were placed within droplets in the microwells (4) of the culture vessel at one zygote per microwell (4).
<Measurement of the Amount of Oxygen Consumed Per Single Embryo>

The amounts of oxygen consumed by individual embryos were measured noninvasively using an SECM system (HV-40S; HOKUTO DENKO Corporation) (see Abe H, Hoshi H (2003) Evaluation of bovine embryos produced in high performance serum-free media. J Reprod Dev 49: 193-202; and Shiku H, Shiraishi T, Ohya H. Matsue T, Abe H, Hoshi H., Kobayashi M (2001) Oxygen consumption of single bovine embryos probed by scanning electrochemical microscopy. Anal Chem 73: 3751-3758). Embryos were transferred one by one to a plate tilled with 5 ml of embryo respiration assay medium-2 (ERAM-2; Research Institute for the Functional Peptides), so that embryos precipitated at the bottoms of microwells. The plate was placed on a warming plate on a microscope stage and then the temperature of the ERAM-2 solution was maintained at 38.5° C. The amounts of oxygen consumed were measured by the method described in the above document of Shiku H et al. An XYZ stage and a potentiostat were controlled by a computer. The voltammetry of a Pt-microdisk electrode (HOKUTO DENKO Corporation) in the ERAM-2 solution results in a current-potential curve. In the vicinity of embryo surfaces, no response from other electrochemically active chemical species was observed. The oxygen consumption rates of embryos were calculated using software. The software can estimate a difference ($\Delta C$) in the amount of oxygen consumed between a bulk solution and the surface of an embryo sample and an oxygen consumption rate (F, unit: mol s$^{-1}$) of one embryo sample based on the spherical diffusion theory (the above document of Shiku H et al.). Electrodes were scanned twice in opposite order, and then the mean value of $\Delta C$ was estimated for each embryo sample.

<Evaluation of Embryo Morphology Using Time-Lapse Cinematography (TLC)>

Cleavage state and embryo morphology were evaluated as described in the document of Somfai T et al. (Somfai T, Inaba Y, Aikawa Y, Ohtake M, Kobayashi S, Konishi K, Imai K (2009) Relationship Between the Length of Cell Cycles, Cleavage Pattern and Developmental Competence in Bovine Embryos Generated by In Vitro Fertilization or Parthenogenesis. J Reprod Dev 56: 200-207). Embryos were cultured under 5% $CO_2$/5% $O_2$/90% N, with saturated humidity at 38.5° C. Generation was monitored using a real-time culture cell monitoring system (CCM-M1.4Z; ASTEC Co., Ltd.). During the culture period of 168 hours, 673 photographs of embryos were taken at 15-minute intervals using a 4× plain objective. The thus accumulated images were analyzed using CCM-M1.4 software (ASTEC Co., Ltd.).

<Sexual Cycle Synchronization and Embryo Implantation>

The sexual cycles of Japanese Black cattle/Holstein hybrids as recipients were synchronized using 3 ml of prostaglandin $F_{2\alpha}$. One embryo (selected based on indicators described later) on day 7 after fertilization was implanted into the uterine horn on the side of the corpus *luteum* of each synchronized recipient on days 7 to 8 after the initiation of estrus. All recipients were similarly fed and managed, and estrus behavior was observed at least twice a day, in the morning and in the evening.

<Conception Diagnosis>

On days 30 and 60 after embryo implantation, conception diagnosis was performed using ultrasonography (HS101V; Honda Electronics Co., Ltd.). Conception was confirmed by observing intrauterine fetuses and confirming fetal heartbeats.

<Indicators>

The following indicators were used. The following indicators 1 and 2 are conventionally used for embryo selection.

Indicator 1: Morphological quality at 168 hours after fertilization is Code 1.

Indicator 2: An embryo has reached the expanded blastocyst stage at 168 hours after fertilization.

Indicator 3: An embryo is a 2-cell embryo at 31 hours after fertilization (upon completion of initial cleavage), and no fragmentation is observed.

Indicator 4: An embryo is a 5-cell, 6-cell, 7-cell, or 8-cell embryo at 55 hours after fertilization (upon completion of third cleavage), and no fragmentation is observed.

Indicator 5: The amount of oxygen consumed per single embryo at 168 hours after fertilization (the early blastocyst stage, the blastocyst stage, or the expanded blastocyst stage) is $0.91 \times 10^{-14}$ mol s$^{-1}$ or more.

The morphological quality of "Code 1" in Indicator 1 is as defined in Robertson I, Nelson R E (1998) Certification and identification of the embryo, in: D. A. Stringfellow and S. M. Seidel. Editors, Manual of the international embryo transfer society, IETS, Savoy, Ill. 103-116. Specifically, at the time of 168 hours after fertilization, an embryo observed to exhibit normal growth and no abnormal morphology (e.g., asymmetrical or degenerated egg cells) is evaluated to have the morphological quality of Code 1.

<Results>

The relationship between the number of implanted embryos satisfying each indicator above and conception rate is shown in the following table. The presence or the absence of conception was observed on day 60 after embryo implantation.

TABLE 1

| Indicator | Number of implanted embryos that satisfied indicators | Number (%) of implanted embryos that resulted in no conception | Number (%) of implanted embryos that resulted in conception |
|---|---|---|---|
| Indicator 1 | 8 | 4 (50.0) | 4 (50.0) |
| Indicator 2 | 13 | 7 (53.8) | 6 (46.2) |
| Indicator 1 and 2 | 7 | 4 (57.1) | 3 (42.9) |
| Indicator 3 | 12 | 6 (50.0) | 6 (50.0) |
| Indicator 4 | 11 | 4 (36.4) | 7 (63.6) |
| Indicator 5 | 9 | 4 (44.4) | 5 (55.6) |
| Indicator 3, 4 and 5 | 5 | 1 (20.0) | 4 (80.0) |
| Indicator 3 and 4 | 10 | 3 (30.0) | 7 (70.0) |
| Indicator 3 and 5 | 5 | 1 (20.0) | 4 (80.0) |
| Indicator 4 and 5 | 5 | 1 (20.0) | 4 (80.0) |
| Indicator 1 and 3 | 8 | 4 (50.0) | 4 (50.0) |
| Indicator 2 and 3 | 12 | 6 (50.0) | 6 (50.0) |
| Indicator 1, 2 and 3 | 8 | 4 (50.0) | 4 (50.0) |
| Indicator 1 and 4 | 6 | 2 (33.3) | 4 (66.7) |
| Indicator 2 and 4 | 8 | 3 (37.5) | 5 (62.5) |
| Indicator 1, 2 and 4 | 5 | 2 (40.0) | 3 (60.0) |
| Indicator 1 and 5 | 7 | 3 (42.9) | 4 (57.1) |

TABLE 1-continued

| Indicator | Number of implanted embryos that satisfied indicators | Number (%) of implanted embryos that resulted in no conception | Number (%) of implanted embryos that resulted in conception |
|---|---|---|---|
| Indicator 2 and 5 | 6 | 2 (33.3) | 4 (66.7) |
| Indicator 1, 2 and 5 | 5 | 2 (40.0) | 3 (60.0) |

Indicators 1 and 2 are conventionally used as indicators for selecting implanted embryos. However, even when implanted embryos that had satisfied one of or a combination of both indicators were used, the resulting conception rate was 50% or less. It was demonstrated that conventional indicators based only on the morphology of embryos at 168 hours after fertilization are not always sufficient for selecting implanted embryos having high conception rates.

The highest conception rate was 63.6% among those of implanted embryos that had satisfied one of indicators 3, 4, and 5.

Even in the case of implanted embryos that had satisfied combinations of indicators (a combination of either one of indicator 1 or 2 or both indicators, and any one of indicators 3, 4, and 5), conception rates were always found to be less than 70%.

However, surprisingly, implanted embryos that had satisfied combinations of at least two of indicators 3, 4, and 5 were confirmed to have conception rates of 70% or 80%.

It was concluded by the above results that specifically high conception rates can be realized using combinations of at least two of indicators 3, 4, and 5 as indicators for selecting implanted embryos.

Experiment 2

Preliminary Examination

The above indicators 3 to 5 had been predicted to be useful as factors for predicting that embryos have high conception rates based on the results of the preliminary examination conducted before Experiment 1. Procedures and results of the preliminary examination are as described below.

Embryos used in this experiment were cattle (*Bos taurus*) embryos.
<Predictive Indicator Candidates>
The following indicators were used as predictive factor candidates.

At 31 hours after fertilization (upon completion of initial cleavage): the number of blastomeres, the uniformity of blastomeres, and the presence or absence of fragmentation.

At 55 hours after fertilization (upon completion of third cleavage): the number of blastomeres, the uniformity of blastomeres, and the presence or absence of fragmentation.

At 168 hours after fertilization (the early blastocyst stage, the blastocyst stage, or the expanded blastocyst stage): the blastocyst stage (whether or not an embryo has reached the expanded blastocyst stage) and the amount of oxygen consumed.
<Evaluation Method>
The total number of cells in an embryo, the number of cells of inner cell mass (ICM), the number of trophectoderm (TE) cells, ICM cells (%), and hatching (%) from the zona pellucida, and the conception rate after embryo implantation are known to exhibit a positive correlation.

The apoptosis positive cells (%) of an embryo and the conception rate after embryo implantation are known to exhibit a negative correlation.

Correlations of the above indicators with the total number of embryonic cells, the number of ICM cells, the number of TE cells, ICM cells (%), apoptosis positive cells (%), and hatching (%) of embryos from the zona pellucida were examined, and then whether or not the indicators were useful as predictive factors was confirmed.

In vitro culture procedures for obtaining embryos, a method for observing cleavage state, and procedures for measuring the amount of oxygen consumed are similar to those in Experiment 1.

The number of cells, apoptosis positive cells (%), hatching (%) from the zona pellucida, and the non-uniformity of blastomeres were measured by the following procedures.
<Measurement of the Number of Cells>
Cell distribution in embryos was evaluated by differential staining of ICM and TE according to procedures described in the document of Thouas et al. (Thouas G A, Korfiatis N A, French A J, Jones G M, Trounson A O (2001) Simplified technique for differential staining of inner cell mass and trophectoderm cells of mouse and bovine blastocysts. Reprod Biomed Online 3: 25-29).

With the method, embryonic cells were stained with 100 µg/ml propidium iodide fluorochrome containing a penetrant solution of 0.2% (v % v) Triton X-100 ionic surfactant for 40 seconds. Subsequently, embryos were incubated in a $2^{nd}$ solution (Hoechst 33342 was contained in 99.5% ethanol at a concentration of 25 µg/ml) for 5 minutes for fixation. After staining and fixation, the number of embryonic cells was observed with an epifluorescence microscope (IX-71; Olympus Corporation, Tokyo). Blue nuclei indicate ICM cells and pink to red nuclei indicate TE cells. The sum of the number of ICM cells and the number of TE cells was the total number of cells.
<Measurement of Apoptosis Positive Cells (%)>
According to the procedures in the document of Yamanaka et al., (Yamanaka K, Sugimura S, Wakai T, Kawahara M, Sato E (2009) Difference insensitivity to culture condition between in vitro fertilized and somatic cell nuclear transfer embryos in pigs. J Reprod Dev 55: 299-304), apoptosis positive cells were detected by TUNEL assay.

Embryos were washed three times in PBS supplemented with 0.1% polyvinylpyrrolidone (Sigma) and then fixed in 2% (w/v) paraformaldehyde (Sigma) and 0.2% (v/v) Triton-X (Sigma) PBS (phosphate buffer) solution at room temperature for 40 hours. Apoptosis positive cells were detected using a commercially available kit (ApopTag; Chemicon, Temecula, Calif., U.S.A.). As a positive control sample, an embryo treated with DNase 1 (10 IU/mL, Sigma) was used.

After 10 minutes of washing with 0.1% PVA (polyvinyl alcohol) PBS, embryos were incubated in the buffer of the above kit for 20 minutes at room temperature. Next, within a chamber under wet conditions, embryos were incubated with 70% (v/v) reaction buffer containing 30% (v/v) terminal deoxynucleotidyl transferase and digoxigenin-11-dUTP at 37° C. for 2 hours. Three (3) % (v/v) stop/wash buffer (Chemicon) was added at 37° C. for 10 minutes to stop the reaction. After washing four times (2 minutes each) with PBS containing 0.2% (v/v) Triton-X, the resultant was incubated with a horseradish peroxidase conjugated anti-digoxigenin antibody at room temperature for 1 hour. After washing four times with 0.2% Triton-X and 0.1% PVA PBS, embryos were stained with a solution containing 10 μg/mL propidium iodide in PBS at room temperature for 1 hour. All samples were observed with an epifluorescence microscope. The numbers of apoptosis positive nuclei and the total numbers of nuclei within embryos were measured. TUNEL positive cells were indicated with yellow to green.

<Hatching (%) from the Zona Pellucida>

The term "hatching (%) from the zona pellucida" refers to the percentage accounted for by embryos that completely hatched from the zona pellucida. This is determined by visual observation of enlarged views of embryos.

<Non-Uniformity of Blastomeres>

The non-uniformity of blastomere size was determined by visual observation of enlarged views of embryos.

<Results>

The results of analyzing the relationship of each predictive factor (indicator) with the total number of embryonic cells, the number of ICM cells, the number of TE cells, the percentage accounted for by the number of ICM cells with respect to the total number of cells (ICM %), apoptosis positive cells (%), and hatching (%) from the zona pellucida by multiple regression analysis are summarized as follows.

The relationships of predictive factors with the total number of cells, the number of ICM cells. TE cells, ICM %, apoptosis positive cells (%), and the success or failure of the hatching (%) from the zona pellucida were analyzed by logistic analysis. Logistic analysis was conducted according to Applied Logistic Regression Analysis, $2^{nd}$ ed. (Menard 2002). Dependent variables are the total number of cells (continuous variable), the number of ICM cells (continuous variable), the number of TE cells (continuous variable), ICM % (continuous variable), apoptosis positive cells (%): continuous variable), and the success or failure of hatching (%) from the zona pellucida (nominal variable: success is designated as "1" and failure is designated as "0."). Independent variables are the number of blastomeres on Day 1 (nominal variable: 2-cell embryos are designated as "1" and embryos other than 2-cell embryos are designated as "0."), the non-uniformity of blastomeres (nominal variable: non-uniform blastomeres are designated as "1" and uniform blastomeres are designated as "0."), the presence or the absence of fragmentation (nominal variable: the presence of fragmentation is designated as "1" and the absence of fragmentation is designated as "0."), the number of blastomeres on Day 2 (embryos at 3-cell to 4-cell stages) (nominal variable: embryos at 3-cell to 4-cell stages are designated as "1" and embryos other than those at 3-cell to 4-cell stages are designated as "0."), the number of blastomeres (embryos at 5-cell to 8-cell stages) (nominal variable: embryos at 5-cell to 8-cell stages are designated as "1" and embryos other than those at 5-cell to 8-cell stages are designated as "0," (specifically, embryos at 3-cell to 4-cell stages are represented by "1, 0," embryos at 5-cell to 8-cell stages are represented by "0, 1," and embryos at >8-cell stage are represented by "0, 0"), the uniformity of blastomeres (nominal variable similar to Day 1), the presence or the absence of fragmentation (nominal variable similar to Day 1), the success or the failure of development to the expanded blastocyst stage on Day 7 (nominal variable: the success is designated as "1" and the failure is designated as "0."), and oxygen consumption (continuous variable). Also, when "1" is not contained in 95% confidence interval, the analytical result is determined to be statistically significant.

TABLE 2

Total number of cells

| Observation day | Predictive factor | Coefficient | Standard error | Odds ratio | P VALUE | 95% Confidence interval | |
|---|---|---|---|---|---|---|---|
| | Section | 53.448 | 9.263 | 5.770 | <0.001 | 35.170 | 71.726 |
| Day 1 (31 h) | Number of blastomeres (2-cell) | 10.530 | 6.455 | 1.631 | 9.105 | −2.208 | 23.269 |
| | Non-uniform blastomeres | −5.680 | 5.724 | −0.992 | 0.322 | −16.975 | 5.615 |
| | Fragmentation (+) | 2.088 | 7.417 | 0.282 | 0.779 | −12.548 | 16.724 |
| Day 2 (55 h) | Number of blastomeres (3-cell to 4-cell) | −11.776 | 11.714 | −1.005 | 0.316 | −34.892 | 11.340 |
| | Number of blastomeres (5-cell to 8-cell) | −0.158 | 8.026 | −0.020 | 0.984 | −15.996 | 15.679 |
| | Non-Uniform blastomeres | −5.866 | 5.733 | −1.023 | 0.308 | −17.178 | 5.447 |
| | Fragmentation (+) | −16.300 | 6.772 | −2.407 | 0.017 | −29.663 | −2.937 |
| Day 7 (168 h) | Reached expanded blastocyst stage | 20.520 | 5.997 | 3.422 | 0.001 | 8.687 | 32.353 |
| | Oxygen consumption ($\times 10^{-14}$ mol s$^{-1}$) | 37.804 | 6.921 | 5.463 | <0.001 | 24.145 | 51.461 |

R = 0.604*

TABLE 3

Number of ICM cells

| Observation day | Predictive factor | Coefficient | Standard error | Odds ratio | P VALUE | 95% Confidence interval | |
|---|---|---|---|---|---|---|---|
| | Section | 16.120 | 3.450 | 4.672 | <0.001 | 9.311 | 22.929 |
| Day 1 (31 h) | Number of blastomeres (2-cell) | 0.346 | 2.569 | 0.135 | 0.893 | −4.723 | 5.416 |
| | Non-uniform blastomeres | −2.391 | 2.129 | −1.123 | 0.263 | −6.593 | 1.810 |
| | Fragmentation (+) | 1.283 | 2.767 | 0.464 | 0.644 | −4.178 | 6.743 |
| Day 2 (55 h) | Number of blastomeres (3-cell to 4-cell) | −3.723 | 4.388 | −0.849 | 0.397 | −12.381 | 4.935 |
| | Number of blastomeres (5-cell to 8-cell) | 1.897 | 3.107 | 0.610 | 0.542 | −4.235 | 8.029 |
| | Non-uniform blastomeres | −1.710 | 2.130 | −0.803 | 0.423 | −5.914 | 2.494 |
| | Fragmentation (+) | −5.093 | 2.515 | −2.025 | 0.044 | −10.056 | −0.130 |
| Day 7 (168 h) | Reached expanded blastocyst stage | 5.208 | 2.229 | 2.336 | 0.021 | 0.809 | 9.608 |
| | Oxygen consumption ($\times 10^{-14}$ mol s$^{-1}$) | 12.518 | 2.562 | 4.886 | <0.001 | 7.462 | 17.574 |

R = 0.526*

TABLE 4

Number of TE cells

| Observation day | Predictive factor | Coefficient | Standard error | Odds ratio | P VALUE | 95% Confidence interval | |
|---|---|---|---|---|---|---|---|
| | Section | 37.299 | 7.131 | 5.230 | <0.001 | 23.227 | 51.372 |
| Day 1 (31 h) | Number of blastomeres (2-cell) | 10.065 | 4.970 | 2.025 | 0.044 | 0.257 | 19.872 |
| | Non-uniform blastomeres | −3.284 | 4.407 | −0.745 | 0.457 | −11.981 | 5.412 |
| | Fragmentation (+) | 0.813 | 5.711 | 0.142 | 0.887 | −10.455 | 12.082 |
| Day 2 (55 h) | Number of blastomeres (3-cell to 4-cell) | −7.972 | 9.019 | −0.884 | 0.378 | −25.769 | 9.825 |
| | Number of blastomeres (5-cell to 8-cell) | −1.992 | 6.179 | −0.322 | 0.748 | −14.185 | 10.202 |
| | Non-uniform blastomeres | −4.139 | 4.414 | −0.938 | 0.350 | −12.849 | 4.570 |
| | Fragmentation (+) | −11.188 | 5.214 | −2.146 | 0.033 | −21.476 | −0.900 |
| Day 7 (168 h) | Reached expanded blastocyst stage | 15.332 | 4.617 | 3.321 | 0.001 | 6.221 | 24.443 |
| | Oxygen consumption ($\times 10^{-14}$ mol s$^{-1}$) | 25.319 | 5.328 | 4.752 | <0.001 | 14.804 | 35.833 |

R = 0.570*

TABLE 5

ICM cells % (ICM %)

| Observation day | Predictive factor | Coefficient | Standard error | Odds ratio | P VALUE | 95% Confidence interval | |
|---|---|---|---|---|---|---|---|
| | Section | 30.568 | 2.059 | 14.849 | <0.001 | 26.506 | 34.630 |
| Day 1 (31 h) | Number of blastomeres (2-cell) | −3.409 | 1.473 | −2.315 | 0.022 | −6.315 | −0.503 |
| | Non-uniform blastomeres | −0.270 | 1.285 | −0.210 | 0.834 | −2.806 | 2.267 |
| | Fragmentation (+) | 0.842 | 1.666 | 0.506 | 0.614 | −2.445 | 4.130 |
| Day 2 (55 h) | Number of blastomeres (3-cell to 4-cell) | 0.198 | 2.628 | 0.075 | 0.940 | −4.989 | 5.384 |
| | Number of blastomeres (5-cell to 8-cell) | 2.069 | 1.803 | 1.148 | 0.253 | −1.489 | 5.626 |
| | Non-uniforms blastomeres | −0.069 | 1.289 | −0.054 | 0.957 | −2.612 | 2.474 |
| | Fragmentation (+) | −0.687 | 1.521 | −0.452 | 0.652 | −3.690 | 2.315 |
| Day 3 (168 h) | Reached expanded blastocyst stage | −0.592 | 1.346 | −0.440 | 0.660 | −3.248 | 2.063 |
| | Oxygen consumption ($\times 10^{-14}$ mol s$^{-1}$) | 0.925 | 1.553 | 0.596 | 0.552 | −2.139 | 3.990 |

R = 0.191

TABLE 6

Apoptosis positive cells (%)

| Observation day | Predictive factor | Coefficient | Standard error | Odds ratio | P VALUE | 95% Confidence interval | |
|---|---|---|---|---|---|---|---|
| | Section | 16.614 | 2.180 | 7.623 | <0.001 | 12.308 | 20.920 |
| Day 1 (31 h) | Number of blastomeres (2-cell) | 1.051 | 1.837 | 0.572 | 0.568 | −2.578 | 4.680 |
| | Non-uniform blastomeres | 1.464 | 1.409 | 1.039 | 0.300 | −1.319 | 4.248 |
| | Fragmentation (+) | 0.227 | 1.606 | 0.141 | 0.888 | −2.946 | 3.400 |
| Day 2 (55 h) | Number of blastomeres (3-cell to 4-cell) | 0.058 | 2.793 | 0.021 | 0.983 | −5.460 | 5.577 |
| | Number of blastomeres (5-cell to 8-cell) | −4.339 | 2.049 | −2.118 | 0.036 | −8.388 | −0.291 |
| | Non-uniform blastomeres | 2.390 | 1.438 | 1.662 | 0.099 | −0.451 | 5.232 |
| | Fragmentation (+) | 4.297 | 1.340 | 3.206 | 0.002 | 1.649 | 6.945 |
| Day 7 (168 h) | Reached expanded blastocyst stage | −1.067 | 1.471 | −0.725 | 0.470 | −3.974 | 1.840 |
| | Oxygen consumption ($\times 10^{-14}$ mol s$^{-1}$) | −1.453 | 1.566 | −0.928 | 0.355 | −4.547 | 1.641 |

R = 0.413*

TABLE 7

Hatching of embroyo from the zona pellucida

| Observation day | Predictive factor | Coefficient | Standard error | P VALUE | Odds ratio | 95% Confidence interval | |
|---|---|---|---|---|---|---|---|
| Day 1 (31 h) | Number of blastomeres (2-cell) | 1.933 | 0.568 | <0.001 | 6.91 | 2.268 | 21.055 |
| | Non-uniform blastomeres | 0.538 | 0.477 | 0.26 | 1.71 | 0.672 | 4.364 |
| | Fragmentation (+) | −1.719 | 0.535 | 0.001 | 0.179 | 0.063 | 0.511 |
| Day 2 (55 h) | Number of blastomeres (3-cell to 4-cell) | −1.118 | 0.897 | 0.212 | 0.327 | 0.056 | 1.896 |
| | Number of blastomeres (5-cell to 8-cell) | −0.211 | 0.7 | 0.764 | 0.81 | 0.205 | 3.195 |
| | Non-Uniform blastomeres | −0.099 | 0.554 | 0.858 | 0.905 | 0.306 | 2.68 |
| | Fragmentation (+) | −0.287 | 0.522 | 0.583 | 0.751 | 0.27 | 2.088 |
| Day 7 (168 h) | Reached expanded blastocyst stage | 0.973 | 0.462 | 0.035 | 2.647 | 1.069 | 6.552 |
| | Oxygen consumption ($\times 10^{-14}$ mol s$^{-1}$) | 4.39 | 0.959 | <0.001 | 80.67 | 12.302 | 528.997 |

R = 0.601*

Table 2 shows the presence of a significant correlation of the presence or the absence of fragmentation at 55 hours after fertilization, and the blastocyst stage and oxygen consumption at 168 hours after fertilization with the total number of cells. Based on the results, the selection of an embryo consuming a large amount of oxygen at the expanded blastocyst stage and not undergoing fragmentation at 55 hours after fertilization is inferred to be effective for the selection of an embryo having a large total number of cells.

Table 3 shows that the presence or the absence of fragmentation at 55 hours after fertilization, and the presence of a significant correlation of the blastocyst stage and oxygen consumption at 168 hours after fertilization with the number of ICM cells. Based on the results, the selection of an embryo consuming a large amount of oxygen at the expanded blastocyst stage and not undergoing fragmentation at 55 hours after fertilization is inferred to be effective for the selection of an embryo having the large number of ICM cells.

Table 4 shows the presence of a significant correlation of the number of blastomeres at 31 hours after fertilization, the presence or the absence of fragmentation at 55 hours after fertilization, and the blastocyst stage and oxygen consumption at 168 hours after fertilization with the number of TE cells. Based on the results, the selection of an embryo consuming a large amount of oxygen at the expanded blastocyst stage, exhibiting the developmental stage of 2-cell stage at 31 hours after fertilization, and not undergoing fragmentation at 55 hours after fertilization is inferred to be effective for the selection of an embryo having the large number of TE cells.

Table 5 shows the presence of a significant correlation of the number of blastomeres at 31 hours after fertilization with ICM cell (%) (ICM %). Based on the results, the selection of an embryo exhibiting the developmental stage of 2-cell at (a time point) 31 hours after fertilization is inferred to be effective in order to select an embryo with high ICM %.

Table 6 shows the presence of a significant correlation of the number of blastomeres and the presence or the absence of fragmentation at 55 hours after fertilization with apoptosis positive cells (%). Based on the results, the selection of an embryo exhibiting a developmental stage (5-cell to 8-cell stages) and not undergoing fragmentation at 55 hours after fertilization is inferred to be effective for the selection of an embryo with low apoptosis positive cells (%).

Table 7 shows the presence of a significant correlation of the number of blastomeres and the presence or the absence of fragmentation at 31 hours after fertilization, and the blastocyst stage and oxygen consumption at 168 hours after fertilization with hatching capacity from the zona pellucida. Based on the results, the selection of an embryo consuming a large amount of oxygen at the expanded blastocyst stage and exhibiting a developmental stage of 2-cell stage and not undergoing fragmentation at 31 hours after fertilization is inferred to be effective for the selection of an embryo with high hatching capacity from the zona pellucida.

Examples of measurement results are shown in FIG. 2 to FIG. 5.

Figure 2:
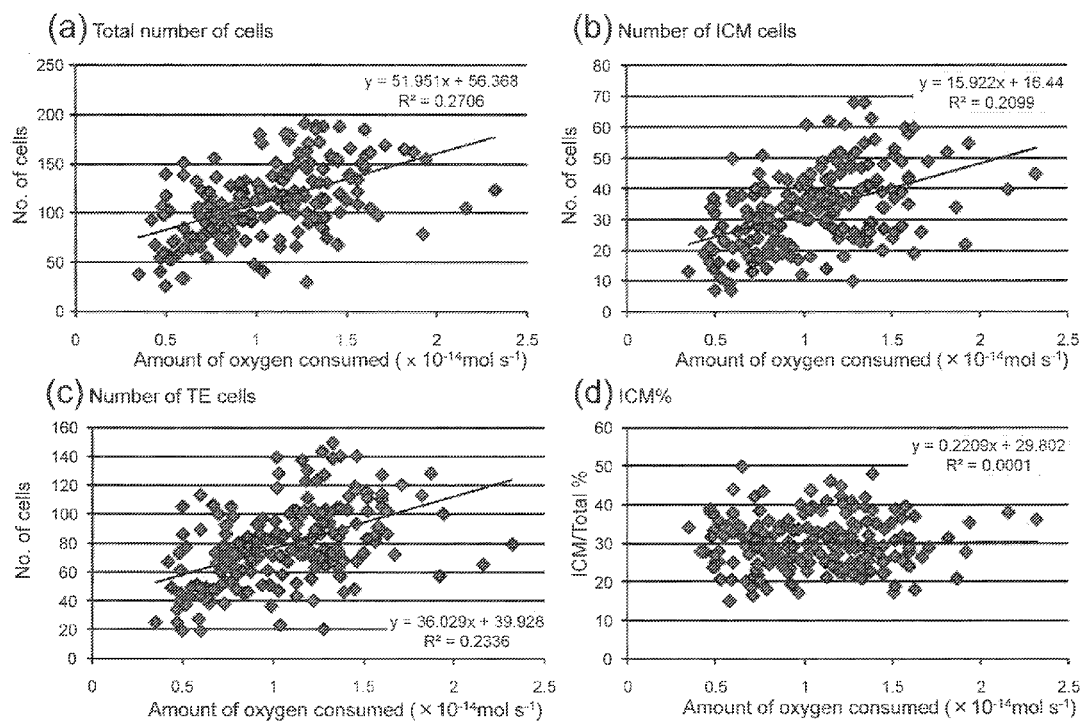
FIG. 2 shows the relationship between the number of cells of each type and oxygen consumed in a preliminary examination.

FIG. 2 shows the relationship between the number of cells of each type and oxygen consumption.

Figure 3A:
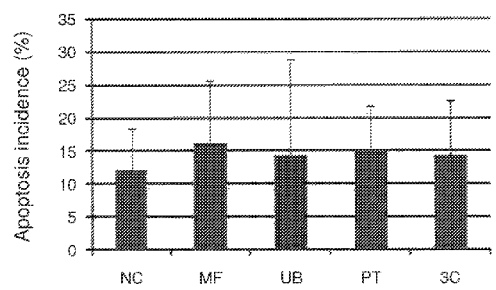
FIG. 3 shows the relationship between the first cleavage pattern at 31 hours after fertilization and apoptosis positive cells (%) (FIG. 3(a)), the relationship between the presence or the absence of fragmentation at 55 hours after fertilization and apoptosis positive cells (%) (FIG. 3(b)), the relationship between the number of blastomeres at 55 hours after fertilization and apoptosis positive cells (%) (FIG. 3(c)), and the relationship between the amount of oxygen consumed at 168 hours after fertilization and apoptosis positive cells (%) (FIG. 3(d)) in a preliminary examination.
Figure 3B:
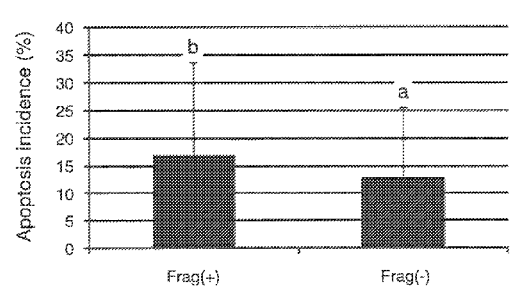
Figure 3C:
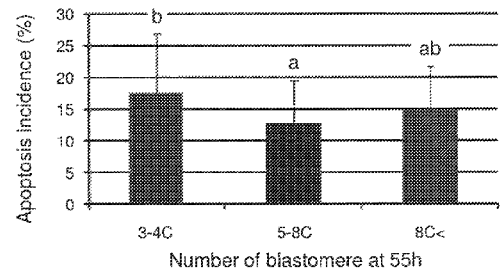
Figure 3D:
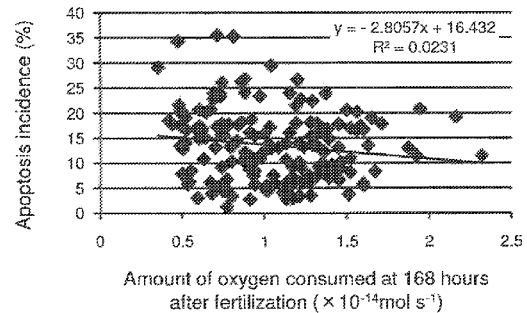

FIG. 3 shows the relationship (FIG. 3(a)) between first cleavage pattern at 31 hours after fertilization and apoptosis positive cells (%), the relationship (FIG. 3(b)) between the presence or the absence of fragmentation at 55 hours after fertilization and apoptosis positive cells (% O/), the relationship (FIG. 3(c)) between the number of blastomeres at 55 hours after fertilization and apoptosis positive cells (%), and the relationship (FIG. 3(d)) between the amount of oxygen consumed at 168 hours after fertilization and apoptosis positive cells (%).

In FIG. 3(a), "NC" indicates embryos exhibiting two blastomeres having the same size and not undergoing fragmentation. "MF" indicates embryos exhibiting 2 blastomeres, but undergoing a plurality of instances of fragmentation within the perivitelline space. "UB" indicates embryos exhibiting two non-uniform blastomere sizes. "PT" indicates embryos exhibiting 2 blastomeres, but having protrusions. "3C" indicates embryos that divided directly from the 1-cell stage to the 3-cell or 4-cell stage. The same applies to FIG. 4(a) and FIG. 5.

FIG. 4 shows the relationship (FIG. 4(a)) between first cleavage pattern at 31 hours after fertilization and hatching from the zona pellucida, the relationship (FIG. 4(b)) between the blastocyst stage at 168 hours after fertilization and hatching from the zona pellucida, and the relationship (FIG. 4(c)) between oxygen consumption at 168 hours after fertilization and hatching from the zona pellucida.

The results of FIG. 4(c) suggest that the capacity of embryos to hatch from the zona pellucida was low (32.6%) when the amount of oxygen consumed per single embryo at 168 hours after fertilization was $0.9 \times 10^{-14}$ mol s$^{-1}$ or less, and the capacity of embryos to hatch from the zona pellucida was significantly high (87.4%) when the same was higher than $0.9 \times 10^{-14}$ mol s$^{-1}$.

Figure 5:
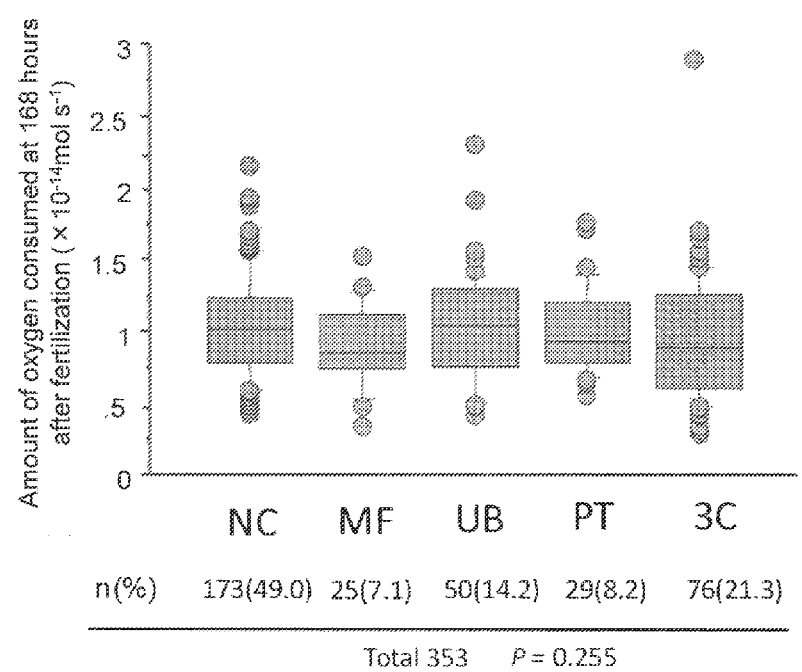
FIG. 5 shows the relationship between the first cleavage pattern at 31 hours after fertilization and oxygen consumption in a preliminary examination.

FIG. 5 shows the relationship between first cleavage pattern at 31 hours after fertilization and oxygen consumption. No significant difference due to differences in first cleavage pattern was observed in the amount of oxygen consumed. The result suggests the possibility that cytogenetically normal embryos (with no chromosome aberrations) cannot be efficiently selected only by measurement of the amount of oxygen consumed.

Experiment 3

Preliminary Examination of the First Cleavage Time

<Chromosome Number>

Developmental processes were followed using a real-time cell culture observation apparatus. The amounts of oxygen consumed by embryos that had reached the blastocyst stage (early blastocyst or expanded blastocyst) were then analyzed by SECM. Embryos used in this experiment were cattle (*Bos taurus*) embryos. Chromosome analysis was conducted according to Somfai et al. (2010). After measurement of the amounts of oxygen consumed, embryos were cultured with CR1aa supplemented with 100 ng/ml vinblastine and 5% CS for 17 hours, and then the cell cycle was stopped at the mitotic phase (M phase). Embryos were treated with 0.4 ml of 1% sodium citrate, and 0.02 ml of methanol acetate (1:1) was injected into the same solution for fixation. Ten (10) minutes later, embryos were placed on a slide glass. A small amount (1 µl) of acetic acid was added dropwise to the embryos, and then embryos were fixed again with ethanol acetate (1:3). Chromosome samples were air-dried sufficiently and then stained with 2% Giemsa solution for 10 minutes. Chromosome preparations were observed with an optical microscope. Chromosome numbers were analyzed by NIH ImageJ (v.1.40). Regarding all cells analyzed, embryos with 60 chromosomes (58 autosomes and 2 sex chromosomes) were determined to be normal and embryos other than such embryos were determined to be abnormal embryos. Based on time lapses and the results of measuring the amounts of oxygen consumed, factors (parameters) involved in chromosome number were analyzed by logistic regression analysis. As a result, the number of blastomeres at the time of completion of first cleavage and the number of blastomeres at the time of completion of third cleavage were found to exhibit a significant correlation (Table 8).

50 µl of an RNA extract (Arcturus) and then cultured at 42° C. for 30 minutes. Total RNA was extracted using a PicoPure RNA Isolation Kit (Arcturus) according to the instructions provided by the manufacturer. RevaTra Ace qPCR RT Kit (Toyobo Bio) was used for reverse transcription to cDNA. Quantitative real-time RT-PCR was performed using StepOnePlus™. The reaction conditions for

TABLE 8

Analysis of factors involved in the number of chromosomes

| Observation day | Predictive factor | Coefficient | Standard error | chi-square | P VALUE | Odds | 95% lower limit | 95% upper limit |
|---|---|---|---|---|---|---|---|---|
| Day 1 | First cleavage speed | −0.57 | 0.19 | 8.72 | 0.003 | 0.563 | 0.385 | 0.825 |
|  | Number of blastomeres (2-cell) | 2.08 | 0.68 | 9.52 | 0.002 | 8.032 | 2.138 | 30.18 |
|  | Non-uniform blastomeres | −0.29 | 0.62 | 0.21 | 0.648 | 0.752 | 0.221 | 2.555 |
|  | Fragmentation (+) | 0.4 | 0.69 | 0.34 | 0.562 | 1.493 | 0.386 | 5.776 |
| Day 2 | Number of blastomeres (3-cell to 5-cell) | −1.43 | 0.7 | 4.17 | 0.041 | 0.24 | 0.061 | 0.945 |
|  | Number of blastomeres (8-cell) | 0.2 | 0.59 | 0.11 | 0.739 | 1.216 | 0.385 | 3.845 |
|  | Non-uniform blastomeres | −0.04 | 0.58 | 0.01 | 0.941 | 0.958 | 0.306 | 2.995 |
|  | Fragmentation (+) | −0.61 | 0.78 | 0.6 | 0.439 | 0.545 | 0.118 | 2.53 |
| Day 7 | Oxygen consumption ($\times 10^{-14}$ mol s$^{-1}$) | 0.89 | 0.9 | 0.97 | 0.324 | 2.441 | 0.415 | 0.825 |

R = 0.54129

Figure 25:
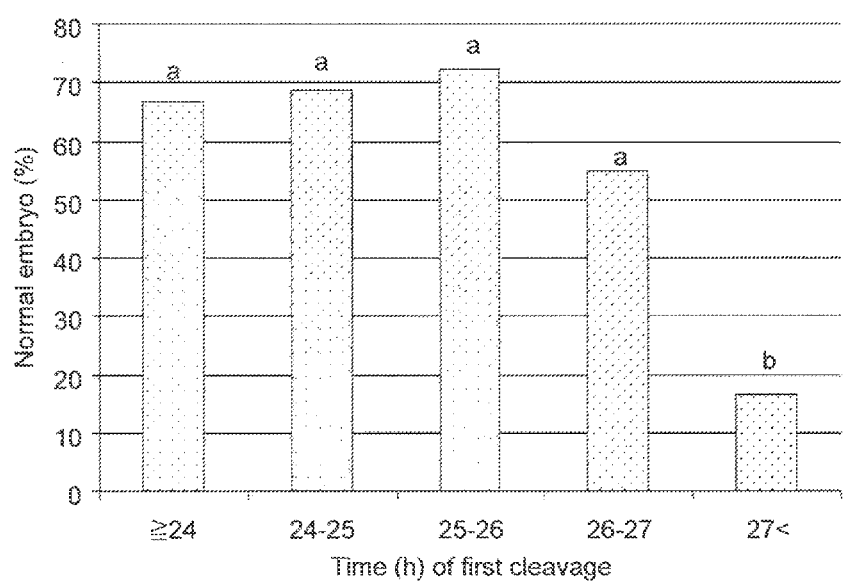
FIG. 25 shows the correlation between the first cleavage time and the proportion of all embryos having normal chromosome number.

The percentage of normal embryos was 16.7% for embryos that had performed cleavage at 27.25 hours after fertilization or later. This was significantly lower than the percentage (55.0% to 72.4%) of normal embryos for embryos that had performed cleavage within 27 hours after fertilization (Table 9 and FIG. 25).

TABLE 9

| Time (h) of first cleavage | N | Number of normal embryos | Normal embryos (%) |
|---|---|---|---|
| ≥24 | 12 | 8 | 66.7 |
| 24-25 | 32 | 22 | 68.8 |
| 25-26 | 29 | 21 | 72.4 |
| 26-27 | 20 | 11 | 55.0 |
| 27< | 18 | 3 | 16.7 |

<Gene Expression>

Figure 26:
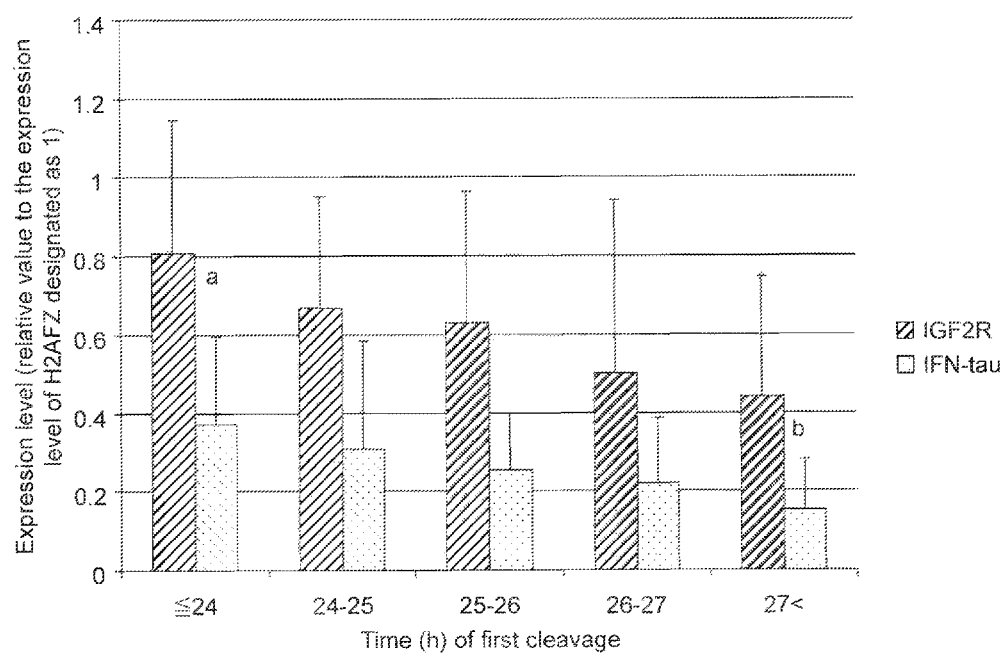
FIG. 26 shows the correlation between the first cleavage time and the expression levels of IGF2R and IFN-tau genes.

Developmental processes were followed using a real-time cell culture observation apparatus. The amounts of oxygen consumed by embryos that had reached the blastocyst stage (early blastocyst or expanded blastocyst) were then analyzed by SECM. In addition, embryos used in this experiment were cattle (*Bos taurus*) embryos. After measurement of the amounts of oxygen consumed, each embryo was added into Real-time PCR are as follows: 1 cycle of a reaction at 95° C. for 20 seconds, 43 cycles of a reaction at 95° C. for 3 seconds, a reaction at 60° C. for 10 seconds and a reaction at 72° C. for 20 seconds. The relative gene expression levels of genes (AKR1B1. IGF2R. IFN-tau, PLAC8, and CDX2) were calculated using H2AFZ (SEQ ID NO: 15) as an internal standard. Based on time lapses and the results of measuring the amounts of oxygen consumed, factors (parameters) involved in each gene expression were analyzed by multiple regression analysis. As a result, the time of the completion of first cleavage and the number of blastomeres were found to exhibit a significant correlation (Table 10 and Table 11) with IGF2R gene (SEQ ID NO: 13) expression and IFN-tau gene (SEQ ID NO: 14) expression. As the time of the completion of first cleavage was prolonged, the expression levels of IGF2 and IFN-tau (relative expression levels when the expression level of H2AFZ is designated as "1") decreased (Table 12 and FIG. 26).

The GeneBank Accession No. of each gene, the sequences of the primer set comprising a forward primer and a reverse primer used for PCR amplification of each gene using cDNA as a template, and the size of a fragment amplified using each primer set are shown in Table 13.

TABLE 10

Analysis of factors involved in IGF2R gene expression level

| Observation day | Predictive factor | Coefficient | Standard error | t | P value | 95% lower limit | 95% upper limit |
|---|---|---|---|---|---|---|---|
| Day 1 | Section | 1.664216 | 0.578774 | 2.875417 | 0.005798 | 0.503343 | 2.825089 |
|  | First cleavage speed | −0.05532 | 0.027302 | −2.02628 | 0.047781 | −0.11008 | −0.00056 |
|  | Number of blastomeres (2-cell) | 0.00556 | 0.108092 | 0.051435 | 0.959172 | −0.21124 | 0.222364 |
|  | Non-uniform blastomeres | −0.15758 | 0.09152 | −1.72182 | 0.090935 | −0.34115 | 0.025985 |
|  | Fragmentation (+) | 0.022328 | 0.107436 | 0.207828 | 0.836159 | −0.19316 | 0.237818 |
| Day 2 | Number of blastomeres (3-cell to 5-cell) | −0.06212 | 0.22072 | −0.28142 | 0.779482 | −0.50482 | 0.380593 |
|  | Number of blastomeres (8-cell) | −0.16087 | 0.097267 | −1.65393 | 0.104054 | −0.35596 | 0.03422 |
|  | Non-uniform blastomeres | 0.164481 | 0.129802 | 1.267169 | 0.210635 | −0.09587 | 0.424831 |
|  | Fragmentation (+) | 0.195535 | 0.16276 | 1.201371 | 0.234948 | −0.13092 | 0.521991 |
| Day 7 | Oxygen consumption ($\times 10^{-14}$ mol s$^{-1}$) | 0.005523 | 0.149779 | 0.036874 | 0.970724 | −0.29489 | 0.305941 |

R = 0.470904

TABLE 11

Analysis of factors involved in IFN-tau gene expression level

| Observation day | Predictive factor | Coefficient | Standard error | t | P value | 95% lower limit | 95% upper limit |
|---|---|---|---|---|---|---|---|
| Day 1 | Section | 1.348991 | 0.526841 | 2.560527 | 0.013336 | 0.292282 | 2.405701 |
| | First cleavage speed | −0.0642 | 0.024852 | −2.58325 | 0.012583 | −0.11405 | −0.01435 |
| | Number of blastomeres (2-cell) | 0.213821 | 0.098393 | 2.173135 | 0.03426 | 0.01647 | 0.411171 |
| | Non-uniform blastomeres | 0.115433 | 0.083308 | 1.385611 | 0.171669 | −0.05166 | 0.282528 |
| | Fragmentation (+) | 0.033742 | 0.097796 | 0.345027 | 0.73144 | −0.16241 | 0.229897 |
| Day 2 | Number of blastomeres (3-cell to 5-cell) | 0.080495 | 0.200915 | 0.400642 | 0.690295 | −0.32249 | 0.483479 |
| | Number of blastomeres (8-cell) | 0.058957 | 0.088539 | 0.665893 | 0.508367 | −0.11863 | 0.236544 |
| | Non-uniform blastomeres | −0.00876 | 0.118155 | −0.0741 | 0.94121 | −0.24574 | 0.228234 |
| | Fragmentation (+) | 0.069701 | 0.148156 | 0.470456 | 0.639959 | −0.22746 | 0.366864 |
| Day 7 | Oxygen consumption ($\times 10^{-14}$ mol s$^{-1}$) | −0.13359 | 0.136339 | −0.97984 | 0.331616 | −0.40705 | 0.139871 |

R = 0.550479

TABLE 12

| Time (h) of first cleavage | Mean relative expression level | | Standard deviation | |
|---|---|---|---|---|
| | IGF2R | IFN-tau | IGF2R | IFN-tau |
| ≤24 | 0.808056199 | 0.373663383 | 0.339397503 | 0.221325214 |
| 24-25 | 0.667286019 | 0.307488387 | 0.28324477 | 0.275255565 |
| 25-26 | 0.628273214 | 0.252575889 | 0.335132174 | 0.146115988 |
| 26-27 | 0.502522301 | 0.220931641 | 0.43761439 | 0.164729878 |
| 27< | 0.438219768 | 0.150608739 | 0.310875557 | 0.129144723 |

TABLE 13

| Gene | GeneBank Accession no. | Primer sequence (5'-3') F: Forward, R: Reverse | | Amplification size (bp) |
|---|---|---|---|---|
| CDX2 | XM_871005 | F: GCCACCATGTACGTGAGCTAC | (SEQ ID NO 1) | 140 |
| | | R: ACATGGTATCCGCCGTAGTC | (SEQ ID NO 2) | |
| INF-T | X65539 | F: TCCATGAGATGCTCCAGCAGT | (SEQ ID NO 3) | 103 |
| | | R: TGTTGGAGCCCAGTGCAGA | (SEQ ID NO 4) | |
| IGF2R | NM_174352.2 | F: GCTGCGGTGTGCCAAGTGAAAAAG | (SEQ ID NO 5) | 201 |
| | | R: AGCCCCTCTGCCATTGTTACCT | (SEQ ID NO 6) | |
| PLAC8 | NP_001070455.1 | F: CGGTGTTCCAGAGGTTTTCC | (SEQ ID NO 7) | 163 |
| | | R: AAGATGCCAGTCTGCCAGTCA | (SEQ ID NO 8) | |
| AKR1B1 | NM_001012519.1 | F: CGTGATCCCCAAGTCAGTGA | (SEQ ID NO 9) | 152 |
| | | R: AATCCCTGTGGGAGGCACA | (SEQ ID NO 10) | |
| H2AFZ | NM_174809 | F: ACAGCTGTCCAGTGTTGGTG | (SEQ ID NO 11) | 125 |
| | | R: GCAGAAATTTGGTTGGTTGG | (SEQ ID NO 12) | |

TABLE 14

| Stage | Code | Indicator | Number of implanted embryos | Conception (60 days) | Conception rate (%) |
|---|---|---|---|---|---|
| BL or ExBL | 1-2 | none | 22 | 7 | 31.8 a |
| Ex | 1 | none | 14 | 6 | 42.9 ab |
| BL or ExBL | 1-2 | #1 | 20 | 7 | 35.0 a |
| BL or ExBL | 1-2 | #2 | 19 | 10 | 52.6 ab |
| BL or ExBL | 1-2 | #3 | 19 | 8 | 42.1 ab |
| BL or ExBL | 1-2 | #4 | 15 | 8 | 53.3 ab |
| BL or ExBL | | #1-#4 combination | 12 | 9 | 75.0 b |

Stage: BL=blastocyst; and ExBL=expanded blastocyst, and Code are as defined in Robertson I, Nelson RE (1998) Certification and identification of the embryo. In: D. A.

Experiment 4

Relationship Between Four Indicators and Conception Rate

Cumulus-oocyte complexes (COCs) were collected from Japanese Black cattle by transvaginal ovum pick up (OPU). After 22 hours of in vitro maturation culture (IVM), in vitro fertilization (IVF) was performed. Developmental processes after IVF were observed using a real-time cell culture observation apparatus. The amounts of oxygen consumed by embryos that had reached the blastocyst stage (early blastocyst or expanded blastocyst) were then analyzed by SECM. Embryos were selected using the indicators listed below and then implanted into foster parents. On days 30 and 60 after embryo implantation, the presence or the absence of conception was confirmed by ultrasonic diagnosis.

Stringfellow and S. M. Seidel. Editors, Manual of the international embryo transfer society, IETS, Savoy, Ill. 103-116. Specifically, "Code 1" indicates a blastocyst or an expanded blastocyst wherein living cells accounted for 85% or more of all cells and "Code 2" indicates a blastocyst or an expanded blastocyst wherein living cells accounted for 50% or more of all cells. "Code 1-2" means "Code 1 or 2."

Indicator #1: the time taken from fertilization to the completion of first cleavage is 27 hours.

Indicator #2: the embryo is a 2-cell embryo and no fragmentation is observed at 31 hours after fertilization (upon completion of initial cleavage).

Indicator #3: the embryo is a 6-cell, 7-cell, or 8-cell embryo and no fragmentation is observed at 55 hours after fertilization (upon completion of third cleavage).

Indicator #4: the amount of oxygen consumed per single embryo at 168 hours after fertilization (the early blastocyst stage, the blastocyst stage, or the expanded blastocyst stage) is $0.91 \times 10^{-14}$ mol s$^{-1}$ or more.

DESCRIPTION OF SYMBOLS

1: side wall, 2: bottom wall, 3: cell holding section, 4: microwells, 5: inner wall, 6: bottom face of microwell, 10: culture vessel, 600, 700, 800, 900, 1000, 1100, and 1200: the embryo selection apparatus, 740, 840, 1140, and 1240: embryo selection system, 670, 770, 870, 970, 1070, 1170, and 1270: determination unit, 610, 710, 810, 908, 1006, 1108, and 1208: analysis unit, 606, 706, and 806: 1$^{st}$ indicator determination section, 607, 707, and 807: 2$^{nd}$ indicator determination section, 608, 708, and 808: 3$^{rd}$ indicator determination section, 609, 709, and 809: 4$^{th}$ indicator determination section, 750, 850, 1150, and 1250: image pickup apparatus, 760, 860, 1160, and 1260: apparatus for measuring the amount of oxygen consumed, S2001: determination step. S2002: analysis step All publications, patents, and patent applications cited herein are incorporated herein by reference in their entirety.

The invention claimed is:

1. An embryo selection apparatus for selecting a mammalian candidate embryo prepared by in vitro culture from a fertilized egg, comprising:
a determination unit;
an analysis unit;
a processing device; and
a non-transitory computer readable storage medium comprising program code configured to be executed by the processing device to implement the determination unit and the analysis unit,
wherein:
(a) the determination unit comprises M sections, wherein M is 2, 3, or 4, of the following:
(i) a first indicator determination section configured to determine whether time from fertilization to completion of first cleavage of a candidate embryo satisfies a first indicator selection criterion concerning the time from fertilization to the completion of first cleavage,
(ii) a second indicator determination section configured to determine whether a morphology of a candidate embryo at a stage after first cleavage and before second cleavage satisfies a second indicator selection criterion concerning the morphology at a stage after first cleavage and before second cleavage,
(iii) a third indicator determination section configured to determine whether a morphology of a candidate embryo at a stage after third cleavage and before fourth cleavage satisfies a third indicator selection criterion concerning the morphology at a stage after third cleavage and before fourth cleavage, and
(iv) a fourth indicator determination section configured to determine whether an amount of oxygen consumed by a candidate embryo at an early blastocyst stage, a blastocyst stage, or an expanded blastocyst stage satisfies a fourth indicator selection criterion concerning the amount of oxygen consumed at the early blastocyst stage, the blastocyst stage, or the expanded blastocyst stage;
(b) the determination unit comprises the fourth indicator determination section;
(c) the determination unit comprises at least one of the second indicator determination section and the third indicator determination section;
(d) the analysis unit is configured to analyze whether the mammalian candidate embryo satisfying N conditions in the determination unit is an embryo to be selected, wherein N is at least 2 and N is less than or equal to M.

2. The embryo selection apparatus according to claim 1, further comprising an image extraction unit, wherein:
(a) the determination unit comprises the first indicator determination section, the image extraction unit comprises a first image extraction section for (i) extracting an image at a threshold time point of the time from fertilization to the completion of first cleavage, or (ii) extracting an image with which a time point of the completion first cleavage can be confirmed, from a plurality of images of candidate embryos, and the first indicator determination section generates information based on the image extracted by the first image extraction section as a first indicator information;
(b) the determination unit comprises the second indicator determination section, the image extraction unit comprises a second image extraction section for extracting an image at a stage after first cleavage and before second cleavage from the plurality of images of candidate embryos, and the second indicator determination section generates information based on the image extracted by the second image extraction section as a second indicator information; or
(c) the determination unit comprises the third indicator determination section, the image extraction unit comprises a third image extraction section for extracting an image at a stage after third cleavage and before fourth cleavage from the plurality of images of candidate embryos, and the third indicator determination section generates information based on the image extracted by the third image extraction section as a third indicator information.

3. An embryo selection system for selecting a mammalian candidate embryo prepared by in vitro culture from a fertilized egg, comprising:
the embryo selection apparatus of claim 2; and
an image pickup apparatus for creating images of a plurality of candidate embryos, and outputting the images to the image extraction unit.

4. The embryo selection system of claim 3, wherein the embryo selection system further comprises an apparatus for measuring the amount of oxygen consumed by candidate embryos at the early blastocyst stage, the blastocyst stage, or the expanded blastocyst stage and outputting the measured amounts of oxygen to the fourth indicator determination section.

5. A non-transitory computer readable medium comprising program code configured to be executed by a processor, wherein execution of the program code by the processor causes the processor to execute an embryo selection method for selecting a mammalian candidate embryo prepared by in vitro culture from a fertilized egg,
wherein the method comprises determination and an analysis;
wherein the determination comprises M steps, wherein M is 2, 3, or 4 of the following:
a first indicator determination step for determining whether a first indicator information concerning time from fertilization to completion of first cleavage of a candidate embryo satisfies a first indicator selection criterion concerning the time from fertilization to the completion of first cleavage,
a second indicator determination step for determining whether a second indicator information concerning a morphology of a candidate embryo at a stage after first cleavage and before second cleavage satisfies a second indicator selection criterion concerning the morphology at a stage after first cleavage and before second cleavage;
a third indicator determination step for determining whether third indicator information concerning a morphology of a candidate embryo at a stage after third cleavage and before fourth cleavage satisfies a third indicator selection criterion concerning the morphology at a stage after third cleavage and before fourth cleavage; and
a fourth indicator determination step for determining whether fourth indicator information concerning an amount of oxygen consumed by a candidate embryo at an early blastocyst stage, a blastocyst stage, or an expanded blastocyst stage satisfies a fourth indicator selection criterion concerning the amount of oxygen consumed at the early blastocyst stage, the blastocyst stage, or the expanded blastocyst stage;
wherein the determination comprises the fourth indicator determination step; and
wherein the determination comprises at least one of the second indicator determination step and the third indicator determination step; and
wherein the analysis comprises analyzing whether the candidate embryo that satisfies at least N or more conditions determined by the determination step should be selected, wherein N is at least 2 and N is less than or equal to M.

* * * * *

SEQUENCE LISTING

<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
gccaccatgt acgtgagcta c                                                    21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
acatggtatc cgccgtagtc                                                      20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tccatgagat gctccagcag t                                                    21

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
tgttggagcc cagtgcaga                                                       19

<210> SEQ ID NO 5
<211> LENGTH: 24
<212> TYPE: DNA

```
<213> ORGANISM: Artificial Sequence
<220> FEATURE:
<223> OTHER INFORMATION: primer

<400> SEQUENCE: 5
gctgcggtgt gccaagtgaa aaag                                              24

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
agcccctctg ccattgttac ct                                                22

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
cggtgttcca gaggttttc c                                                  21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
aagatgccag tctgccagtc a                                                 21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cgtgatcccc aagtcagtga                                                   20

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
aatccctgtg ggaggcaca                                                    19

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
acagctgtcc agtgttggtg                                                   20
```

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcagaaattt ggttggttgg                                                    20

<210> SEQ ID NO 13
<211> LENGTH: 9075
<212> TYPE: DNA
<213> ORGANISM: Bos taurus

<400> SEQUENCE: 13
cgcccctcga gctcccccgg ctcgtccgtg gctcctcgcg ctcctgtccg tctccgcctg        60
ccgccctggc tgcacacccg tgtcccggac gccgccccg gccgccgcgc gccgctcgcc       120
cggctccgga cgcgcagccc gggcccggcg cgatggaggc ggccgccggc cggagctcgc       180
acctggggcc cgcgcccgcc gggcgcccgc cgcggtgccc gctcctgctg cagctgcagc       240
tgctgctgct gctgctgctg ctgccgccgg gctgggttcc cggggccgcg ggcacccagg       300
gcgccgagtt cccagagctg tgcagttata catgggaagc agtggatacc aaaaataaca       360
tgctttataa aatcaacatc tgtggaaata tgggtgttgc ccagtgtgga ccatcaagtg       420
ctgtctgtat gcatgacttg aagacagaca gctttcattc tgtgggtgac tctcttttga       480
aaacagcaag cagatctctt ctggaattta acacaacagt gaactgtaag cagcagaatc       540
acaaaattca gagtagcatc accttcttat gtgggaaaac cttgggaact cccgagtttg       600
taactgcaac agattgtgtg cattacttcg agtggaggac tactgcagcc tgcaaaaaga       660
atatatttaa agcgaataaa gaggtgccct gttacgcttt cgacagagag ctcaagaagc       720
acgatttaaa cccactgatc aagaccagcg gtgcttactt ggtggacgac tctgacccgg       780
acacatctct gttcatcaat gtctgcaggg acatagaggt gctccgggcc tcgagtccac       840
aagtgcgcgt gtgtcccacc ggcgcggccg cctgcctggt gcgagggac cgcgcgttcg       900 acgtgggccg gccccaggag gggctgaagc tcgtgagcaa tgacaggctc gtcctgagtt       960
acgtgaagga aggggccggc cagcccgact ctctgtgacgg ccacagcccg gcggtgacca      1020
tcacgttcgt gtgccccgtcg gagcgcagag agggcaccat tcccaagctc acagcgaaat      1080
ccaactgccg ctttgagatc gagtgggtca ccgagtacgc ctgccacagg gattacctgg      1140
aaagccggag ctgctcccctg agcagcgcgc agcatgacgt ggccgtcgac ctccagccgt      1200
tgagccgggt ggaagcctca gactccttgt tctacacctc ggaggcggac gagtatacat      1260
attatttgag catctgcgga ggaagccaag cgcccatctg taataagaaa gatgctgcag      1320
tgtgccaagt gaaaaaggca gattccactc aagtcaaagt ggccgggaga ccccagaacc      1380 tgacccctccg gtactcggat ggagacctca ccttgatcta tttcgggggt gaagagtgca      1440
gctccggctt ccagcggatg agtgtcatca acttcgagtg caatcagaca gcaggtaaca      1500
atggcagagg ggctcctgtg ttcaccgggg aggtggactc acctacttc ttcacgtggg      1560 atacgaagta cgcctgtgtc cacgagaagg aggccctgct gtgcggcgtc tccgacggga      1620
aacagcgctt cgacctgtcg gcgctggccc ggcactcaga actggaacaa aatgggaag      1680 ctgtggatgg cagtcagagg gaagcagaaa agaagcattt cttcattaac atctgccaca      1740

```
gggtcctgca gacgggccag gcacggggct gccccgaaga cgcggccgtg tgtgccgtgg      1800
ataagaatgg aagtaaaaat ctgggcagat ttatttcttc tcccaccaga gagaaaggaa      1860
atattcagct ctcttactca gatggtgatg agtgcggtgg tggccagaag ataataacaa      1920
atataacact catgtgcaaa ccaggtgatt tagaaagtgc cccggtgctg acaacctcca      1980
gggctgacgg ctgcttctac gagtttgagt ggcgcacggc tgcagcctgc gtgctctcca      2040
ggaccgaggg ggacaactgc actgtctttg actcccaggc agggttttct ttcgacttga      2100
cgcctctcac gaagaaggac gcctacaagg tcgagacgga caagtacgag ttccacatca      2160
acgtgtgcgg cccggtgtcc gtgggcgcct cccgccgga ctcggggggcc tgtcaggtgt      2220 ccaggagtga taggaagtct tggaacttgg gacgcagcaa tgctaagctt tcgtattacg      2280
acgggatgat ccagctgacc tacagggacg gcacaccta caataacgag aagcgcacgc      2340
cgagagccac gctcatcacc ttcctctgtg accgagacgc cggagtgggt ttccccgaat      2400
atcaggagga agataactct acatacaact tccggtggta caccagttac gcctgcccgg      2460
aggagccgct ggagtgcatc gtgactgacc ccgtcacact ggaccagtac gacctctcca      2520
ggctagcgaa atccgagggc ggtcctgggg gaaactggta ctctctggac aacggcgggg      2580
cacgcagcac gtggcggaag tactacatca acgtgtgtcg tcccctgaac ccggtgccgg      2640
gctgtgaccg ctacgcgtcc gcctgtcaga tgaagtacca gggcgagcag ggctcgtact      2700
ctgagaccgt ctccatcagc aacctggggg tggcgaagac gggccccatg gtggaggaca      2760
gcggcagcct gctcctggag tacgtcaacg gctccgcctg caccaccagc gaccagaggc      2820
gcaccaccta caccaccagg atccaccttg tctgctctac cggcagcctg tatacccatc      2880
ccatattttc tctcaactgg gagtgtgtgg tcagcttcct gtggaacacg gcggcagcct      2940
gtcctatccg aatcaccacg gacatagacc aggtctgctc catcaaggac cccaacagcg      3000
ggtacgtgtt tgatctgaac ccactgaaca attcccgagg atacgtggtt ttgggcatcg      3060
ggaagacgtt tctgttcaac gtgtgcggtg acatgcccgc ctgtggcacc ctggatggga      3120
agccagcttc cggctgcgag gcagaagtcc agatggacga catgaagacc ctgaagccgg      3180
gcaggctggt gggcctggag aagagcctgc agctgtccac cgagggcttt ataaccctga      3240
actacacggg gcttccttcc caccccaacg ggagggctga tgccttcatc atccgcttcg      3300
tctgcaatga tgacgtttac ccagggacac ccaagttcct gcaccaggac atcgactcta      3360
gcctggggat ccgggacact ttcttcgagt ttgaaaccgc gctggcctgt gtaccttctc      3420
cggtagattg ccaagtcaca gaccccgccg ggaacgagta tgatctgagt ggcctgagca      3480
aggccaggaa gccgtggact gcggttgaca cgttcgatga ggggaagaag aggaccttct      3540
acctgagcgt gtgcacgcct ctcccgtaca ttccggctg ccacggcacc gctgtggggt      3600
gctgcctggt gacggaagac agcaagttga acctaggcgt cgtgcagatc agtcctcagg      3660
tgggcgccaa cggtccctg agcctcgtct acgtcaacgg ggacaagtgc aagaaccagc      3720
gtttctccac caggataaac ctcgagtgtg cccacacaac gggctccccg acctttcagc      3780
tccagaacga ctgtgagtat gtgtttctct ggagaaccgt ggaagcctgt cccgtcgtgc      3840
gtgcggaagg agactactgc gaggtgagag acccaaggca cggcaacctg tataacctga      3900
tacctcttgg tctgaacgac actgtcgtgc gggccggcga atacacctat tacttccgcg      3960
tctgcgggga gctgacatcc ggcgtctgcc caaccagtga caagtccaag gtcatctcat      4020
catgccagga aaagcgggga ccccaggggat ttcaaaaagt ggcaggtctg tttaatcaga      4080
agctgaccta cgagaatggg gtgctgaaga tgaactacac cggggcgac acctgccaca      4140
```

```
aggtgtacca gcgttccacc accatctttt tctactgcga ccgcagcacg caggcgcccg    4200
tgtttctcca ggagacgtcc gattgctcct acctgtttga gtggcgcacg cagtacgcct    4260
gcccgcccta cgacctgacc gagtgttcgt tcaaaaacga ggctggggaa acctacgacc    4320
tctcgtctct gtcgaggtac agcgacaact gggaggctgt cacgggcaca gggtccaccg    4380
agcactacct catcaacgtg tgcaagtccc tgtccccgca ggctggctca gatccgtgcc    4440
ctccggaggc ggccgtgtgt ctgctgggcg ccccaagcc cgtgaacctg gcagggtgc      4500 gggacagtcc tcagtggagc cagggcttga ccctcctgaa gtacgttgac ggtgacttgt    4560
gtccagacca gattcggaag aagtcaacca ccatccgctt cacgtgcagc gagagccacg    4620
tgaactccag gcccatgttc atcagcgctg tggaggactg cgaatacacc ttctcctggc    4680
ccacggccgc cgcctgcgcg gtcaagagca acgtgcacga cgactgccag gtcaccaacc    4740
ccgccacggg acacctgttt gacctgagct ctctgagcgg ccgggccggc ttcaccgccg    4800
cctacagcga aaggggtta gtctacctca gcgtgtgcgg ggacaacgag aactgcgcca    4860
acggcgtggg ggcctgcttt gggcagacca ggatcagcgt gggcaaggcg agcaagaggc    4920
tgacctacgt ggaccaggtc ttgcaactgg tgtatgaggg cggctccccc tgcccctcca    4980
agaccggcct gagctacaag agcgtcatca gcttcgtgtg caggcctgag gtcgggccca    5040
ccaacaggcc catgctgatc tccctggaca agcgcacgtg cacgcttttc ttctcctggc    5100
acacacccct ggcctgcgag cagacgaccg agtgctccgt gaggaacggc agctccctca    5160
tcgacctgtc cccactcatc caccgcaccg ggggttacga agcatacgat gagagtgagg    5220
acgacggctc cgacaccagc cctgacttct acatcaacat ctgccagccg ctcaaccca    5280 tgcacgggtt ggcctgcccc gccggcacgg ccgtgtgcaa ggttcccgtg acggccccc    5340 cgatagatat tggccgagtg gcaggacctc cgatcctcaa tcccatagcc aacgaagttt    5400
acttgaactt tgaaagcagc actccttgct tggcggaccg gcacttcaac tacacctcac    5460
tgatcacgtt ccactgtaag cggggcgtga gcatgggaac gccaaaactg ctgaggacca    5520
gtgtgtgtga cttcgtgttt gagtgggaga ctcctctggt ctgtcccgac gaagtgaaga    5580
cggacggctg ctccctcacg gacgaacagc tgtactacag cttcaacctg tccagcctct    5640
ccaagagcac cttcaaggtg acccgaggcc cgcacaccta cagtgtgggg gtgtgcaccg    5700
cagccgcagg cctggacgaa ggaggctgca aggacggtgc tgtctgcctg ctgtccggga    5760
gcaagggggc gtcttttcggg cggctggcgt ccatgaagct ggactacagg catcaggacg    5820
aagctgtcat cctgagttac gccaacgag acacttgccc tccggaaact gaggacggcg    5880
agccgtgtgt gttccccttc gtgttcaacg ggaagagcta cgaggagtgt gttgtggaga    5940
gcagggccag gctctggtgc gcgaccaccg ccaactacga cagagaccac gagtgggggct   6000 tctgcaagca ctccaccagc caccggacgt ccgtcatcat cttcaagtgt gacgaggacg    6060
ccgacgtggg gcgccccag gtcttcagcg aggtgcgcgg ctgtgaggtg accttcgagt     6120
ggaagacgaa ggtggtctgc cccccgaaga agatggagtg caagttcgtc cagaagcacc    6180
ggacctacga cctgcggctg ctctcgtccc tcaccggctc ctggtccttc gtccacaacg    6240
gagcctcgta ctacatcaac ctgtgtcaga aaatatacaa gggaccccag gactgctcgg    6300
agagagccag cgtgtgcaaa aagagcacct ctggcgaggt gcaggtcctc gggctcgttc    6360
acacacagaa gctggatgtt gtagatgaca gagtcatcgt aacttactct aaaggccact    6420
actgtgggga caataagaca gcgtctgctg tcatcgagct gacctgtgcc aagacagtgg    6480
```

```
ggcggccttc gttcacgagg ttcgacgtcg acagctgcac ctaccacttc agctgggact    6540
cacgagcggc ctgcgccgtg aagcctcagg aggtgcagat ggtgaatggg accatcacca    6600
acccggccaa cggccggagc ttcagcctcg ggatattta cttcaaacga ttcagcgcct     6660
ctggggacgt gagaaccaac ggggacaggt acatctacga gatccagctg tcgtccatca    6720
cgggctccag cagccccgcc tgctctgggg ccagcatctg ccagaggaag ccaacgacc     6780 agcacttcag tcgcaaagtc ggaacctcca accaaaccag atactacgtt caagatggcg    6840
acctggatgt ggtgttcacc tcgtcctcca agtgtggaaa agacaagaca aagtctgtgt    6900
cctccaccat cttcttccac tgtgaccccc tggtgaagga cgggatcccc gagttcagcc    6960
acgagactgc cgactgccag tacctcttct cctggcacac ctctgccgtg tgcccgctgg    7020
gggcgggctt cgacgaggag atcgcagggg atgacgccca ggagcacaaa gggctctcag    7080
agcgcagcca ggcggtcggg gcagtgctca gcctgctgct ggtggcactc accgcctgcc    7140
tgctcaccct gctgctgtac aagaaggagc gccgggagat ggtaatgagc aggcttacca    7200
actgctgccg ccggagcgcg aacgtgtcct acaagtactc gaaggtgaac aaggaggagg    7260
aggccgacga gaacgagacc gagtggctga tggaggagat ccagccgccg gcgccgcggc    7320
ccgggaagga gggccaggag aacgggcacg tggccgccaa gtcggtgaga gctgccgaca    7380
cgctgagcgc cctgcacggc gacgagcagg atagcgagga cgaggtcctg acgctgcccg    7440
aggtgaaggt gcgcccgcca ggccgggctc ctggtgccga aggtggcccc ccgctgcggc    7500
cactgcctcg gaaggcgcca ccgccgctgc gggcggacga ccgggtgggg ctggtgcgtg    7560
gggagccggc gcgccggggg cggccccggg cggcggccac gcccatcagc accttccacg    7620
acgacagcga cgaggacctc ctgcacgtct aggctcgccc gcgccggctc cgaccaaatc    7680
cgatgggact ccgtgatgct tctgtccttg gcctttaacg aaaactgtcc aaaaaaggga    7740
agagtgttgg tggtggggga ggagggggc gcccctctcc gtgggcacgg ggaggaggcg    7800
cggccgctga tggccgcgcc agcccgggt ctgtccccag ccctcacctt gagcgtggcc    7860
gccgtgcgct tcctaaaggc gccggggcca gacgcgtctt gggactgagg ctgcctttta    7920
aggaagaccc ttgctgcttt aggccctgta gggtatttga tcattatatt ttagcattta    7980
attctctcct atttattgac ttttgacaat tactcaggtt tgcgaaaaaa gaaaaaaaaa    8040
aaaaaccacc aacagttttt tcctgccggc aggggggtaa cctttcctgt ccatcttta    8100 ggcgggggga ggctgtgggc atgctcggac gctttgaact ggtccaccat gtatcctctc    8160
agttagactc caccactctg tctcttctct tttgcttctg tggcgtcagg gcacacgggt    8220
gtgtgcgtgc gcacacgcgt gggtccgcgg ttgcctgggc tgtggaggga gccgcccgct    8280
ctctgcctcc cgagtcagta acagctgcag cctttttttt tttgcatgat gtcttcgatt    8340
ccaggtgcac agagcacact tatcagtatt tctctcgcca gctggtgaag tcaaacaacc    8400
cacccaaaga ttgatgtgtg tgtgtgtgtg tgtgcgtgtg tgcgtgtgtg cgcgcgtgca    8460
tgcgcacgcc tgtgcctagg tgcgcacatg tgtgtctgag agaatgggag tcgagatgtc    8520
agactttttt ccagacttgg ggtgtaggtc tcacctcttc aggttctcat gataccacct    8580
ttactgtgct tatttttta agaaaaaaaa aaagtgtct atcgaccatt cgacctataa     8640
gaagccttaa tttgcacagt gcgtgactca cggaagttgc atgaaagcca gtgggccagg    8700
ctctcgcccc cagccttgca cttggattcc cgcctgggca cggccaagac cggccgcccg    8760
gtccgcagga cggaggggg gaccgcgtcc ttccccggct gttggcgcct ttctctgaag    8820
tgtttaacga atgactttc tggcatttat agagctgtat atagactcag tggtattcat    8880
```

```
attctggaaa gccaaccaac ccgcagggtt cctgggtttg tactcttgtt tggctagctt      8940
atatgatttc aacatgagtg tattttaaa aattgatttc tttcctcatt ttttttccaa       9000
tcaaatttac tgtaatataa ggtattcaac gatttgaata aagataaat tattaaaaaa       9060 aaaaaaaaaa aaaaa                                                      9075

<210> SEQ ID NO 14
<211> LENGTH: 1165
<212> TYPE: DNA
<213> ORGANISM: Bos taurus

<400> SEQUENCE: 14
tgactacatt tcctaggtca aacagaaaat atctaactga aaacacaaac aggaagtgag       60
agagaaattt tcggataatg agtaccgtct tccctattta aaagccttgc ttagaacgat      120
catcatcaga gaacctacct gaaggttcac ccagacccca tctcagccag cccagcagca      180
gccacatctt ccccatggcc ttcgtgctct ctctactgat ggccctggtg ctggtcagct      240
acggcccggg acgatctctg ggttgttacc tgtctgagga ccacatgcta ggtgccaggg      300
agaacctcag gctcctggcc cgaatgaaca gactctctcc tcatccctgt ctgcaggaca      360
gaaaagactt tggtcttcct caggagatgg tggagggcaa ccagctccag aaggatcagg      420
ctatctctgt gctccatgag atgctccagc agtgcttcaa cctcttctac acagagcact      480
cgtctgctgc ctggaacacc accctcctgg agcagctctg cactgggctc aacagcagc      540 tggaggacct ggacgcctgc ctgggcccag tgatgggaga gaaagactct gacatgggaa      600
ggatgggccc cattctgact gtgaagaagt acttccaggg catccatgtc tacctgaaag      660
aaaaagaata cagtgactgc gcctgggaaa tcatcagaat ggagatgatg agagccctct      720
cttcatcaac caccttgcaa aaaaggttaa gaaagatggg tggagatctg aactcacttt      780
gagatgactc tcgctgacta agatgccaca tcaccttcgt acactcacct gtgttcattt      840
cagaagactc tgatttctgc ttcagccacc gaattcattg aattacttta actgatactt      900
tgtcagcagc aataagcaag tagatataaa agtactcagc tgtagggggca taagtcctta      960 agtgatgcct gccctgatgt tatctgttgt tgatttatgt attccttctt gcatctaaca      1020
tacttaaaat gttaggaaat ttgtaaagtt acatttcatt tgtacatcta ttaaaatttc      1080
taaaacatgt ttaccatttt gtgttattaa atttgtcctt tgttctattt attaaatcaa      1140
agaaaatgag tttctttact caaaa                                           1165

<210> SEQ ID NO 15
<211> LENGTH: 948
<212> TYPE: DNA
<213> ORGANISM: Bos taurus

<400> SEQUENCE: 15 gcctttctc tgccttgctt gcttgagctt cagcggaatt cgaaatggct ggcggtaagg       60
ctgggaagga ctccggaaag gccaagacaa aggcggtttc ccgctcgcag agagccggtt      120
tgcagttccc ggtgggccgt attcatcgac acctgaaatc taggacgact agccatggac      180
gtgtgggcgc gactgccgct gtgtacagcg cagccatcct ggagtacctc accgcagagg      240
tacttgaatt ggcaggaaat gcatcgaaag acttgaaggt aaagcgtatt accctcgtc       300 acttgcaact tgctattcgt ggagatgaag aattggactc tctcatcaag gctacaattg      360
ctggtggtgg tgtcattcca cacatccaca aatctctgat tggaaagaaa ggacaacaga      420
```

-continued

```
agactgtcta aaggatgcct ggattcctta ttatctcagg actctaaata ctctaacagc      480
tgtccagtgt tggtgattcc agtggactgt atctctgtga aaaacacaat tttgcctttt      540
tgtaattcta tttaagcaag ttggaagttt aattagcttt ccaaccaacc aaatttctgc      600
atttgagtct taaccatatt taagtgttac tgtggcttca aagaagctat tgatgctgaa      660
gtagtgggtt ttgattgagt tgactgtttt taaaaaactg tttggatttt aattgtgatg      720
cagaagttat agtaacaaac atttggtttt gtacagacat tatttccact ctggtggata      780
agctcaataa aggtcatatc ccaaactgtt gtgtataaaa tttgcttgat tatagtagga      840
acagctttgt tgaataggta tcttacctag caataactta agcacatttc ttccctttaa      900
attactgtta attctgtctg tagatcacaa agttaaaagg cccaagtg                   948
```